United States Patent
Vink et al.

(10) Patent No.: US 10,184,136 B2
(45) Date of Patent: Jan. 22, 2019

(54) RETROVIRAL VECTORS

(71) Applicant: UCL Business PLC, London (GB)

(72) Inventors: Conrad Vink, London (GB); Steven Howe, London (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 15/029,898

(22) PCT Filed: Oct. 16, 2014

(86) PCT No.: PCT/GB2014/053102
§ 371 (c)(1),
(2) Date: Apr. 15, 2016

(87) PCT Pub. No.: WO2015/056014
PCT Pub. Date: Apr. 23, 2015

(65) Prior Publication Data
US 2016/0230191 A1    Aug. 11, 2016

(30) Foreign Application Priority Data

Oct. 16, 2013 (GB) .................................... 1318347.0

(51) Int. Cl.
| | | |
|---|---|---|
| C12N 15/63 | (2006.01) | |
| C12N 15/86 | (2006.01) | |
| C12N 7/00 | (2006.01) | |
| C12N 15/85 | (2006.01) | |

(52) U.S. Cl.
CPC .............. *C12N 15/86* (2013.01); *C12N 7/00* (2013.01); *C12N 15/8509* (2013.01); *C12N 2740/15043* (2013.01); *C12N 2740/16022* (2013.01); *C12N 2740/16043* (2013.01); *C12N 2740/16052* (2013.01); *C12N 2830/48* (2013.01)

(58) Field of Classification Search
None
See application file for complete search history.

(56) References Cited

U.S. PATENT DOCUMENTS

2002/0123146 A1   9/2002  Klatzmann et al.
2005/0266544 A1   12/2005 Young et al.

OTHER PUBLICATIONS

Uk Search Report issued in corresponding United Kingdom Application No. 1318347.0, dated Jun. 26, 2014.
Vink et al., "LTR1: A Novel Lentiviral Vector Designed to Deliver Less HIV-1 DNA to Target Cells," Molecular Therapy, vol. 22, Supplement 1, p. S289, May 2014.
Vink et al., "Improvements in vector design: the novel LTR-1 lentivirus delivers less HIV-1 DNA to target cells," Human Gene Therapy, vol. 25, No. 5, p. A14, May 2014.
Vink et al. "Elimination of packaging sequences from lentiviral vector DNA delivered to target cells," Human Gene Therapy, vol. 24, No. 12, Dec. 2013, p. A74.
Vink et al., "LTR1 Lentiviral Vectors," UCL Institute of Child Health, Apr. 14, 2014.
Fang et al., "A self-deletion lentiviral vector to reduce the risk of replication-competent virus formation," The Journal of Gene Medicine, 2013; 15:102-112.
Kim et al., "The Determination of Importance of Sequences Neighboring the Psi Sequence in Lentiviral Vector Transduction and Packaging Efficiency," PLoS One, Nov. 2012, vol. 7, Issue 11.
International Search Report issued in corresponding International Application No. PCT/GB2014/053102, dated Feb. 9, 2015.
Feb. 9, 2015—International Search Report—WO app PCT/GB2014/053102.
Feb. 1, 2013—"A self-deletion lentiviral vector to reduce the risk of replication-competent virus formation"—Yudan Fang—The Journal of Gene Medicine.
Nov. 21, 2012—"The Determination of Importance of Sequences Neighboring the Psi Sequence in Lentiviral Vector Transduction and Packagin Efficiency"—Seon hee Kim, et al.—PLoS One.

*Primary Examiner* — Celine X Qian
(74) *Attorney, Agent, or Firm* — Banner & Witcoff, Ltd.

(57) ABSTRACT

There is disclosed a retroviral vector comprising a primer binding site, a long terminal repeat and an RNA packaging sequence, wherein the RNA packaging sequence is located 3' of the long terminal repeat and no long terminal repeat is located 3' of the RNA packaging sequence such that reverse transcription initiated at the primer binding site does not lead to reverse transcription of the RNA packaging sequence into vector DNA in a target cell. Also described is a host cell, a virion, a pharmaceutical composition, a method and uses including or involving the vector described above. Further, a cell or transgenic animal produced by using the vector is also described.

20 Claims, 6 Drawing Sheets
Specification includes a Sequence Listing.

RETROVIRAL VECTORS

FIELD OF THE INVENTION

The present invention relates to a retroviral vector in which the cis elements are located downstream of the 3' LTR. These elements are therefore present in the viral RNA genome so that it can be packaged into virions, but are outside of the region of the genome that is reverse transcribed and so are not present in the vector DNA in the target cell. This reduces the disadvantages associated with transfer vector cis element persistence in target cells.

BACKGROUND TO THE INVENTION

Retroviral vectors were among the earliest viral vectors developed for mammalian gene transfer. A number of retroviral species have been developed into vectors, notably alpharetroviruses (1), gammaretroviruses (2), the lentivirus human immunodeficiency virus type 1 (HIV-1) (3), nonhuman lentiviruses (4), and spumaviruses (5).

The most important structural change in moving from retrovirus to retroviral vector is the separation of viral non-coding sequences required in cis on the nucleic acid undergoing gene transfer from the viral protein coding sequences required in trans in the producer cell for the production of virions. This separation renders the vector capable of only one round of infection as no viral proteins are produced in target cells.

A standard third generation HIV-1-based lentiviral vector such as RRL or CCL (3) requires co-transfection of four plasmids into producer cells during virion production (FIG. 1): a transfer vector containing the essential cis elements and the transgene expression cassette, a packaging plasmid expressing the HIV-1 polyproteins Gag and Gag-Pol, a plasmid for the expression of the HIV-1 Rev protein, and a plasmid for expression of the viral envelope protein. Lentiviral vectors are able to incorporate envelope proteins from other enveloped viruses if they are co-expressed in producer cells, a phenomenon known as pseudotyping. The most commonly used envelope protein is the vesicular stomatitis virus glycoprotein (VSVG) which confers stability and broad tropism upon lentiviral vector virions (6).

The essential cis elements contained within the transfer vector include the HIV-1 long terminal repeats (LTRs), the RNA packaging signal ($\Psi$), and preferably the Rev Response Element (RRE). The LTRs contain sequences required for transcription, reverse transcription, and integration of the vector genome. In self-inactivating (SIN) transfer vectors almost all of the viral 3' U3 region has been removed in order to eliminate its promoter and enhancer activities (3). The mechanism of reverse transcription is such that both proviral U3s originate from the 3' LTR of the RNA genome, so proviruses resulting from infection with this vector lack LTR-driven transcription and cannot transcribe their full genome efficiently in target cells. The RNA packaging signal is thought to extend into the beginning of the gag coding sequence, but a point mutation has been introduced downstream of the gag start codon to prevent translation of the majority of this sequence. The Rev protein interacts with the RRE in producer cells to stabilise transcripts, promote RNA export from the nucleus, and enhance RNA packaging into virions (7; 8). Non-essential but commonly used cis elements include an HIV-1-derived central polypurine tract (cPPT) which enhances transduction of non-dividing cells (9) and a woodchuck hepatitis virus post-transcriptional regulatory element (WPRE) which enhances viral titre and transgene expression through improving the efficiency of polyadenylation (10).

In a standard third generation lentiviral vector these cis elements are reverse transcribed along with the transgene expression cassette in target cells, resulting in a provirus incorporating two SIN LTRs containing 236 bp of HIV-1 DNA in each, a primer binding site (PBS) to Gag region containing 490 bp of HIV-1 DNA, an RRE containing 858 bp of HIV-1 DNA, and a Nef to polypurine tract (PPT) region containing 69 bp of HIV-1 DNA, making a total of 1889 bp of HIV-1 DNA delivered to target cells. These viral cis elements are covalently attached to the transgene expression cassette and persist in target cells after transduction. If an integrating lentiviral vector is used, they are irreversibly integrated into target cell chromosomes.

Consequences of Transfer Vector cis Element Persistence in Target Cells

The long term persistence of HIV-1-derived cis elements in target cells creates a number of experimentally observed and theoretically possible problems for the practical application of lentiviral vectors in studying the biological effects of transferred genes on cell culture or animal models, the generation of transgenic animal strains and stable cell lines, and the transfer of therapeutic genes to treat human disease.

Firstly, the transfer vector cis elements contain active splice acceptor sites which are able to splice with host cell genes to create aberrant fusion transcripts (11-13). An event of this type was observed in a gene therapy clinical trial in which splicing between a copy of the patient's growth-promoting HMGA2 gene and an integrated lentiviral provirus caused dysregulation of HMGA2 transcription and a large clonal expansion of a transduced cell (14).

Secondly, the persistence of cis elements required for RNA packaging enables remobilisation of self-inactivating lentiviral vector genomes in cells expressing viral proteins (15). If used in patients infected with HIV this could result in remobilised lentiviral vector proviruses and recombination with wildtype HIV-1 genomes.

Thirdly, lentiviral cis elements contain untranscribed CpG-rich DNA which is subject to DNA methylation and may contribute to reduction in expression of the delivered transgene through silencing in host cells (16).

Fourthly, large untranscribed regions within episomal DNA vectors have been associated with transgene silencing in vivo (17). Reducing the size of the untranscribed region within an episomal integration-deficient lentiviral vector (IDLV) may therefore improve long term expression in applications of these vectors.

Fifthly, reducing the size of the reverse transcript may increase the transgene carrying capacity of lentiviral vectors. There are potentially multiple stages of the lentiviral life cycle which are limiting for vector genome size, such as RNA packaging (18), reverse transcription in cell types with low intracellular dNTP concentration (19), and integration into chromosomes.

Minimisation of cis Elements within Target Cell Proviruses

Several approaches have been taken towards the goal of minimising the viral cis elements which persist within target cell proviruses.

Firstly, a number of authors have investigated the effect of simple deletions and point mutations to remove or inactivate the remaining cis elements. Cui et al reported point mutations to the HIV-1 major splice donor (MSD) positioned upstream of Gag as well as further incremental deletions of the Gag and RRE elements resulting in a transfer vector containing 550 bp of HIV-1 cis DNA (or 786 bp if both LTRs in the provirus are accounted for) (20). In 293T producer cells these changes resulted in a large decline in expression of unspliced transfer vector RNA, but in TE671 cells this effect was less pronounced due to cell type-specific splicing patterns and the resulting decline in titre was only 2-fold. This system has not been widely adopted within the field, perhaps due to a combination of the reduction in titre and the unusual producer cell line. Kotsopoulou et al reported an attempt to generate a Rev-independent lentiviral vector by codon optimisation of the packaging plasmid and deletion of the RRE from the transfer vector, resulting in a 5-fold reduction in titre (21). It has since been reported that the Rev/RRE system is required for efficient packaging of transfer vector RNA into virions (8). Koldej et al reported minimisation of the amount of Nef coding sequence upstream of the PPT (22). The entire sequence appears to be dispensable up to the run of 5 thymidine bases immediately upstream of the PPT.

A second approach towards the minimisation of cis elements within target cell proviruses is to design vectors in which these elements are present in the viral RNA genome but subsequently deleted during reverse transcription or integration.

Delviks et al reported a gammaretroviral vector in which the RNA packaging signal was flanked by a 701 bp repeat of the herpes simplex virus thymidine kinase gene (HSV-TK) (23). During reverse transcription in target cells, template switching by the reverse transcriptase from one repeat to the other resulted in the deletion of the RNA packaging signal. Since template switching is not an obligatory activity for the reverse transcriptase, the efficiency of this deletion was reported to be 91% of clones. This strategy to delete cis elements has the disadvantage of requiring a new cis element to be introduced (in this case, HSV-TK) which is not itself deleted. Patents and patent applications derived from this vector include U.S. Pat. No. 5,741,486, U.S. Pat. No. 5,714,353 and WO 95/032298. A similar strategy was used by Srinivasakumar in a lentiviral vector in which the RRE was flanked by repeat copies of the hygromycin phosphotransferase gene, resulting in deletion of the RRE in 84% of clones (24).

Torne-Celer et al used the ability of retroviral integrases to cleave internal att sites to generate alpharetroviral vectors in which the 5' LTR and the RNA packaging signal are cleaved off the pre-integration complex by the viral integrase enzyme during the 3' end processing stage of integration (25). While 61% of clones in this report carried the expected deletion, internal att site processing appears to produce heterogeneous proviral products and results in titres that are $10^2$ to $10^3$-fold lower than would be expected with a more conventional alpharetroviral vector (26).

A third approach towards the minimisation of lentiviral cis elements is to remove them from target cell proviruses following transduction. Luche et al reported a lentiviral vector in which the RNA packaging signal was flanked with loxP sites so that it could be excised when Cre recombinase was provided in trans in target cells (27). In transduced 293T cells the excision was successful in 12-20% of transduced cells. Fang et al reported a self-minimising lentiviral vector incorporating a Cre recombinase expression cassette which excised the RNA packaging signal, RRE and itself following target cell transduction (28). Successful excision as measured by loss of Cre expression took place in 92% of target cells. Both of these strategies rely on the successful expression and function of Cre recombinase in target cells, and it is highly unlikely that such a strategy would receive regulatory approval for use in patients in the near future.

SUMMARY OF THE INVENTION

The inventors of the present invention have sought to minimise cis elements within target cell proviruses in an alternative way to reduce the disadvantages associated with transfer vector cis element persistence in target cells.

In existing lentiviral vectors, cis elements such as the RNA packaging signal and the RRE are located between the two viral LTRs and so are within the region of the genome that is reverse transcribed. In the vector described in this invention, these cis elements are located downstream of the 3' LTR. These elements are therefore present in the viral RNA genome so that it can be packaged into virions, but are outside of the region of the genome that is reverse transcribed and so are not present in the vector DNA in the target cell.

Accordingly, in a first aspect of the invention, there is provided a retroviral vector comprising a primer binding site, a long terminal repeat and an RNA packaging sequence, wherein the RNA packaging sequence is located 3' of the long terminal repeat such that reverse transcription initiated at the primer binding site does not lead to reverse transcription of the RNA packaging sequence into vector DNA in a target cell. In other words, reverse transcription of the vector leads to the RNA packaging sequence being excluded from the reverse transcript produced in a target cell. In this vector, no long terminal repeat is located 3' of the RNA packaging sequence.

The retroviral vector can be based on any suitable retrovirus which is able to deliver genetic information to eukaryotic cells. For example, the retroviral vector may be an alpharetroviral vector, a gammaretroviral vector, a lentiviral vector or a spumaretroviral vector. Such vectors have been used extensively in gene therapy treatments and other gene delivery applications. In some embodiments, the retroviral vector is a lentiviral vector. In some instances, the retroviral vector may be based on HIV-1.

The vector comprises a primer binding site (PBS). This is a site which binds to a tRNA primer which is responsible for initiating minus strand synthesis during the reverse transcription process. The primer binding site may be located either 5' or 3' of the long terminal repeat. Preferably, this primer binding site is located towards the 5' end of the vector. Preferably, the primer binding site is located on the 5' side of the long terminal repeat.

In some embodiments, the vector comprises a second primer binding site. Preferably, this is located on the 3' side of the long terminal repeat (LTR). In some embodiments, these two primer binding sites are referred to as a 5' primer binding site and a 3' primer binding site. In some embodiments, the second primer binding site is located next to the LTR on the 3' side. Preferably, the second primer binding site is located between the LTR and the RNA packaging sequence so that the RNA packaging sequence is located 3' of the second primer binding site.

The primer binding sites bind to a tRNA primer which is responsible for initiating minus strand synthesis during the reverse transcription process. The primer binding sites also provide homology for plus strand transfer during the reverse transcription process.

The vector comprises a long terminal repeat (LTR). Preferably, this is located towards the 3' end of the vector (although some components, such as the RNA packaging sequence, may be positioned further towards the 3' end of the vector).

In some embodiments, the vector comprises two long terminal repeats, referred to as a 5' LTR and a 3' LTR. The 5' LTR is located towards the 5' end of the vector (although there may be components further towards the 5' end). Where two LTRs are present, the primer binding site is preferably located on the 3' side of the 5' LTR (but on the 5' side of the 3' LTR). The primer binding site may be located next to the 5' LTR on the 3' side.

Retroviral LTRs are generally segmented into U3, R, and U5 regions. However, in certain LTRs, parts of these regions may be deleted. The term "long terminal repeat" or "LTR" is intended to cover all such variations in LTRs. The LTR participates in the reverse transcription process so that vector DNA is produced in the target cell based on the vector RNA. LTRs can comprise a number of signals required for gene expression such as a transcriptional enhancer, a promoter, a transcription initiation signal and/or a polyadenylation signal.

The LTR may be a self-inactivating (SIN) LTR. In the vector, for enhanced safety the LTR is preferably a self inactivating LTR in which nucleotides in the U3 region have been deleted. This can include the TATA box and binding sites for transcription factors. The deletion is transferred to the 5' LTR after reverse transcription in target cells, resulting in the transcriptional inactivation of the LTR in the proviruses.

Where the vector comprises two LTRs, both may be SIN LTRs. The U3 region of the 5' LTR may be replaced with a promoter such as the cytomegalovirus (CMV) or Rous Sarcoma Virus (RSV) promoter. This results in Tat-independent transcription but still maintains high levels of expression. As above, the 3' LTR has had nucleotides deleted from the U3 region. SIN LTRs are well known to those skilled in the art (e.g. see Retroviruses. Edited by Coffin J M, Hughes S H, and Varmus H E. Cold Spring Harbor (N.Y.): Cold Spring Harbor Laboratory Press; 1997).

Preferably, where the vector comprises one LTR, the vector comprises two PBSs. One PBS is located towards the 5' end of the vector (5' PBS) and may be positioned precisely on the transcription start site for the promoter which drives transcription of the vector genome. One PBS is located towards the 3' end of the vector, 3' of the LTR (3' PBS). The 3' PBS acts as the site of initiation of minus strand synthesis during the reverse transcription process. The 5' PBS provides homology for plus strand transfer during the reverse transcription process.

Preferably, where the vector comprises two LTRs (a 5' LTR and a 3' LTR), the vector comprises one PBS. The PBS is located towards the 5' end of the vector (5' PBS) and is position 3' of the 5' LTR. The PBS acts as the site of initiation of minus strand synthesis and provides homology for plus strand transfer during the reverse transcription process.

In a particular embodiment, the invention provides a retroviral vector comprising: a 5' primer binding site; a 3' long terminal repeat; an RNA packaging sequence; and either a 3' primer binding site or a 5' long terminal repeat, wherein the RNA packaging sequence is located 3' of the 3' long terminal repeat such that the RNA packaging sequence is not reverse transcribed into vector DNA in a target cell.

The vector comprises an RNA packaging sequence which is located 3' of the long terminal repeat such that the RNA packaging sequence is not reverse transcribed into vector DNA in a target cell. In embodiments in which the vector comprises two long terminal repeats, the RNA packaging sequence is located 3' the 3' long terminal repeat (i.e. 3' of both LTRs) such that the RNA packaging sequence is not reverse transcribed into vector DNA in a target cell. The RNA packaging sequence is necessary for the essential process of packaging the retroviral RNA genome into the viral particle as it is assembled by the producer cell. The RNA packaging sequence is able to bind to viral proteins within the nascent viral particle. In some embodiments, the RNA packaging sequence comprises the RNA packaging signal (T). In HIV-1, a portion of the gag gene has found to be involved in RNA packaging. The RNA packaging sequence may also comprise the Rev Response Element (RRE). RNA packaging sequences and the components that make this up are well know to those skilled in the art (e.g. see Retroviruses. Edited by Coffin J M, Hughes S H, and Varmus H E. Cold Spring Harbor (N.Y.): Cold Spring Harbor Laboratory Press; 1997).

In some embodiments, the vector further comprises an exogenous nucleotide sequence for delivery into a target cell. This exogenous nucleotide sequence may be any sequence which someone might want to insert into a target cell. For example, the exogenous nucleotide sequence may be an expressible transgene, an RNA interference cassette or a molecular barcode, for example, for marking the lineage of different cells. The exogenous nucleotide sequence should be located between the PBS (5' PBS where there are two PBSs) and the LTR (3' LTR where there are two LTRs).

In some embodiments, the exogenous nucleotide sequence an expressible transgene. This transgene is a non-retroviral gene and may be any gene the expression of which is desired in a target cell. The expressible transgene should be located between the PBS (5' PBS where there are two PBSs) and the LTR (3' LTR where there are two LTRs). The transgene may encode for a peptide or protein, or a noncoding RNA. In some embodiments, the transgene encodes for a peptide or protein. Preferably, the peptide or protein should be useful in gene therapy. In some embodiments, the transgene is under the control of a promoter (e.g. a PGK or GAPDH promoter).

Expression of the transgene may aid normal growth of the cell or maintain the health of a subject. In some embodiments, the transgene encodes for a peptide or protein which is absent or underexpressed in a subject. Alternatively, the transgene may encode for a peptide or protein which helps to prevent or ameliorate a medical condition. The peptide or protein may be one which is useful in treating diseases such as cancer, atherosclerosis, sickle-cell anaemia, infection, metabolic disorders, neurological illness and the thalassemias. Examples of such peptides and proteins are haemoglobin, hematopoietic growth factors such as granulocyte-macrophage colony stimulating factor (GM-CSF), macrophage colony stimulating factor (M-CSF), granulocyte colony stimulating factor (G-CSF), erythropoietin (EPO), common gamma chain, Wiskott Aldrich Syndrome protein (WASp), GP91phox, and ABCD1. Another example is tumour necrosis factor (TNF), which is a molecule that can be used to treat cancer, and in particular, tumours. The tumour suppressor p53 and retinoblastoma (RB) are also contemplated. Various cytokines such as mast cell growth factor (MGF) and interleukins 1-11 are also proteins which are contemplated by the present invention. A multidrug resistance gene (mdR) encoding p-glycoprotein is also contemplated as the transgene. The peptide or protein may also be a selectable marker for antibiotic resistance in eukaryotes. Other types of selectable markers such as adenine phosphoribosyl transferase (APRT) in APRT-deficient cells, a fluorescent protein or the firefly luciferase gene are also included. The peptide or protein can be a protein that will provide the host with an additional or altered enzymatic activity, such as the herpes simplex virus thymidine kinase protein for 'suicide therapy' of reactive transplants, or a toxin, such as the diphtheria toxin protein for treatment of cancer. The transgenes encoding these proteins can be provided by any of a variety of methods, such as routine cloning procedures (Sambrook et al. (1989), Molecular Cloning: A Laboratory Manual, Cold Spring Harbor, N.Y.), excision from a vector containing the gene of interest, or chemical or enzymatic synthesis based on published sequence information. In many instances the DNA encoding the protein of interest is commercially available. In another embodiment, the transgene encodes a protein which enables experimental manipulation of the cell, for example a toxin or a fluorescent or drug-selectable marker.

In another preferred embodiment, the transgene is capable of being transcribed into a noncoding RNA molecule. In some embodiments, the transgene may encode a noncoding RNA which can alter the level of expression of genes within the cell or is a component of a ribonucleoprotein complex with enzymatic activity. Examples of such noncoding RNAs are short interfering RNAs (siRNAs), microRNAs, small nucleolar RNAs (snoRNAs), small nuclear RNAs (sn-RNAs), piwi-interacting RNAs (piRNAs), long noncoding RNAs, transfer RNAs (tRNAs) and ribosomal RNAs (rR-NAs). In some embodiments, the transgene may encode a noncoding RNA which is sufficiently complementary to hybridize to an mRNA or DNA of interest. Such an RNA molecule is an antisense RNA, and has utility in preventing or limiting the expression of over-produced, defective or otherwise undesirable molecules or to investigate the function of a gene. The vector of the present invention can comprise, as the transgene, a sequence encoding an antisense RNA which is sufficiently complementary to a target sequence such that it binds to the target sequence. For example, the target sequence can be part of the mRNA encoding a polypeptide such that it binds to and prevents translation of mRNA encoding the polypeptide. In another embodiment, the target sequence is a segment of a gene that is essential for transcription such that the antisense RNA binds the segment (e.g. a promoter or coding region) and prevents or limits transcription. Hence, the antisense RNA must be of sufficient length and complementarily to prevent translation of its target mRNA or transcription of its target DNA. One of ordinary skill in the art can determine antisense molecules having sufficient complementarily to a target sequence such that the antisense molecule is capable of binding to the target and thereby inhibiting translation or transcription. The transgene sequence can be provided, for example, by chemical or enzymatic synthesis, or from commercial sources.

The vector may comprise further elements which help in transduction and expression of the vector. These elements are generally located between the PBS (5' PBS where there are two PBSs) and the LTR (3' LTR where there are two LTRs).

For example, the vector may further comprise a 3' polypurine tract (3' PPT). This is a site which is resistant to the RNAseH activity of the retroviral reverse transcriptase when present in RNA. Preferably, this is located 5' of the LTR (the 3' LTR if there are two). The PPT may be located next to the LTR (the 3' LTR if there are two) on the 5' side.

The vector may further comprise a central polypurine tract (cPPT). The vector may further comprise a post-transcriptional regulatory element (PRE) such as a woodchuck hepatitis virus post-transcriptional regulatory element (WPRE). In some embodiments, the vector further comprises a central polypurine tract (cPPT) and a post-transcriptional regulatory element (PRE).

The vector may further comprise a polyadenylation (polyA) signal such as the simian virus 40 (SV40) early or late polyadenylation (polyA) signal. Preferably, the polyA signal is located 3' of the RNA packaging sequence. Preferably, the vector further comprises a SV40 late polyA signal. Preferably, this is located at the 3' end of the vector after the other components such as the RNA packaging sequence.

The vector preferably comprises a promoter to drive transcription of the vector genome. This may be any suitable promoter, including a Rous Sarcoma Virus (RSV) promoter, a human cytomegalovirus (CMV) immediate early promoter, a spleen focus forming virus (SFFV) promoter or an HIV-1 U3 promoter. This promoter is preferably positioned at the 5' end of the vector.

Preferably, the primer binding site of the vector is positioned precisely on the transcription start site for the promoter which drives transcription of the vector genome. Where there are two PBSs, the 5' PBS is preferably positioned precisely on the transcription start site for the promoter which drives transcription of the vector genome.

Preferably, a retroviral major splice donor (MSD) site is located near the 5' end of the vector close to the promoter. This MSD may be located 3' of the PBS (the 5' PBS where there are two). This has been found to increase titre levels of the vector.

In one embodiment in which the vector comprises one LTR and two PBSs, the vector comprises, in 5' to 3' direction, the following components: 5'-promoter-PBS-expressible transgene-LTR-PBS-RNA packaging sequence-3'.

In one embodiment in which the vector comprises two LTRs and one PBS, the vector comprises, in 5' to 3' direction, the following components: 5'-promoter-LTR-PBS-expressible transgene-LTR-RNA packaging sequence-3'.

In one embodiment in which the vector comprises one LTR and two PBSs, the vector comprises, in 5' to 3' direction, the following components: 5'-promoter-PBS-MSD (optional)-cPPT (optional)-expressible transgene-WPRE (optional)-PPT-LTR-PBS-MSD (optional)-RNA packaging sequence-polyA signal (optional)-3'.

In one embodiment in which the vector comprises two LTRs and one PBS, the vector comprises, in 5' to 3' direction, the following components: 5'-promoter-LTR-PBS-MSD (optional)-cPPT (optional)-expressible transgene-WPRE (optional)-PPT-LTR-MSD (optional)-RNA packaging sequence-polyA signal (optional)-3'.

In another embodiment, there is provided a host cell containing the vector described above. The host cell may be any suitable eukaryotic cell into which the vector may be introduced.

Plasmids encoding the retroviral vectors of the present invention are transfected into suitable host cells (or packaging cells) by standard methods known to one of ordinary skill in the art. Suitable packaging cells are defined herein as cells that contain helper virus sufficient to allow the packaging of RNA transcribed from the retroviral vector and the release of vector virus particles, or virions. Generally additional plasmids encoding trans-acting viral sequences but lacking the cis-acting sequences required for packaging are co-transfected. These supply the required structural and enzymatic proteins to package and produce the expressed viral backbone RNA. Such packaging cells are known and available to one of ordinary skill in the art, and include, for example, HEK293T cells.

Recombinant retrovirus produced from the transfected cells is harvested by standard methods. The harvested retrovirus, in the form of virions, is used to transduce a permissive target cell by standard techniques. A target cell is defined herein as any cell that is permissive to infection by the virus produced by the retroviral vector of the present invention. The target cell can be in vivo or ex vivo. Representative target cells include, for example, bone marrow stem cells, hepatocytes, muscle cells, tumour cells, neurons, retina and airway epithelial cells. The provirus that is formed in the target cell can then express the transgene. Because the provirus contains no RNA packaging sequence, any endogenous helper proteins present cannot trigger production of an infectious virus from the provirus.

In a further embodiment, there is provided a virion containing the vector described above.

Also provided is a pharmaceutical composition comprising the vector or virion described above. The pharmaceutical composition may further comprise one or more pharmaceutically acceptable excipients.

Additionally, there is provided a vector or virion for use in therapy, in particular, gene therapy.

A vector or virion for use in delivering a transgene to a subject in gene therapy is also provided.

The invention provides a method of delivering a gene to a target cell, the method comprising administering an effective amount of a vector or virion to the target cell. This method can be used to create a cell line which expresses a gene of interest. For example, the gene can encode for a biotherapeutic so that the cell line produces the biotherapeutic, for example, a therapeutic protein or antibody.

The invention also provides a cell produced by the above method.

Furthermore, there is provided a method of delivering a gene to a target cell in a subject, the method comprising administering an effective amount of a vector or virion to the subject.

The subject may be human or animal. Where the subject is human, the gene can be delivered to the subject as part of gene therapy so that the gene is expressed in the subject. Where the subject is an animal, the above method can be used to produce a transgenic animal in which the gene is expressed.

The invention also provides a transgenic animal produced by the above method.

The invention will now be described in detail, by way of example only, with reference to the following figures.

DETAILED DESCRIPTION OF THE INVENTION

Summary

Lentiviral transfer vector cis elements such as the HIV-1 RNA packaging signal (Ψ) and Rev Response Element (RRE) are essential for viral RNA genome packaging into virions in producer cells. In standard lentiviral vectors, these cis elements are reverse transcribed into DNA along with the transgene expression cassette and persist in target cells after transduction. This persistence creates several known and potential problems for lentiviral vector gene therapy applications. Splice sites within cis elements have been shown to splice with nearby host genes, creating aberrant fusion transcripts. The CpG island within the RNA packaging sequence undergoes DNA methylation in some target cells, potentially contributing to transgene silencing. The RNA packaging sequence also enables remobilisation of lentiviral vector genomes in cells expressing lentiviral proteins, which could be problematic in HIV-positive patients. Large packaging sequences within the reverse transcript may reduce the size of the transgene cassette which can be accommodated.

In standard lentiviral vectors, essential cis elements are located between the two viral long terminal repeats (LTRs) and so are within the region of the vector that is reverse transcribed. The inventors have developed a novel transfer vector in which the RNA packaging signal and the RRE are located downstream of the 3' LTR so are present in the RNA genome during virion packaging but are outside of the region of the genome that is reverse transcribed into DNA in the target cell. These vectors can be produced to high titre ($2.6 \times 10^8$ TU/ml by eGFP flow cytometry of 293Ts, pCCL parallel preparation $1.3 \times 10^9$ TU/ml) and eGFP expression is maintained to 14 days post-transduction. It is suggested that the use of this configuration to eliminate most of the remaining viral DNA from target cell proviruses could be a feature of the next generation of gene therapy vectors based on HIV-1 and other retroviruses.

Introduction

Figure 1:
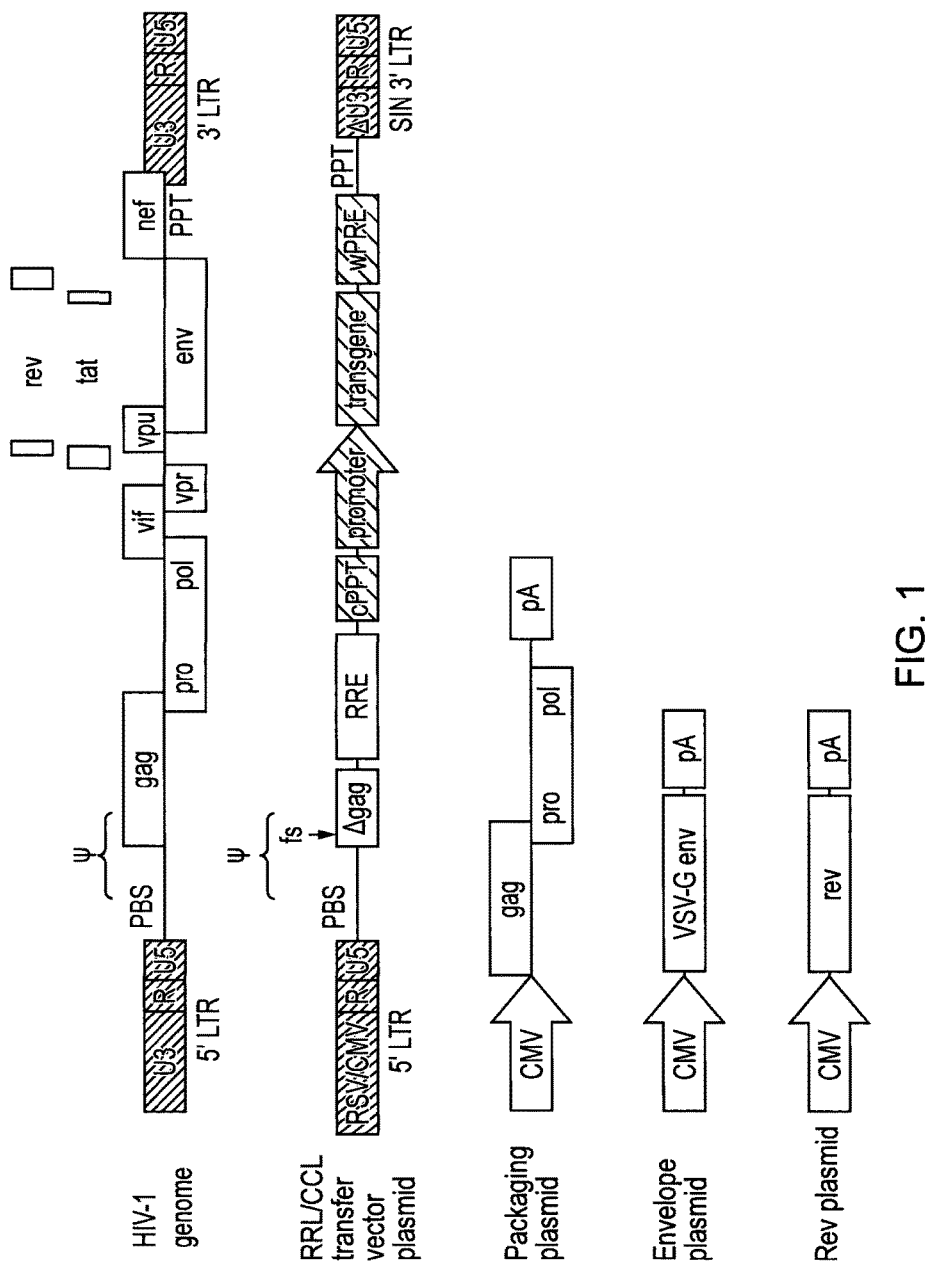
FIG. 1. Schematic representation of the HIV-1 genome and an RRL/CCL third generation lentiviral vector system derived from it. U3, unique in 3' region' R, repeat region; U5, unique in 5' region; PBS, primer binding site; Ψ, RNA packaging signal; PPT, polypurine tract; LTR, long terminal repeat; RSV, Rous Sarcoma Virus U3 promoter; CMV, human cytomegalovirus immediate early promoter; Δgag, truncated gag sequence; fs, frameshift mutation; RRE, Rev Response Element; cPPT, central polypurine tract; wPRE, woodchuck hepatitis virus posttranscriptional regulatory element; ΔU3, self-inactivating U3 region; pA, polyadenylation signal; VSV-G, vesicular stomatitis virus glycoprotein.
Figure 2:
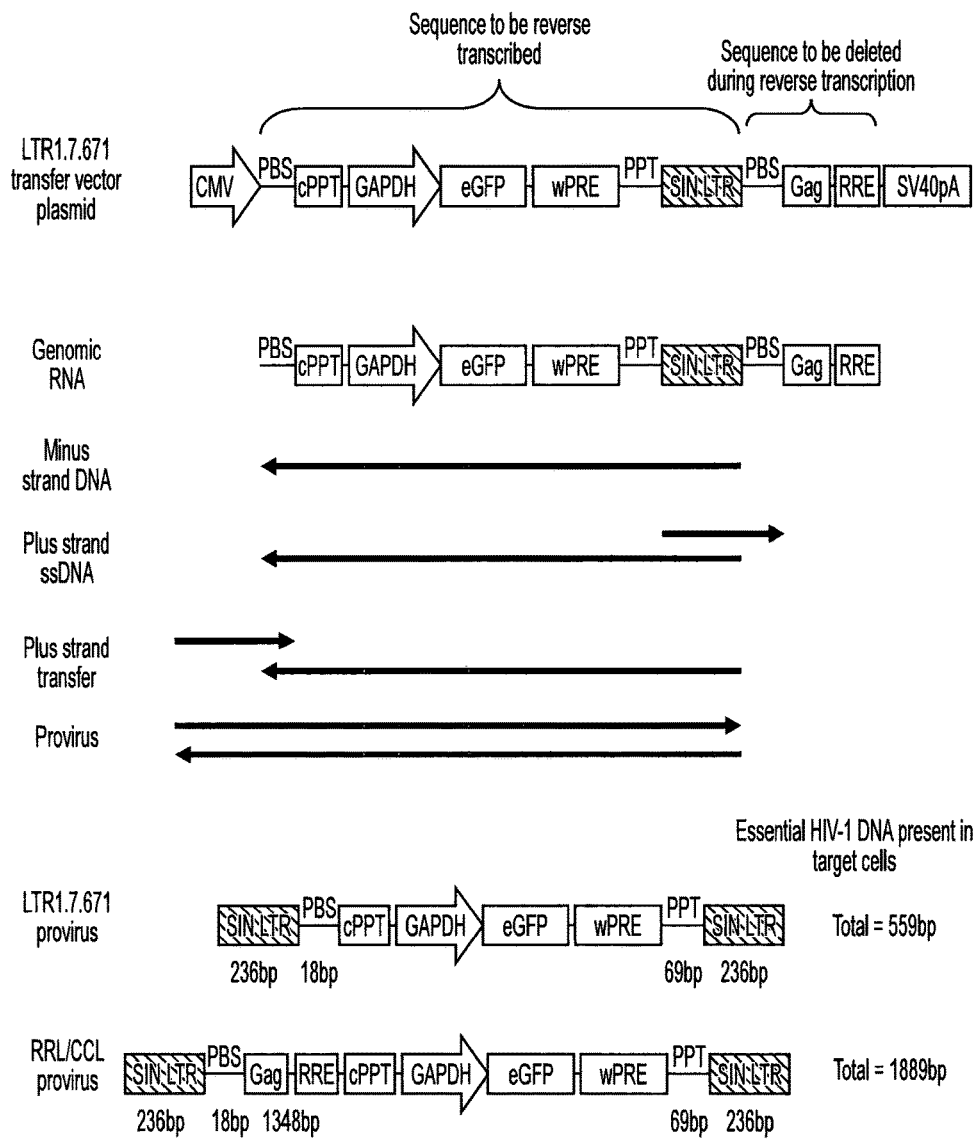
FIG. 2. Schematic of the vector plasmid developed in this invention and schematic of reverse transcription of LTR1 vectors showing that packaging sequences (Gag+RRE) at the 3' end of the RNA genome are not reverse transcribed. SIN LTR, self-inactivating LTR; SV40pA, simian virus 40 polyadenylation signal; GAPDH, human glyceraldehyde 3-phosphate dehydrogenase promoter; eGFP, enhanced green fluorescent protein.

In existing lentiviral vectors, cis elements such as the RNA packaging signal and the RRE are located between the two viral LTRs and so are within the region of the genome that is reverse transcribed. In the LTR1 vector described in this invention, the cis elements are located downstream of the 3' LTR (FIG. 2). These elements are therefore present in the viral RNA genome so that it can be packaged into virions, but are outside of the region of the genome that is reverse transcribed and so are not present in the vector DNA in the target cell. The name "LTR1" was chosen because these vectors contain only one LTR in the transfer vector plasmid rather the two LTRs present in a conventional lentiviral vector.

Figure 3:
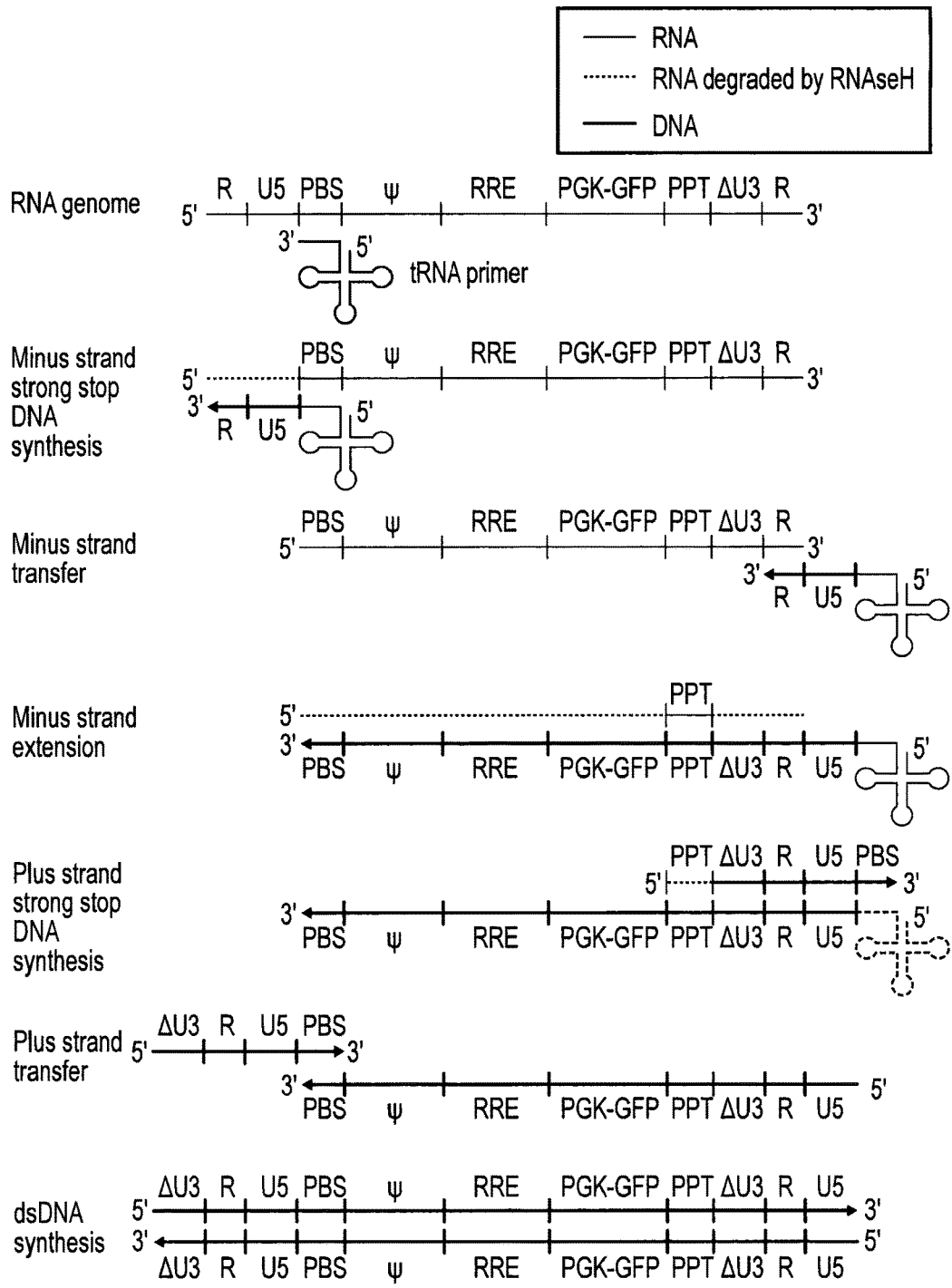
FIG. 3. Detailed schematic of third generation lentiviral vector reverse transcription showing that all sequences are reverse transcribed. PGK, human phosphoglycerate kinase promoter.

To understand the mechanism behind this invention it is useful to outline with the classical model of retroviral reverse transcription employed by third generation lentiviral vectors such as RRL or CCL (FIG. 3). In these vectors (as in those from previous generations), the substrate for reverse transcription is a viral RNA genome located in the target cell. A host-derived tRNA molecule bound to the PBS acts as a primer for the initiation of minus strand DNA synthesis by the viral reverse transcriptase enzyme. Once initiated, minus strand synthesis proceeds to the end of the 5' R region. As the minus strand is synthesised, the RNaseH activity of reverse transcriptase degrades the RNA strand of the resulting RNA-DNA double stranded hybrid. Upon reaching the end of the 5' R region, minus strand transfer occurs via homology between the R regions on the minus strand DNA and the 3' end of the RNA genome. Minus strand synthesis continues from this region. RNaseH degradation continues, but a short PPT within the RNA genome immediately upstream of the U3 region is not degraded. The PPT acts as a primer for the initiation of plus strand DNA synthesis. Plus strand synthesis continues into the tRNA primer and stops after the first 18 bp due to the presence of a modified RNA nucleotide at the next position in the tRNA which reverse transcriptase cannot use as a template. Plus strand transfer then occurs via homology between the complementary PBS sequences on each DNA strand, and synthesis of both DNA strands continues until a full length double stranded DNA provirus is created.

Figure 4:
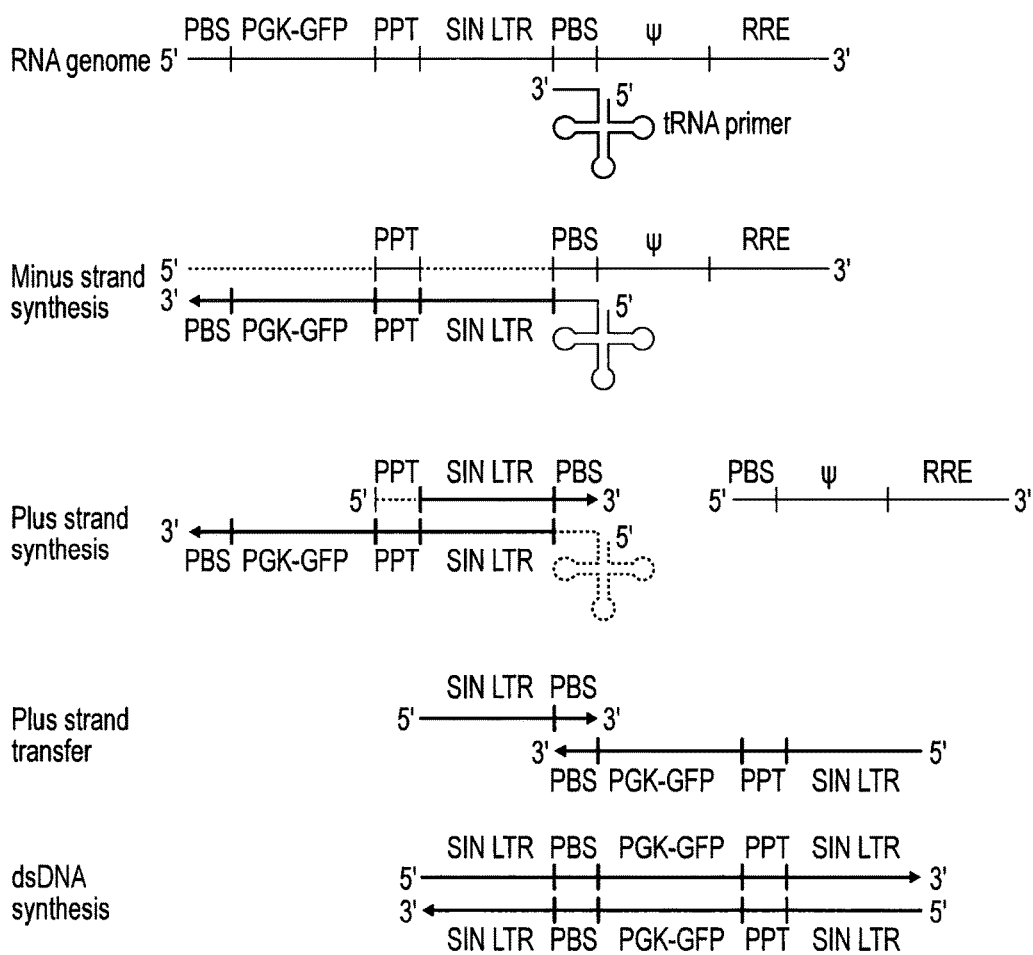
FIG. 4. Detailed schematic of LTR1 reverse transcription showing exclusion of the PBS-Ψ-RRE RNA sequence from the reverse transcript.

The LTR1 vector described in this invention uses a different mechanism for reverse transcription (FIG. 4). In this vector, the tRNA primer is predicted to be bound to a PBS located closer to the 3' end of the RNA genome. A tRNA molecule bound to the 5' PBS cannot initiate minus strand synthesis because there is no template upstream from this position. After minus strand synthesis initiates at the 3' PBS, it proceeds to the end of the 5' PBS without a minus strand transfer step taking place. Plus strand synthesis initiates at the PPT as before and plus strand transfer occurs via homology between the complementary PBS sequences before synthesis of the double stranded DNA provirus. The 3' end of the RNA genome including the RNA packaging signal and RRE is predicted not to be reverse transcribed as it lacks homology with both the minus and plus strands, so cannot be primed for reverse transcription. Instead it is predicted to be separated from the reverse transcription complex and eventually degraded by target cell RNases.

A number of reports confirm the novel configuration of the LTR1 genome is competent for packaging into virions and reverse transcription in target cells. Firstly, it has been shown that the HIV-1 RNA packaging signal and RRE remain capable of efficient packaging into virions when relocated close to the centre of heterologous RNA molecules (8). Secondly, it has been shown that a PBS flanked by the appropriate local HIV secondary structure remains capable of efficient initiation of minus strand synthesis when relocated to the centre of a lentiviral vector genome (29).

The practical development of a lentiviral vector which employs this novel reverse transcription mechanism to eliminate cis elements such as the RNA packaging signal and the RRE from target cell proviruses is described herein.

1. Materials and Methods 1.1. Plasmids

The parental plasmids for the constructs described in this invention were the pRRL.SIN and pCCL.SIN lentiviral transfer vector plasmids for HIV-1 components, the PGK promoter, the eGFP cDNA and the wPRE (3), the pCI plasmid for the SV40 late polyadenylation signal (Promega), and gene synthesis of the GAPDH promoter (Life Technologies) based on the University of California, Santa Cruz (UCSC) human genome build hg19 between the primer sequences described in (30). The sequences for all plasmids are provided in the Appendix. Plasmids pCMV-dR8.74 and pMDG2 were generated and distributed by Didier Trono at the Ecole Polytechnique Federale de Lausanne.

1.2. Preparation of Lentiviral Vectors $1.2 \times 10^7$ HEK293T (293T) cells were seeded in T175 flasks in 20 ml Dulbecco's Modified Eagle's Medium supplemented with 10% fetal calf serum and 1% pencillin-streptomycin (complete DMEM) one day before transfection to reach >90% confluence. For each flask, 50 μg vector plasmid, 32.5 μg packaging plasmid pCMV-dR8.74, and 17.5 μg vesicular stomatitis virus envelope plasmid pMDG2 was added to 5 ml Optimem (Gibco) and 0.22 μm filtered. 1 μl 10 mM PEI (Sigma-Aldrich 40872-7) was added to 5 ml Optimem and 0.22 μm filtered. The two mixtures were combined and allowed to complex for 20 min. The complex was added to the T175 flask containing 293T cells and incubated at 37° C. with 5% $CO_2$ for 4 hours. The complex was removed and replaced with 20 ml complete DMEM. 24 hours later, the medium was replaced. 48 hours after transfection the medium was removed, 0.22 μm filtered, and centrifuged at 50,000 g for 2 hours. Virus pellets were resuspended in 1500 Optimem and aliquots were stored at −80° C.

1.3. Titration of Lentiviral Vectors by Flow Cytometry $10^5$ 293T cells were seeded in 250 μl of complete DMEM into each well of a 24-well plate one day before transduction. For transduction, a 5-fold dilution series of virus was performed in 50 μl aliquots of Optimem. Each aliquot of diluted virus was added to the medium in one well. Transgene expression was measured by flow cytometry 14 days post-transduction. Expression titre was calculated by selecting the well in which 5-15% of transduced cells expressed the transgene of interest and dividing the number of transduced cells in this well by the volume of virus used to transduce them.

1.4. Plasmid Rescue

Briefly, HEK 293T cells were transduced at high MOI with LTR1.20/AmpR-ori, containing an Ampicillin resistance gene and bacterial origin of plasmid replication, and left to culture for 1 week before recovery of cell pellets. Genomic DNA was extracted using a commercial kit (Qiagen) and quantified by Nanodrop. 10 μg of gDNA was digested with XbaI restriction endonuclease, which does not target any sequence within the provirus, but exists within the human genome at an incidence of approximately 279.3 sites per megabase pair. The digested gDNA was then column purified before ligation to circularise any released lentiviral backbone fragments, followed by transformation of electrocompetent *Escherichia. coli*. Individual bacterial colonies were selected and grown in preparation for sequence analysis; these would only grow if they received a recircularised copy of the vector backbone containing AmpR and ori. Recovered DNA was sequenced using the primers targetting the RRE region (which should be omitted from the final provirus), the bacterial origin of replication and the ampicillin resistance gene.

2. Results

2.1. Optimisation of the Genomic RNA Transcription Cassette

The production of infectious lentiviral virions requires co-assembly of the viral genomic RNA with viral Gag, Gag-Pol and envelope proteins. Previous reports of codon-optimised Gag-Pol expression plasmids improved the intracellular expression of these proteins but did not result in higher titres (21; 31). It is likely that expression of the viral RNA genome is generally the limiting factor for viral titre in many vector preparation protocols. Therefore, in order to maximise the titre obtainable with the LTR1 vector experiments were undertaken to optimise the elements used to drive viral RNA genome transcription.

Figure 5:
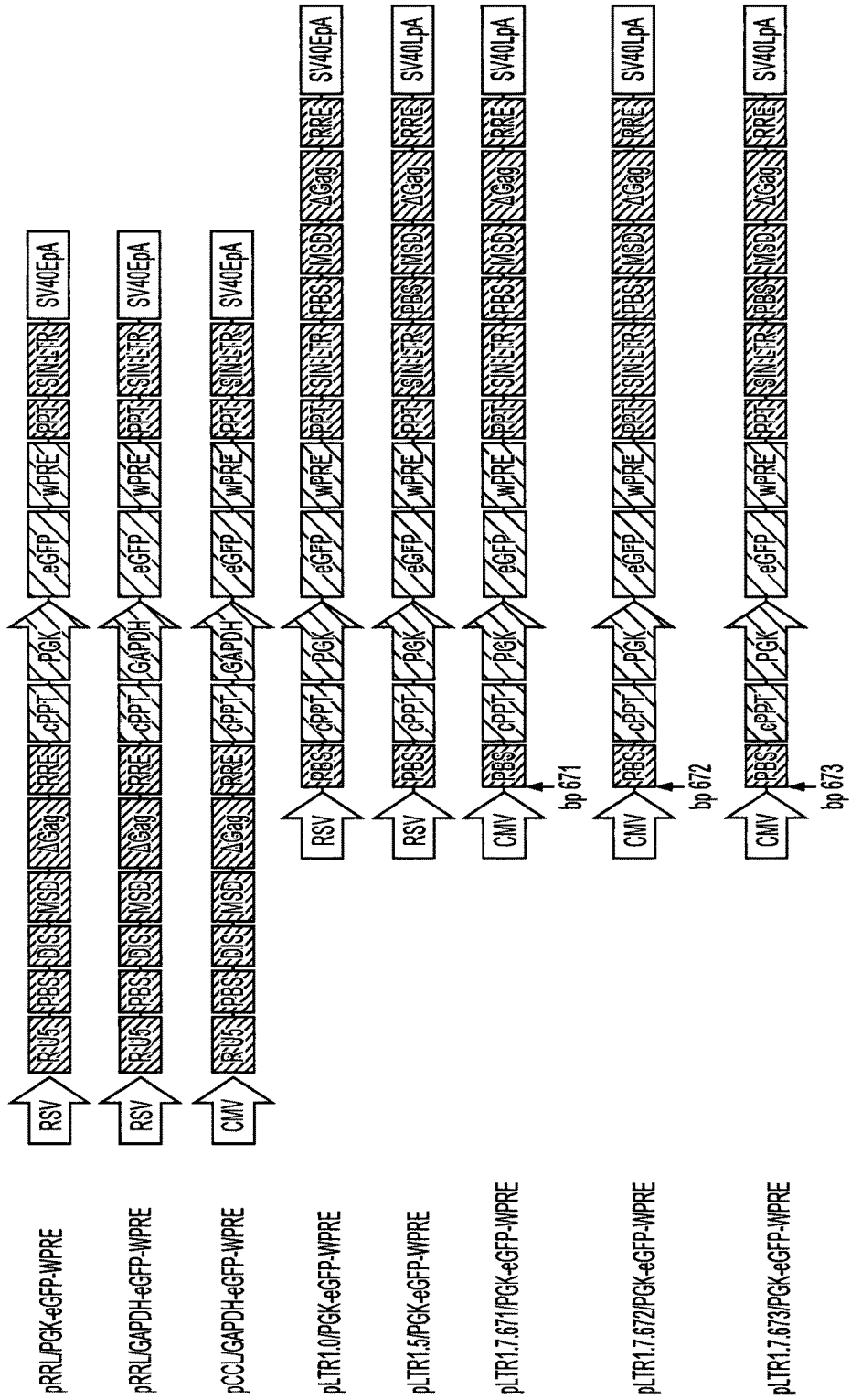
FIG. 5. Maps of vector plasmids described in this invention. SV40EpA, simian virus 40 early polyadenylation signal; SV40LpA, simian virus 40 late polyadenylation signal; DIS, HIV-1 dimerisation signal; pA−, AATAAA to AACAAA mutant polyadenylation signal. AmpR, Ampicillin Resistance gene; ori, bacterial origin of replication.
Figure 5:
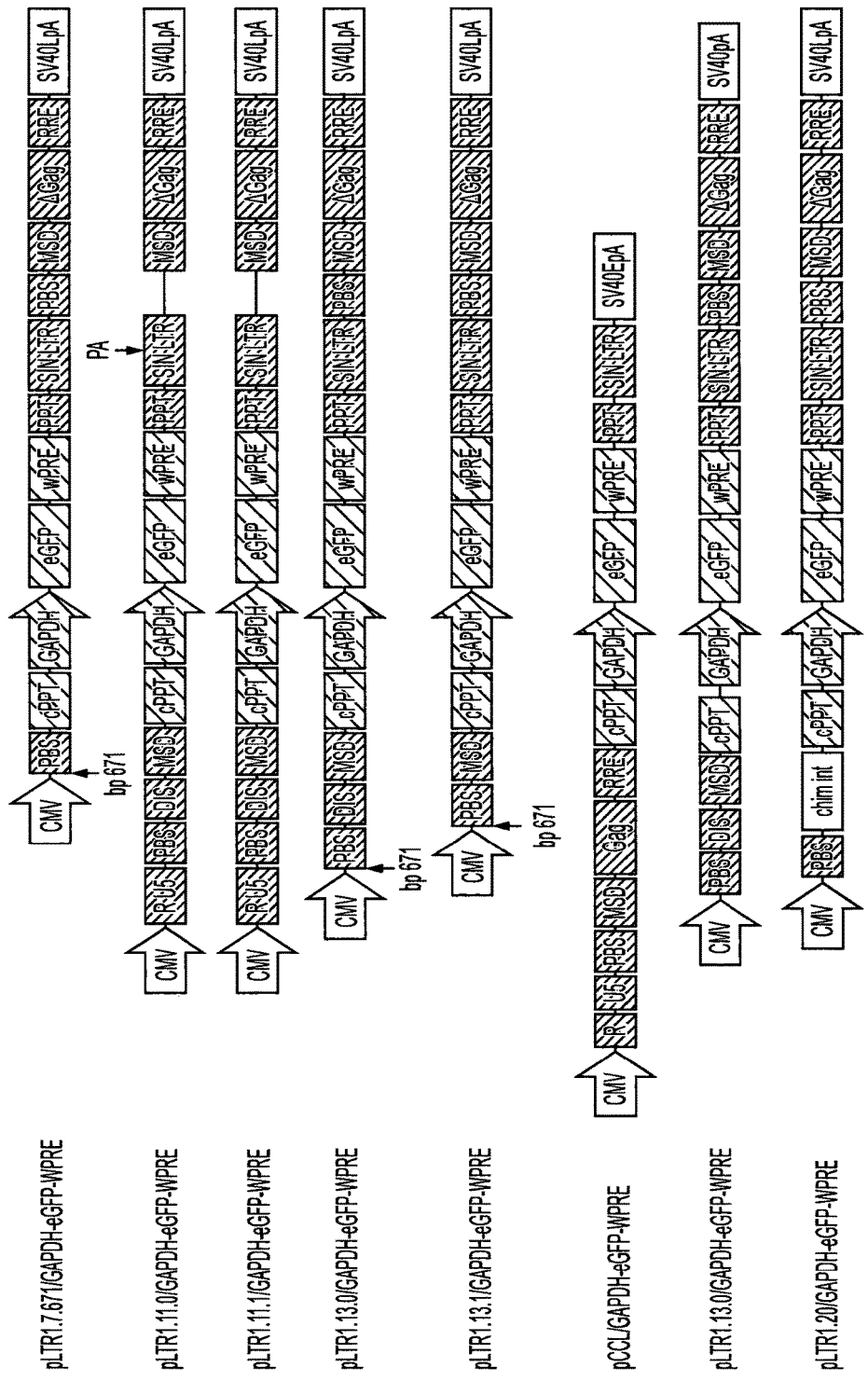

Efficient polyadenylation is associated with higher steady-state levels of RNA polymerase II (Pol II) transcripts, and it has been shown that the simian virus 40 (SV40) late polyadenylation (polyA) signal acts as a stronger polyadenylation signal than the SV40 early polyA signal (32). The inventors therefore generated two LTR1 configurations: LTR1.0/PGK-eGFP-WPRE (LTR1.0/PEW) uses the SV40 early polyA signal present in the parental RRL backbone while LTR1.5/PEW uses an SV40 late polyA signal derived from pCI (FIG. 5). Lentiviral vector was prepared in parallel using these two constructs and a conventional RRL/PEW construct and titred on 293T cells by flow cytometry. The vector titres were calculated as LTR1.0 PEW $2.3 \times 10^4$ transducing units/ml (TU/ml), LTR1.5 PEW $4.5 \times 10^4$ TU/ml, RRL PEW $6.9 \times 10^7$ TU/ml. As the SV40 late polyA signal yielded a higher titre, this element was used in all subsequent LTR1 constructs. Continued eGFP expression 14 days after transduction and following at least four passages of dividing cells suggests that the LTR1 vectors are competent for integrase-mediated chromosomal integration.

High steady-state levels of Pol II transcripts can also be achieved through the use of a strong promoter, so constructs were generated in which the Rous Sarcoma Virus (RSV) promoter derived from the parental RRL backbone was replaced by a human cytomegalovirus immediate early (CMV) promoter derived from a CCL plasmid. In order to optimise the alignment of the CMV promoter and the LTR1 5' PBS, three constructs were generated in which the PBS was positioned precisely on the reported transcription start site for the CMV promoter (33) (LTR1.7.672/PEW), 1 bp upstream (LTR1.7.671/PEW) or 1 bp downstream (LTR1.7.673/PEW). Lentiviral vector was prepared in parallel from these constructs, LTR1.5/PEW and RRL/PEW and titred on 293T cells by flow cytometry. The replacement of the RSV promoter with the CMV promoter resulted in a 25-fold increase in LTR1 vector titre (LTR1.5 PEW $2.3 \times 10^4$ TU/ml, LTR1.7.671 PEW $5.6 \times 10^5$ TU/ml, LTR1.7.672 PEW $5.4 \times 10^5$ TU/ml, LTR1.7.673 PEW $4.7 \times 10^5$ TU/ml, RRL PEW $5.8 \times 10^7$ TU/ml). As the LTR1.7.671 CMV configuration yielded the highest titre, this promoter and alignment were used in subsequent LTR1 constructs.

2.2. Effect of Translation of LTR1 Transfer Vector RNA

Lentiviral RNA genomes acquire a 5' 7-methylguanylate cap (m7G) cap during transcription by PolII and hence are competent for translation by producer cell ribosomes. In the scanning model of translation initiation in mammalian cells, the ribosome loads onto the 5' cap and scans in a 5'-3' direction until it reaches the 5'-most ATG codon, at which point translation can initiate. In RRL and CCL RNA genomes the 5'-most ATG occurs at the start of the truncated Gag element and is followed by a 21 codon open reading frame. In the LTR1 vector configuration, the 5'-most ATG will be found within the transgene expression cassette, probably at a cryptic ATG within the internal promoter.

For example, in the LTR1.7.671 PEW vector the 5'-most ATG occurs close to the middle of the PGK promoter and is in frame with the downstream eGFP coding sequence with no intervening stop codons. Since LTR1.7.671 PEW was found to yield vector titres around $10^2$-fold lower than an RRL PEW vector it was hypothesised that this cryptic translation product might be interfering with virion production in producer cells.

To test this hypothesis the PGK promoter was replaced with the human GAPDH promoter which lacks ATG codons entirely. In LTR1.7.671 GAPDH-eGFP-wPRE (LTR1.7.671 GEW) the 5'-most ATG is at the start of the eGFP open reading frame, so translation of full length vector RNA should produce eGFP only. Lentiviral vector was prepared from RRL PEW, RRL GEW, LTR1.7.671 PEW and LTR1.7.671 GEW and titred on 293T cells by flow cytometry. The resulting titres were RRL PEW $6.4 \times 10^7$ TU/ml, RRL GEW $1.6 \times 10^8$ TU/ml, LTR1.7.671 PEW $7.1 \times 10^5$ TU/ml and LTR1.7.671 GEW $7.6 \times 10^5$ TU/ml. Cryptic translation initiation does not appear to have been the limiting factor in this LTR1 vector preparation, but the GAPDH promoter was used in subsequent constructs as the mean fluorescence intensity indicates that it is a stronger promoter than the PGK promoter so is a better reporter of successful transduction.

2.3. Preventing Cleavage and Polyadenylation within the Internal LTR

The SIN LTR located near the midpoint in the LTR1 vector configuration contains the HIV-1 polyadenylation signal. Although a previous report in which the HIV-1 LTR was relocated to the midpoint of a vector reported efficient full length transcription (8), it was decided to investigate the possibility that polyadenylation within the SIN LTR of an LTR1 vector might be preventing production of full length RNA genomes and hence causing the observed reduction in titre relative to third generation lentiviral configurations.

In order to prevent cleavage and polyadenylation at the LTR polyA signal, the AATAAA motif which binds cleavage and polyadenylation specificity factor (CPSF) was mutated to AACAAA in construct LTR1.11.0 GEW. This mutation was previously reported to abolish cleavage and polyadenylation at the HIV-1 polyA signal (34). As a functional polyA signal is required for reporter gene expression in target cells, a fragment of the HIV-1 genome covering the region from the 5' R to the major splice donor (MSD) stem loop was introduced at the 5' end of this construct and the 3' PBS was deleted. This vector is predicted to initiate minus strand synthesis at the 5' PBS and undergo minus strand transfer and subsequent stages of reverse transcription in the same way as a third generation lentiviral vector so that the 3' mutated polyA signal is replaced by the functional 5' polyA signal. Construct LTR1.11.1 GEW is the same as LTR1.11.0 except that it retains a functional AATAAA motif.

Lentiviral vector prepared from LTR1.11.0 GEW and LTR1.11.1 GEW yielded titres of $2.5 \times 10^8$ TU/ml and $1.7 \times 10^8$ TU/ml respectively compared to a CCL GEW parallel control titre of $1.3 \times 10^9$ TU/ml. This suggests that the midpoint polyA signal is not efficiently used in an LTR1 configuration. It is possible that the MSD located downstream of the LTR is able to block polyadenylation at this site as occurs at the 5' polyA signal in a conventional lentiviral vector (35).

2.4. Effects of Minus Strand Transfer and a 5' Major Splice Donor

The greatly improved titres observed with the LTR1.11 configuration suggested two possible explanations. Firstly, initiation of minus strand synthesis at the 5' PBS and/or minus strand transfer might improve the efficiency of reverse transcription. Secondly, the presence of the MSD at the 5' end of the vector might improve the efficiency of RNA genome transcription. In order to test these hypotheses construct LTR1.13.0 GEW was generated which resembles LTR1.7.671 except that the 5' end of the RNA includes the full HIV-1 genome between the PBS and the MSD stem loop instead of only the 18 bp PBS. In this construct initiation of minus strand DNA synthesis is predicted to take place at the midpoint of the vector. Construct LTR1.13.1 GEW is identical to LTR1.13.0 GEW except that the sequence between the 5' PBS and the MSD stem loop has been deleted.

Lentiviral vector was prepared from LTR1.13.0 GEW, LTR1.13.1 GEW and LTR1.7.671 GEW and titred by flow cytometry. These constructs yielded titres of $2.6 \times 10^8$ TU/ml, $9.2 \times 10^7$ TU/ml and $3.2 \times 10^7$ TU/ml respectively compared to a CCL GEW parallel control titre of $1.3 \times 10^9$ TU/ml. These results suggest that the elimination of minus strand transfer from reverse transcription has no negative impact on viral titre and that the large increase in titre observed with the LTR1.11 configuration was due to the presence of the full sequence between the 5' PBS and the MSD stem loop. It has been previously reported that splice sites close to the promoter activate transcription of mammalian genes (36) and previous attempts to mutate the major splice donor in lentiviral vectors resulted in reduced vector titres (20; 21). Therefore it appears that the presence of splicing factors close to the 5' end of the vector RNA genome is required for the production of higher titre lentiviral vectors in both a conventional and LTR1 configuration.

In order to mimic the transcriptional activating effect of the MSD in LTR-1 vectors while reducing HIV sequence, it was replaced by a chimeric intron from the pCI expression plasmid, inserted between the PBS and cPPT, to produce pLTR1.20/GAPDH-eGFP-WPRE. As the wild-type 5' LTR has been removed from LTR-1 the HIV MSD no longer functions to regulate the production of subgenomic RNAs in this vector and it can be exchanged. The use of the strong heterologous intron from pCI offers advantages over the inclusion of the MSD given that no flanking splice enhancers are required and it also includes a splice acceptor which facilitates its removal from viral RNA in producer cells.

Addition of the pCI chimeric intron in the pLTR1.20/GAPDH-eGFP-WPRE vector led to a 3-fold improvement in titre, as calculated by FACS.

2.5 Full-Length PCR and Sequencing of pLTR1.7.671/GAPDH-eGFP-WPRE Provirus

To demonstrate the structure of reverse transcribed proviral DNA from the pLTR1.7.671/GAPDH-eGFP-WPRE vector, HEK293T cells were transduced at a multiplicity of infection of 10. Genomic DNA was extracted 1 week after transduction. The full-length provirus was amplified by PCR using the oligos designated below to give a 2.1 kb amplicon, which was extracted following separation on a 1% agarose gel and TA-cloned (Lifetechnologies) prior to sequencing.

```
                                              (SEQ ID NO. 1)
    U5 forward:    5' GGTAACTAGAGATCCCTCAGACCC 3'

(SEQ ID NO. 2)
    U3 reverse:    5' CGTTGGGAGTGAATTAGCCCTTCC 3'
```

Sequence analysis showed that the provirus contained the correct 5' and 3' LTRs following reverse transcription, displaying the expected sequence with the gag-RRE region removed, when the provirus was examined.

2.6 Examination of Integrated LTR-1 Provirus Sequences by 'Plasmid Rescue'

In order to stringently investigate the sequences of LTR-1 proviruses and confirm the absence of the deleted HIV-1 packaging sequences, a technique was employed in which the ampicillin resistance marker and bacterial origin of replication were removed from the pLTR1.20 plasmid backbone and inserted within the transgenic region, between the LTRs. This enables pLTR1.20/Amp1R-Ori proviral DNA to be excised from transduced HEK 293T cells, recircularised and transformed into *Escherichia. coli* bacteria which would replicate and form colonies upon uptake of a vector genome containing an ampicillin resistance gene (AmpR) and bacterial origin of replication (ori) between the LTRs. Propagation of proviral sequences in bacteria allows the reverse transcribed sequence to be studied in detail. Sequencing of the proviral DNA rescued in bacteria reads through the LTR and into a region within, host cell chromosomal DNA which was identified by BLAT search. The internal sequence of the provirus confirmed the mechanism of reverse transcription did result in the expected structure as shown in FIG. 4. It was not possible to sequence the RRE element, suggesting that it was absent from the integrated provirus as predicted.

2.7. In Vivo Function of pLTR1.20/SFFV-eGFP-WPRE

To demonstrate LTR-1 vector function in vivo, 1 day old neonatal CD-1 mice were injected intravenously with $4.5 \times 10^5$ vector particles of LTR1.20/SFFV-eGFP-WPRE. Mice were sacrificed and livers were dissected 1 week after vector administration and imaged revealing GFP-positive cells visible in the livers of injected animals demonstrating that LTR-1 is capable of gene deliver to cells in vivo.

3. Discussion

A number of different retroviruses have been developed as retroviral vectors for mammalian gene transfer (1-5). The largest change which takes place during vectorisation of a retrovirus is the separation of viral components into cis elements which must remain present on the nucleic acid being transferred into the target cell and trans elements which need only be provided in producer cells to enable production of infectious particles. Examples of retroviral cis elements include the HIV-1 RNA packaging signal (Ψ) and Rev Response Element (RRE) which must remain covalently attached to the transgene expression cassette in order for it to be packaged into virions, while trans elements include coding sequences for the Gag and Gag-Pol polyproteins and the viral envelope glycoprotein.

As with other retroviral vectors, the cis elements within HIV-1-based lentiviral vectors are located between the viral long terminal repeats (LTRs) so are reverse transcribed and remain associated with the transgene expression cassette within the target cell. The presence of these cis elements within target cell proviruses creates a number of empirically observed and theoretically possible problems for the practical application of lentiviral vectors, particularly for gene therapy. The cis elements contain splice sites able to splice with and dysregulate host genes involved in the control of cell proliferation (14), CpG islands able to undergo DNA methylation (16), large untranscribed regions associated with transcriptional silencing of episomal DNA molecules (17), and RNA packaging signals able to mediate vector remobilisation (15). Lentiviral cis elements also occupy up to 2 kb of the reverse transcript which may reduce the size of transgene expression cassettes which can be delivered with these vectors.

In this report, an approach to eliminating HIV-1-derived cis elements from the DNA delivered to target cells is described. In the novel LTR1 configuration the cis elements are located downstream of the 3' LTR. These elements are therefore present in the viral RNA genome so that it can be packaged into virions, but are outside of the region of the genome that is reverse transcribed and so are not present in the vector DNA in the target cell.

In the first configuration tested, transcription of the LTR1 RNA genome was driven by an RSV promoter and SV40 early polyA signal cassette. This configuration produced functional vector titres 3000-fold lower than a conventional RRL vector. A modified cassette using the CMV promoter and an SV40 late polyadenylation signal improved titres significantly to approximately 100-fold lower than a conventional RRL vector.

By relocating the HIV-1-derived 5' leader sequences the new configuration raised the possibility of aberrant translation products originating from within the transgene cassette. It was suggested that aberrant translation could be reducing the vector titres obtained with these constructs. The inventors addressed this possibility by replacing the PGK promoter which contains a cryptic start codon with a GAPDH promoter which lacks ATG codons. No difference in titre was observed.

Another potential problem for vector titre is the presence of a functional polyadenylation signal within the LTR located near the midpoint of the vector. Termination of transcription at this site would prevent production of full length transfer vector RNA competent for packaging into virions. A point mutation was introduced to the AATAAA hexamer which was previously shown to abolish cleavage and polyadenylation at the HIV-1 polyA signal but observed no increase in titre. The inventors hypothesise that the HIV-1 major splice donor (MSD) located downstream of the LTR in the LTR1 configuration is able to block cleavage and polyadenylation at this site just as it does in wildtype HIV-1 and conventional lentiviral vectors (35).

The inventors then reintroduced sequences between the PBS and the MSD stem loop to the 5' end of the LTR1 genomic RNA and observed a significant increase in titre to within 5-fold of a CCL-based construct. The presence of splicing factors close to the 5' end of the vector genomic RNA appears to aid the production of high titre lentiviral vectors in both the conventional and LTR1 configurations but is not essential (20; 21).

The LTR1 vector configuration described in this report could potentially replace all third generation HIV-1-based lentiviral vectors in the applications in which they are currently used. Furthermore, the mechanism of reverse transcription is highly conserved among retroviruses so an LTR1 configuration could be applied to vectors based on retroviruses other than HIV-1.

REFERENCES (1) Suerth J D, Maetzig T, Galla M, Baum C, Schambach A. Journal of Virology 2010 Jul. 1; 84(13):6626-35.
(2) Hildinger M, Abel K L, Ostertag W, Baum C. Journal of Virology 1999 May 1; 73(5):4083-9.
(3) Zufferey R, Dull T, Mandel R J, Bukovsky A, Quiroz D, Naldini L, et al. Journal of Virology 1998 Dec. 1; 72(12):9873-80.
(4) Jarraya B+, Boulet S, Scott Ralph G, Jan C, Bonvento G, Azzouz M, et al. Science Translational Medicine 2009 Oct. 14; 1(2):2ra4.
(5) Heinkelein M, Dressler M, Jírmy G, Rammling M, Imrich H, Thurow J, et al. Journal of Virology 2002 Apr. 15; 76(8):3774-83.
(6) Burns J C, Friedmann T, Driever W, Burrascano M, Yee J K. Proceedings of the National Academy of Sciences 1993 Sep. 1; 90(17):8033-7.
(7) Malim M H, Hauber J, Le S Y, Maizel J V, Cullen B R. Nature 1989 Mar. 16; 338(6212):254-7.
(8) Cockrell A, van Praag H, Santistevan N, Ma H, Kafri T. Retrovirology 2011; 8(1):51.
(9) Sirven A, Pflumio F, Zennou V, Titeux M, Vainchenker W, Coulombel L, et al. Blood 2000 Dec. 15; 96(13):4103-10.
(10) Higashimoto T, Urbinati F, Perumbeti A, Jiang G, Zarzuela A, Chang L J, et al. Gene Ther 2007 Jun. 28; 14(17):1298-304.
(11) Cesana D, Sgualdino J, Rudilosso L, Merella S, Naldini L, Montini E. J Clin Invest 2012 May 1; 122(5):1667-76.
(12) Moiani A, Paleari Y, Sartori D, Mezzadra R, Miccio A, Cattoglio C, et al. J Clin Invest 2012 May 1; 122(5):1653-66.
(13) Almarza D, Bussadori G, Navarro M, Mavilio F, Larcher F, Murillas R. Gene Ther 2011 July; 18(7):674-81.
(14) Cavazzana-Calvo M, Payen E, Negre O, Wang G, Hehir K, Fusil F, et al. Nature 2010 Sep. 16; 467(7313):318-22.
(15) Hanawa H, Persons D A, Nienhuis A W. Journal of Virology 2005 Jul. 1; 79(13):8410-21.
(16) He J, Yang Q, Chang L J. Journal of Virology 2005 Nov. 1; 79(21):13497-508.
(17) Lu J, Zhang F, Xu S, Fire A Z, Kay M A. Mol Ther 2012 November; 20(11):2111-9.
(18) Kumar M, Keller B, Makalou N, Sutton R E. Hum Gene Ther 2001 Oct. 10; 12(15):1893-905.
(19) Descours B, Cribier A, Chable-Bessia C, Ayinde D, Rice G, Crow Y, et al. Retrovirology 2012 Oct. 23; 9:87. doi: 10.1186/1742-4690-9-87.:87-9.
(20) Cui Y, Iwakuma T, Chang L J. Contributions of Viral Splice Sites and cis-Regulatory Elements to Lentivirus Vector Function. Journal of Virology 1999 Jul. 1; 73(7):6171-6.
(21) Kotsopoulou E, Kim V N, Kingsman A J, Kingsman S M, Mitrophanous K A. Journal of Virology 2000 May 15; 74(10):4839-52.
(22) Koldej R, Anson D. BMC Biotechnology 2009; 9(1):86.
(23) Delviks K A, Pathak V K. Journal of Virology 1999 Oct. 1; 73(10):7923-32.
(24) Srinivasakumar N. Peer J 2013 Jun. 4; 1:e84. doi: 10.7717/peerj.84. Print; %2013.:e84.
(25) Torne-Celer C, Moreau K, Faure C, Verdier G, Ronfort C. Intervirology 2008; 51(6):447-52.
(26) Torne-Celer C, Moreau K, Faure C, Verdier G+, Ronfort C. Arch Virol 2008; 153(12):2233-43.
(27) Luche R M, Enssle J, Kiem H P. Sci Rep 2012 Jun. 1; 2.
(28) Fang Y, Gong X, Xu M, Zeng F, Zhang J. J Gene Med 2013 Feb. 1; 15(2):102-12.
(29) Voronin Y A, Pathak V K. Journal of Virology 2004 May 15; 78(10):5402-13.
(30) Aki T, Yanagisawa S, Akanuma H. Journal of Biochemistry 1997 Aug. 1; 122(2):271-8.
(31) Fuller M, Anson D S. Hum Gene Ther 2001 November; %20; 12(17):2081-93.

(32) Carswell S, Alwine J C. Molecular and Cellular Biology 1989 Oct. 1; 9(10):4248-58.
(33) Isomura H, Stinski M F, Kudoh A, Nakayama S, Murata T, Sato Y, et al. Journal of Virology 2008 Jan. 15; 82(2):849-58.
(34) Perkins K J, Lusic M, Mitar I, Giacca M, Proudfoot N J. Molecular Cell 2008 Jan. 18; 29(1):56-68.
(35) Ashe M P, Pearson L H, Proudfoot N J. EMBO J 1997 Sep. 15; 16(18):5752-63.
(36) Furger A, Binnie J M O, Lee B A, Proudfoot N J. Genes & Development 2002 Nov. 1; 16(21):2792-9.

APPENDIX

Construct Sequences

The constructs have the sequences according to the sequence identifier below. The actual sequence of each construct is provided in the accompanying sequence listing. Features of these constructs are also shown in FIG. 5.

a) pRRL/PGK-eGFP-WPRE -. SEQ ID NO. 3
b) pRRL/GAPDH-eGFP-WPRE -. SEQ ID NO. 4
c) pCCL/GAPDH-eGFP-WPRE -. SEQ ID NO. 5
d) pLTR1.0/PGK-eGFP-WPRE -. SEQ ID NO. 6
e) pLTR1.5/PGK-eGFP-WPRE -. SEQ ID NO. 7
f) pLTR1.7.671/PGK-eGFP-WPRE -. SEQ ID NO. 8
g) pLTR1.7.672/PGK-eGFP-WPRE -. SEQ ID NO. 9
h) pLTR1.7.673/PGK-eGFP-WPRE -. SEQ ID NO. 10
i) pLTR1.7.671/GAPDH-eGFP-WPRE -. SEQ ID NO. 11
j) pLTR1.11.0/GAPDH-eGFP-wPRE -. SEQ ID NO. 12
k) pLTR1.11.1/GAPDH-eGFP-WPRE -. SEQ ID NO. 13
l) pLTR1.13.0/GAPDH-eGFP-WPRE -. SEQ ID NO. 14
m) pLTR1.13.1/GAPDH-eGFP-WPRE -. SEQ ID NO. 15
n) pLTR1.20/GAPDH-eGFP-WPRE -. SEQ ID NO. 16

The invention claimed is:

1. A retroviral vector comprising a primer binding site, a long terminal repeat, a promoter, and an RNA packaging sequence, wherein the RNA packaging sequence is located 3' of the long terminal repeat and no long terminal repeat is located 3' of the RNA packaging sequence such that reverse transcription initiated at the primer binding site does not lead to reverse transcription of the RNA packaging sequence into vector DNA in a target cell, wherein the RNA packaging sequence comprises an RNA packaging signal (Ψ) and a Rev Response Element (RRE).

2. The retroviral vector of claim 1, wherein the long terminal repeat is a self-inactivating (SIN) LTR.

3. The retroviral vector of claim 1, wherein the vector comprises two long terminal repeats and the RNA packaging sequence is located 3' of the 3' long terminal repeat.

4. The retroviral vector of claim 3, wherein both long terminal repeats are self-inactivating (SIN) LTRs.

5. The retroviral vector of claim 1, further comprising a second primer binding site.

6. The retroviral vector of claim 1, wherein the vector further comprises an exogenous nucleotide sequence for delivery into a target cell.

7. The retroviral vector of claim 1, wherein the vector further comprises a 3' polypurine tract (3' PPT).

8. The retroviral vector of claim 1, wherein the vector further comprises a central polypurine tract (cPPT).

9. The retroviral vector of claim 1, wherein the vector further comprises a post-transcriptional regulatory element (PRE).

10. The retroviral vector of claim 1, wherein the vector further comprises a polyadenylation (polyA) signal.

11. The retroviral vector of claim 1, wherein the primer binding site is positioned precisely on the transcription start site for the promoter.

12. The retroviral vector of claim 1, wherein the vector further comprises a major splice donor (MSD) site.

13. A retroviral vector which comprises, in 5' to 3' direction, the following components:

a) 5'-promoter-primer binding site-expressible transgene-LTR-primer binding site-RNA packaging sequence-3'; or b) 5'-promoter-LTR-primer binding site-expressible transgene-LTR-RNA packaging sequence-3'.

14. The vector of claim 1, wherein the A retroviral vector which comprises, in 5' to 3' direction, the following components:

a) 5'-promoter-primer binding site-expressible transgene-PPT-LTR-primer binding site-RNA packaging sequence-polyA signal-3'; or b) 5'-promoter-LTR-primer binding site-expressible transgene-PPT-LTR-RNA packaging sequence-polyA signal-3'.

15. A host cell comprising the vector of claim 1, wherein the host cell is not in a human body.

16. A virion comprising the vector of claim 1.

17. A pharmaceutical composition comprising the vector of claim 1.

18. A method of delivering a gene to a target cell, the method comprising administering an effective amount of a retroviral vector or a virion containing the vector to the target cell, wherein the vector comprises a primer binding site, a long terminal repeat, a promoter, and an RNA packaging sequence, wherein the RNA packaging sequence is located 3' of the long terminal repeat and no long terminal repeat is located 3' of the RNA packaging sequence such that reverse transcription initiated at the primer binding site does not lead to reverse transcription of the RNA packaging sequence into vector DNA in a target cell, wherein the RNA packaging sequence comprises an RNA packaging signal (Ψ) and a Rev Response Element (RRE), and wherein the vector comprises an expressible heterologous gene.

19. The method of claim 18 wherein the target cell is in a subject.

20. A cell containing the expressible heterologous gene delivered by the method of claim 18, wherein the cell is not in a human body.

* * * * *

SEQUENCE LISTING

```
<160> NUMBER OF SEQ ID NOS: 16

<210> SEQ ID NO 1
<211> LENGTH: 24
<212> TYPE: DNA
<213> ORGANISM: Artificial sequence
<220> FEATURE:
<223> OTHER INFORMATION: Oligomer for PCR

<400> SEQUENCE: 1
ggtaactaga gatccctcag accc                                           24

<210> SEQ ID NO 2
<211> LENGTH: 24
<212> TYPE: DNA
<213> ORGANISM: Artificial sequence
<220> FEATURE:
<223> OTHER INFORMATION: Oligomer for PCR

<400> SEQUENCE: 2
cgttgggagt gaattagccc ttcc                                           24

<210> SEQ ID NO 3
<211> LENGTH: 7387
<212> TYPE: DNA
<213> ORGANISM: Artificial sequence
<220> FEATURE:
<223> OTHER INFORMATION: Construct pRRL/PGK-eGFP-WPRE

<400> SEQUENCE: 3
agcttaatgt agtcttatgc aatactcttg tagtcttgca acatggtaac gatgagttag    60
caacatgcct tacaaggaga gaaaaagcac cgtgcatgcc gattggtgga agtaaggtgg   120
tacgatcgtg ccttattagg aaggcaacag acgggtctga catggattgg acgaaccact   180
gaattgccgc attgcagaga tattgtattt aagtgcctag ctcgatacaa taaacgggtc   240
tctctggtta gaccagatct gagcctggga gctctctggc taactaggga acccactgct   300
taagcctcaa taaagcttgc cttgagtgct tcaagtagtg tgtgcccgtc tgttgtgtga   360
```

```
ctctggtaac tagagatccc tcagaccctt ttagtcagtg tggaaaatct ctagcagtgg      420
cgcccgaaca gggacttgaa agcgaaaggg aaaccagagg agctctctcg acgcaggact      480
cggcttgctg aagcgcgcac ggcaagaggc gaggggcggc gactggtgag tacgccaaaa      540
attttgacta gcggaggcta aaggagaga gatgggtgcg agagcgtcag tattaagcgg      600
gggagaatta gatcgcgatg ggaaaaaatt cggttaaggc caggggg aaa gaaaaaatat      660 aaattaaaac atatagtatg ggcaagcagg gagctagaac gattcgcagt taatcctggc      720
ctgttagaaa catcagaagg ctgtagacaa atactgggac agctacaacc atcccttcag      780
acaggatcag aagaacttag atcattatat aatacagtag caaccctcta ttgtgtgcat      840
caaaggatag agataaaaga caccaaggaa gctttagaca agatagagga agagcaaaac      900
aaaagtaaga ccaccgcaca gcaagcggcc gctgatcttc agacctggag gaggagatat      960
gagggacaat tggagaagtg aattatataa atataaagta gtaaaaattg aaccattagg     1020
agtagcaccc accaaggcaa agagaagagt ggtgcagaga gaaaaaagag cagtgggaat     1080
aggagctttg ttccttgggt tcttgggagc agcaggaagc actatgggcg cagcgtcaat     1140
gacgctgacg gtacaggcca gacaattatt gtctggtata gtgcagcagc agaacaattt     1200
gctgagggct attgaggcgc aacagcatct gttgcaactc acagtctggg gcatcaagca     1260
gctccaggca agaatcctgg ctgtggaaag atacctaaag gatcaacagc tcctggggat     1320
ttggggttgc tctggaaaac tcatttgcac cactgctgtg ccttggaatg ctagttggag     1380
taataaatct ctggaacaga tttggaatca cacgacctgg atggagtggg acagagaaat     1440
taacaattac acaagcttaa tacactcctt aattgaagaa tcgcaaaacc agcaagaaaa     1500
gaatgaacaa gaattattgg aattagataa atgggcaagt ttgtggaatt ggtttaacat     1560
aacaaattgg ctgtggtata taaaattatt cataatgata gtaggaggct tggtaggttt     1620
aagaatagtt tttgctgtac tttctatagt gaatagagtt aggcagggat attcaccatt     1680
atcgtttcag acccacctcc caaccccgag gggacccgac aggcccgaag gaatagaaga     1740
agaaggtgga gagagagaca gagacagatc cattcgatta gtgaacggat ctcgacggta     1800
tcggttaact tttaaaagaa aagggggg at tgggggg tac agtgcagggg aaagaatagt     1860
agacataata gcaacagaca tacaaactaa agaattacaa aaacaaatta caaaaattca     1920
aaattttatc gatcacgaga ctagcctcga gaagcttgat atcgaattcc cacggggttg     1980
gggttgcgcc ttttccaagg cagccctggg tttgcgcagg acgcggctg ctctgggcgt     2040 ggttccggga aacgcagcgg cgccgaccct gggtctcgca cattcttcac gtccgttcgc     2100
agcgtcaccc ggatcttcgc cgctacccct tgtgggcccc cggcgacgct tcctgctccg     2160
cccctaagtc gggaaggttc cttgcggttc gcggcgtgcc ggacgtgaca aacggaagcc     2220
gcacgtctca ctagtaccct cgcagacgga cagcgccagg gagcaatggc agcgcgccga     2280
ccgcgatggg ctgtggccaa tagcggctgc tcagcggggc gcgccagag cagcggccgg     2340 gaaggggcgg tgcgggaggc ggggtgtggg gcggtagtgt gggccctgtt cctgcccgcg     2400
cggtgttccg cattctgcaa gcctccggag cgcacgtcgg cagtcggctc cctcgttgac     2460
cgaatcaccg acctctctcc ccagggggat ccaccggtcg ccaccatggt gagcaagggc     2520
gaggagctgt tcaccggggt ggtgcccatc ctggtcgagc tggacggcga cgtaaacggc     2580
cacaagttca gcgtgtccgg cgagggcgag ggcgatgcca cctacggcaa gctgaccctg     2640
aagttcatct gcaccaccgg caagctgccc gtgccctggc ccaccctcgt gaccaccctg     2700
```

```
acctacggcg tgcagtgctt cagccgctac cccgaccaca tgaagcagca cgacttcttc   2760
aagtccgcca tgcccgaagg ctacgtccag gagcgcacca tcttcttcaa ggacgacggc   2820
aactacaaga cccgcgccga ggtgaagttc gagggcgaca ccctggtgaa ccgcatcgag   2880
ctgaagggca tcgacttcaa ggaggacggc aacatcctgg gcacaagct ggagtacaac   2940 tacaacagcc acaacgtcta tatcatggcc gacaagcaga agaacggcat caaggtgaac   3000
ttcaagatcc gccacaacat cgaggacggc agcgtgcagc tcgccgacca ctaccagcag   3060
aacaccccca tcggcgacgg ccccgtgctg ctgcccgaca ccactacct gagcacccag   3120 tccgccctga gcaaagaccc caacgagaag cgcgatcaca tggtcctgct ggagttcgtg   3180
accgccgccg ggatcactct cggcatggac gagctgtaca agtaaagcgg ccgcgtcgac   3240
aatcaacctc tggattacaa atttgtgaa agattgactg gtattcttaa ctatgttgct   3300
ccttttacgc tatgtggata cgctgcttta atgcctttgt atcatgctat gcttcccgt   3360 atggctttca ttttctcctc cttgtataaa tcctggttgc tgtctcttta tgaggagttg   3420
tggcccgttg tcaggcaacg tggcgtggtg tgcactgtgt ttgctgacgc aaccccact   3480 ggttggggca ttgccaccac ctgtcagctc ctttccggga cttccgcttt ccccctccct   3540
attgccacgg cggaactcat cgccgcctgc cttgcccgct gctggacagg ggctcggctg   3600
ttgggcactg acaattccgt ggtgttgtcg gggaagctga cgtccttcc atggctgctc   3660 gcctgtgttg ccacctggat tctgcgcggg acgtccttct gctacgtccc ttcggccctc   3720
aatccagcgg accttccttc ccgcggcctg ctgccggctc tgcggcctct tccgcgtctt   3780
cgccttcgcc ctcagacgag tcggatctcc ctttgggccg cctccccgcc tggaattcga   3840
gctcggtacc tttaagacca atgacttaca aggcagctgt agatcttagc cacttttaa   3900 aagaaaaggg gggactggaa gggctaattc actcccaacg aagacaagat ctgctttttg   3960
cttgtactgg gtctctctgg ttagaccaga tctgagcctg ggagctctct ggctaactag   4020
ggaacccact gcttaagcct caataaagct tgccttgagt gcttcaagta gtgtgtgccc   4080
gtctgttgtg tgactctggt aactagagat ccctcagacc cttttagtca gtgtggaaaa   4140
tctctagcag tagtagttca tgtcatctta ttattcagta tttataactt gcaaagaaat   4200
gaatatcaga gagtgagagg aacttgttta ttgcagctta taatggttac aaataaagca   4260
atagcatcac aaatttcaca aataaagcat tttttcact gcattctagt tgtggtttgt   4320
ccaaactcat caatgtatct tatcatgtct ggctctagct atcccgcccc taactccgcc   4380
cagttccgcc cattctccgc cccatggctg actaatttt tttatttatg cagaggccga   4440
ggccgcctcg gcctctgagc tattccagaa gtagtgagga ggcttttttg gaggcctagg   4500
cttttgcgtc gagacgtacc caattcgccc tatagtgagt cgtattacgc gcgctcactg   4560
gccgtcgttt tacaacgtcg tgactgggaa accctggcg ttacccaact taatcgcctt   4620
gcagcacatc ccccttttcgc cagctggcgt aatagcgaag aggcccgcac cgatcgccct   4680
tcccaacagt tgcgcagcct gaatggcgaa tggcgcgacg cgcccgtag cggcgcatta   4740 agcgcggcgg gtgtggtggt tacgcgcagc gtgaccgcta cacttgccag cgccctagcg   4800
cccgctcctt tcgctttctt cccttccttt ctcgccacgt tcgccggctt tccccgtcaa   4860
gctctaaatc gggggctccc tttagggttc cgatttagtg ctttacggca cctcgacccc   4920
aaaaaacttg attagggtga tggttcacgt agtgggccat cgccctgata gacggttttt   4980
cgccctttga cgttggagtc cacgttcttt aatagtggac tcttgttcca aactggaaca   5040
acactcaacc ctatctcggt ctattctttt gatttataag ggattttgcc gatttcggcc   5100
```

```
tattggttaa aaaatgagct gatttaacaa aaatttaacg cgaattttaa caaaatatta    5160
acgtttacaa tttcccaggt ggcacttttc ggggaaatgt gcgcggaacc cctatttgtt    5220
tattttctta aatacattca aatatgtatc cgctcatgag acaataaccc tgataaatgc    5280
ttcaataata ttgaaaaagg aagagtatga gtattcaaca tttccgtgtc gcccttattc    5340
ccttttttgc ggcattttgc cttcctgttt ttgctcaccc agaaacgctg gtgaaagtaa    5400
aagatgctga agatcagttg ggtgcacgag tgggttacat cgaactggat ctcaacagcg    5460
gtaagatcct tgagagtttt cgccccgaag aacgttttcc aatgatgagc acttttaaag    5520
ttctgctatg tggcgcggta ttatcccgta ttgacgccgg gcaagagcaa ctcggtcgcc    5580
gcatacacta ttctcagaat gacttggttg agtactcacc agtcacagaa aagcatctta    5640
cggatggcat gacagtaaga gaattatgca gtgctgccat aaccatgagt gataacactg    5700
cggccaactt acttctgaca acgatcggag gaccgaagga gctaaccgct tttttgcaca    5760
acatggggga tcatgtaact cgccttgatc gttgggaacc ggagctgaat gaagccatac    5820
caaacgacga gcgtgacacc acgatgcctg tagcaatggc aacaacgttg cgcaaactat    5880
taactggcga actacttact ctagcttccc ggcaacaatt aatagactgg atggaggcgg    5940
ataaagttgc aggaccactt ctgcgctcgg cccttccggc tggctggttt attgctgata    6000
aatctggagc cggtgagcgt gggtctcgcg gtatcattgc agcactgggg ccagatggta    6060
agccctcccg tatcgtagtt atctacacga cggggagtca ggcaactatg gatgaacgaa    6120
atagacagat cgctgagata ggtgcctcac tgattaagca ttggtaactg tcagaccaag    6180
tttactcata tatactttag attgatttaa aacttcattt ttaatttaaa aggatctagg    6240
tgaagatcct ttttgataat ctcatgacca aaatccctta acgtgagttt tcgttccact    6300
gagcgtcaga ccccgtagaa aagatcaaag gatcttcttg agatcctttt tttctgcgcg    6360
taatctgctg cttgcaaaca aaaaaaccac cgctaccagc ggtggtttgt ttgccggatc    6420
aagagctacc aactctttt ccgaaggtaa ctggcttcag cagagcgcag ataccaaata    6480
ctgtccttct agtgtagccg tagttaggcc accacttcaa gaactctgta gcaccgccta    6540
catacctcgc tctgctaatc ctgttaccag tggctgctgc cagtggcgat aagtcgtgtc    6600
ttaccgggtt ggactcaaga cgatagttac cggataaggc gcagcggtcg ggctgaacgg    6660
ggggttcgtg cacacagccc agcttggagc gaacgaccta ccgaactg agataccta    6720 agcgtgagct atgagaaagc gccacgcttc ccgaagggag aaaggcggac aggtatccgg    6780
taagcggcag ggtcggaaca ggagagcgca cgagggagct tccaggggga aacgcctggt    6840
atctttatag tcctgtcggg tttcgccacc tctgacttga gcgtcgattt ttgtgatgct    6900
cgtcaggggg gcggagccta tggaaaaacg ccagcaacgc ggccttttta cggttcctgg    6960
ccttttgctg gccttttgct cacatgttct ttcctgcgtt atcccctgat tctgtggata    7020
accgtattac cgcctttgag tgagctgata ccgctcgccg cagccgaacg accgagcgca    7080
gcgagtcagt gagcgaggaa gcggaagagc gcccaatacg caaaccgcct ctccccgcgc    7140
gttggccgat tcattaatgc agctggcacg acaggtttcc cgactggaaa gcgggcagtg    7200
agcgcaacgc aattaatgtg agttagctca ctcattaggc accccaggct ttacacttta    7260
tgcttccggc tcgtatgttg tgtggaattg tgagcggata acaatttcac acaggaaaca    7320
gctatgacca tgattacgcc aagcgcgcaa ttaaccctca ctaaagggaa caaaagctgg    7380
agctgca                                                              7387
```

<210> SEQ ID NO 4
<211> LENGTH: 7354
<212> TYPE: DNA
<213> ORGANISM: Artificial sequence
<220> FEATURE:
<223> OTHER INFORMATION: Construct pRRL/GAPDH-eGFP-WPRE

<400> SEQUENCE: 4

```
agcttaatgt agtcttatgc aatactcttg tagtcttgca acatggtaac gatgagttag      60
caacatgcct tacaaggaga gaaaaagcac cgtgcatgcc gattggtgga agtaaggtgg     120
tacgatcgtg ccttattagg aaggcaacag acgggtctga catggattgg acgaaccact     180
gaattgccgc attgcagaga tattgtattt aagtgcctag ctcgatacaa taaacgggtc     240
tctctggtta gaccagatct gagcctggga gctctctggc taactaggga acccactgct     300
taagcctcaa taaagcttgc cttgagtgct tcaagtagtg tgtgcccgtc tgttgtgtga     360
ctctggtaac tagagatccc tcagaccctt ttagtcagtg tggaaaatct ctagcagtgg     420
cgcccgaaca gggacttgaa agcgaaaggg aaaccgagag agctctctcg acgcaggact     480
cggcttgctg aagcgcgcac ggcaagaggc gaggggcggc gactggtgag tacgccaaaa     540
attttgacta gcggaggcta aaggagaga atggggtgcg agagcgtcag tattaagcgg     600
gggagaatta gatcgcgatg ggaaaaaatt cggttaaggc caggggaaa gaaaaaatat     660
aaattaaaac atatagtatg ggcaagcagg gagctagaac gattcgcagt taatcctggc     720
ctgttagaaa catcagaagg ctgtagacaa atactgggac agctacaacc atcccttcag     780
acaggatcag aagaacttag atcattata atacagtag caaccctcta ttgtgtgcat     840
caaaggatag agataaaaga caccaaggaa gctttagaca agatagagga agagcaaaac     900
aaaagtaaga ccaccgcaca gcaagcggcc gctgatcttc agacctggag gaggagatat     960
gagggacaat tggagaagtg aattatataa atataaagta gtaaaattg aaccattagg    1020
agtagcaccc accaaggcaa agagaagagt ggtgcagaga gaaaaaagag cagtgggaat    1080
aggagctttg ttccttgggt tcttgggagc agcaggaagc actatgggcg cagcgtcaat    1140
gacgctgacg gtacaggcca gacaattatt gtctggtata gtgcagcagc agaacaattt    1200
gctgagggct attgaggcgc aacagcatct gttgcaactc acagtctggg gcatcaagca    1260
gctccaggca agaatcctgg ctgtggaaag atacctaaag gatcaacagc tcctggggat    1320
ttggggttgc tctggaaaac tcatttgcac cactgctgtg ccttggaatg ctagttggag    1380
taataaatct ctggaacaga tttggaatca cacgacctgg atggagtggg acagagaaat    1440
taacaattac acaagcttaa tacactcctt aattgaagaa tcgcaaaacc agcaagaaaa    1500
gaatgaacaa gaattattgg aattagataa atgggcaagt ttgtggaatt ggtttaacat    1560
aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag gaatagaaga    1740
agaaggtgga gagagagaca gagacagatc cattcgatta gtgaacggat ctcgacggta    1800
tcggttaact tttaaaagaa aagggggat tggggggtac agtgcagggg aaagaatagt    1860
agacataata gcaacagaca tacaaactaa agaattacaa aaacaaatta caaaaattca    1920
aaattttatc gatcacgaga ctagcctcga ggatatcagt tcccaacttt cccgcctct    1980
cagcctttga agaaagaaa ggggaggggg caggccgcgt gcagccgcga gcggtgctgg    2040
gctccggctc caattcccca tctcagtcgt tcccaaagtc ctcctgtttc atccaagcgt    2100
```

```
gtaagggtcc ccgtccttga ctccctagtg tcctgctgcc cacagtccag tcctgggaac    2160
cagcaccgat cacctcccat cgggccaatc tcagtccctt ccccctacg tcggggccca      2220 cacgctcggt gcgtgcccag ttgaaccagg cggctgcgga aaaaaaaag cggggagaaa      2280 gtagggcccg gctactagcg gttttacggg cgcacgtagc tcaggcctca agaccttggg    2340
ctgggactgg ctgagcctgg cgggaggcgg ggtccgagtc accgcctgcc gccgcgcccc    2400
cggtttctat aaattgagcc cgcagcctcc cgcttcgctc tctgctcctc ctgggatcca    2460
ccggtcgcca ccatggtgag caagggcgag gagctgttca ccggggtggt gcccatcctg    2520
gtcgagctgg acggcgacgt aaacggccac aagttcagcg tgtccggcga gggcgagggc    2580
gatgccacct acggcaagct gaccctgaag ttcatctgca ccaccggcaa gctgcccgtg    2640
ccctggccca ccctcgtgac caccctgacc tacggcgtgc agtgcttcag ccgctacccc    2700
gaccacatga agcagcacga cttcttcaag tccgccatgc ccgaaggcta cgtccaggag    2760
cgcaccatct tcttcaagga cgacggcaac tacaagaccc gcgccgaggt gaagttcgag    2820
ggcgacaccc tggtgaaccg catcgagctg aagggcatcg acttcaagga ggacggcaac    2880
atcctggggc acaagctgga gtacaactac aacagccaca acgtctatat catggccgac    2940
aagcagaaga acggcatcaa ggtgaacttc aagatccgcc acaacatcga ggacggcagc    3000
gtgcagctcg ccgaccacta ccagcagaac ccccatcg cgacggccc cgtgctgctg       3060 cccgacaacc actacctgag cacccagtcc gccctgagca agaccccaa cgagaagcgc     3120 gatcacatgg tcctgctgga gttcgtgacc gccgccggga tcactctcgg catggacgag    3180
ctgtacaagt aaagcggccg cgtcgacaat caacctctgg attacaaaat ttgtgaaaga    3240
ttgactggta ttcttaacta tgttgctcct tttacgctat gtggatacgc tgctttaatg    3300
cctttgtatc atgctattgc ttcccgtatg gctttcattt tctcctcctt gtataaatcc    3360
tggttgctgt ctctttatga ggagttgtgg cccgttgtca ggcaacgtgg cgtggtgtgc    3420
actgtgtttg ctgacgcaac cccactggt tgggcattg ccaccactg tcagctcctt      3480 tccgggactt tcgctttccc cctccctatt gccacggcgg aactcatcgc cgcctgcctt    3540
gcccgctgct ggacaggggc tcggctgttg gcactgaca attccgtggt gttgtcgggg     3600
aagctgacgt cctttccatg gctgctcgcc tgtgttgcca cctggattct gcgcgggacg    3660
tccttctgct acgtccctc ggccctcaat ccagcggacc ttccttcccg cggcctgctg     3720
ccggctctgc ggcctcttcc gcgtcttcgc cttcgccctc agacgagtcg gatctccctt    3780
tgggccgcct ccccgcctgg aattcgagct cggtaccttt aagaccaatg acttacaagg    3840
cagctgtaga tcttagccac ttttaaaag aaaaggggg actggaaggg ctaattcact       3900
cccaacgaag acaagatctg ctttttgctt gtactgggtc tctctggtta gaccagatct    3960
gagcctggga gctctctggc taactaggga acccactgct taagcctcaa taaagcttgc    4020
cttgagtgct tcaagtagtg tgtgcccgtc tgttgtgtga ctctggtaac tagagatccc    4080
tcagaccctt ttagtcagtg tggaaaatct ctagcagtag tagttcatgt catcttatta    4140
ttcagtattt taacttgca aagaaatgaa tatcagagag tgagaggaac ttgtttattg      4200
cagcttataa tggttacaaa taagcaata gcatcacaaa tttcacaaat aaagcatttt     4260
tttcactgca ttctagttgt ggtttgtcca aactcatcaa tgtatcttat catgtctggc    4320
tctagctatc ccgcccctaa ctccgcccag ttccgcccat tctccgcccc atggctgact    4380
aatttttttt atttatgcag aggccgaggc cgcctcggcc tctgagctat tccagaagta    4440
```

```
gtgaggaggc ttttttggag gcctaggctt ttgcgtcgag acgtacccaa ttcgccctat    4500
agtgagtcgt attacgcgcg ctcactggcc gtcgttttac aacgtcgtga ctgggaaaac    4560
cctggcgtta cccaacttaa tcgccttgca gcacatcccc ctttcgccag ctggcgtaat    4620
agcgaagagg cccgcaccga tcgcccttcc aacagttgcg cagcctgaat ggcgaatgg     4680 cgcgacgcgc cctgtagcgg cgcattaagc gcggcgggtg tggtggttac gcgcagcgtg    4740
accgctacac ttgccagcgc cctagcgccc gctcctttcg ctttcttccc ttcctttctc    4800
gccacgttcg ccggctttcc ccgtcaagct ctaaatcggg ggctcccttt agggttccga    4860
tttagtgctt tacggcacct cgaccccaaa aaacttgatt agggtgatgg ttcacgtagt    4920
gggccatcgc cctgatagac ggttttttcgc cctttgacgt tggagtccac gttctttaat    4980
agtggactct tgttccaaac tggaacaaca ctcaacccta tctcggtcta ttcttttgat    5040
ttataaggga ttttgccgat ttcggcctat tggttaaaaa atgagctgat ttaacaaaaa    5100
tttaacgcga atttttaacaa aatattaacg tttacaattt cccaggtggc acttttcggg    5160
gaaatgtgcg cggaacccct atttgtttat ttttctaaat acattcaaat atgtatccgc    5220
tcatgagaca ataaccctga taaatgcttc aataatattg aaaaaggaag agtatgagta    5280
ttcaacattt ccgtgtcgcc cttattccct tttttgcggc attttgcctt cctgtttttg    5340
ctcacccaga aacgctggtg aaagtaaaag atgctgaaga tcagttgggt gcacgagtgg    5400
gttacatcga actggatctc aacagcggta agatccttga gttttcgc cccgaagaac     5460 gttttccaat gatgagcact tttaaagttc tgctatgtgg cgcggtatta cccgtattg    5520 acgccgggca agagcaactc ggtcgccgca tacactattc tcagaatgac ttggttgagt    5580
actcaccagt cacagaaaag catcttacgg atggcatgac agtaagagaa ttatgcagtg    5640
ctgccataac catgagtgat aacactgcgg ccaacttact tctgacaacg atcggaggac    5700
cgaaggagct aaccgctttt ttgcacaaca tgggggatca tgtaactcgc cttgatcgtt    5760
gggaaccgga gctgaatgaa gccataccaa acgacgagcg tgacaccacg atgcctgtag    5820
caatggcaac aacgttgcgc aaactattaa ctggcgaact acttactcta gcttcccggc    5880
aacaattaat agactggatg gaggcggata aagttgcagg accacttctg cgctcggccc    5940
ttccggctgg ctggtttatt gctgataaat ctggagccgg tgagcgtggg tctcgcggta    6000
tcattgcagc actggggcca gatggtaagc cctcccgtat cgtagttatc tacacgacgg    6060
ggagtcaggc aactatggat gaacgaaata gacagatcgc tgagataggt gcctcactga    6120
ttaagcattg gtaactgtca gaccaagttt actcatatat actttagatt gatttaaaac    6180 ttcatttta atttaaaagg atctaggtga agatcctttt tgataatctc atgaccaaaa    6240
tcccttaacg tgagttttcg ttccactgag cgtcagaccc cgtagaaaag atcaaaggat    6300
cttcttgaga tccttttttt ctgcgcgtaa tctgctgctt gcaaacaaaa aaaccaccgc    6360
taccagcggt ggtttgtttg ccggatcaag agctaccaac tctttttccg aaggtaactg    6420
gcttcagcag agcgcagata ccaaatactg tccttctagt gtagccgtag ttaggccacc    6480
acttcaagaa ctctgtagca ccgcctacat acctcgctct gctaatcctg ttaccagtgg    6540
ctgctgccag tggcgataag tcgtgtctta ccgggttgga ctcaagacga tagttaccgg    6600
ataaggcgca gcggtcgggc tgaacggggg gttcgtgcac acagcccagc ttggagcgaa    6660
cgacctacac cgaactgaga tacctacagc gtgagctatg agaaagcgcc acgcttcccg    6720
aagggagaaa ggcggacagg tatccggtaa gcggcagggt cggaacagga gagcgcacga    6780
gggagcttcc agggggaaac gcctggtatc tttatagtcc tgtcgggttt cgccacctct    6840
```

```
gacttgagcg tcgattttg tgatgctcgt cagggggcg gagcctatgg aaaaacgcca    6900
gcaacgcggc cttttacgg ttcctggcct tttgctggcc ttttgctcac atgttctttc    6960
ctgcgttatc ccctgattct gtggataacc gtattaccgc ctttgagtga gctgataccg    7020
ctcgccgcag ccgaacgacc gagcgcagcg agtcagtgag cgaggaagcg gaagagcgcc    7080
caatacgcaa accgcctctc cccgcgcgtt ggccgattca ttaatgcagc tggcacgaca    7140
ggtttcccga ctggaaagcg ggcagtgagc gcaacgcaat taatgtgagt tagctcactc    7200
attaggcacc ccaggcttta cactttatgc ttccggctcg tatgttgtgt ggaattgtga    7260
gcggataaca atttcacaca ggaaacagct atgaccatga ttacgccaag cgcgcaatta    7320
accctcacta agggaacaa aagctggagc tgca                                7354
```

<210> SEQ ID NO 5  
<211> LENGTH: 7810  
<212> TYPE: DNA  
<213> ORGANISM: Artificial sequence  
<220> FEATURE:  
<223> OTHER INFORMATION: Construct pCCL/GAPDH-eGFP-WPRE

<400> SEQUENCE: 5

```
ccattgcata cgttgtatcc atatcataat atgtacattt atattggctc atgtccaaca     60
ttaccgccat gttgacattg attattgact agttattaat agtaatcaat tacgggtca    120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc ggggtctctc tggttagacc agatctgagc ctgggagctc tctggctaac    720
tagggaaccc actgcttaag cctcaataaa gcttgccttg agtgcttcaa gtagtgtgtg    780
cccgtctgtt gtgtgactct ggtaactaga tccctcag acccttttag tcagtgtgga    840
aaatctctag cagtggcgcc cgaacaggga cttgaaagcg aaagggaaac cagaggagct    900
ctctcgacgc aggactcggc ttgctgaagc gcgcacggca agaggcgagg ggcggcgact    960
ggtgagtacg ccaaaaattt tgactagcgg aggctagaag gagagagatg ggtgcgagag   1020
cgtcagtatt aagcggggga gaattagatc gcgatgggaa aaaattcggt taaggccagg   1080
gggaaagaaa aaatataaat taaaacatat agtatgggca agcagggagc tagaacgatt   1140
cgcagttaat cctggcctgt tagaaacatc agaaggctgt agacaaatac tgggacagct   1200
acaaccatcc cttcagacag gatcagaaga acttagatca ttatataata cagtagcaac   1260
cctctattgt gtgcatcaaa ggatagagat aaaagacacc aaggaagctt tagacaagat   1320
agaggaagag caaaacaaaa gtaagaccac cgcacagcaa gcggccgctg atcttcagac   1380
ctggaggagg agatatgagg gacaattgga gaagtgaatt atataaatat aaagtagtaa   1440
aaattgaacc attaggagta gcacccacca aggcaaagag aagagtggtg cagagagaaa   1500
```

```
aaagagcagt gggaatagga gctttgttcc ttgggttctt gggagcagca ggaagcacta   1560
tgggcgcagc gtcaatgacg ctgacggtac aggccagaca attattgtct ggtatagtgc   1620
agcagcagaa caatttgctg agggctattg aggcgcaaca gcatctgttg caactcacag   1680
tctggggcat caagcagctc caggcaagaa tcctggctgt ggaaagatac ctaaaggatc   1740
aacagctcct ggggatttgg ggttgctctg gaaaactcat ttgcaccact gctgtgcctt   1800
ggaatgctag ttggagtaat aaatctctgg aacagatttg gaatcacacg acctggatgg   1860
agtgggacag agaaattaac aattacacaa gcttaataca ctccttaatt gaagaatcgc   1920
aaaaccagca agaaaagaat gaacaagaat tattggaatt agataaatgg gcaagtttgt   1980
ggaattggtt taacataaca aattggctgt ggtatataaa attattcata atgatagtag   2040
gaggcttggt aggtttaaga atagttttgc tgtactttc tatagtgaat agagttaggc   2100
agggatattc accattatcg tttcagaccc acctcccaac cccgagggga cccgacaggc   2160
ccgaaggaat agaagaagaa ggtggagaga gagacagaga cagatccatt cgattagtga   2220
acggatctcg acggtatcgg ttaacttta aagaaaagg ggggattggg gggtacagtg   2280
caggggaaag aatagtagac ataatagcaa cagacataca aactaaagaa ttacaaaaac   2340
aaattacaaa aattcaaaat tttatcgatc acgagactag cctcgaggat atcagttccc   2400
caactttccc gcctctcagc ctttgaaaga agaaagggg aggggcagg ccgcgtgcag   2460
ccgcgagcgg tgctgggctc cggctccaat tccccatctc agtcgttccc aaagtcctcc   2520
tgtttcatcc aagcgtgtaa gggtccccgt ccttgactcc ctagtgtcct gctgcccaca   2580
gtccagtcct gggaaccagc accgatcacc tcccatcggg ccaatctcag tcccttcccc   2640
cctacgtcgg ggcccacacg ctcggtgcgt gcccagttga accaggcggc tgcggaaaaa   2700
aaaaagcggg gagaaagtag ggcccggcta ctagcggttt tacggcgcca cgtagctcag   2760
gcctcaagac cttgggctgg gactggctga gcctggcggg aggcggggtc cgagtcaccg   2820
cctgccgccg cgccccggt ttctataaat tgagcccgca gcctcccgct cgctctctg   2880
ctcctcctgg gatccaccgg tcgccaccat ggtgagcaag ggcgaggagc tgttcaccgg   2940
ggtggtgccc atcctggtcg agctggacgg cgacgtaaac ggccacaagt tcagcgtgtc   3000
cggcgagggc gagggcgatg ccacctacgg caagctgacc ctgaagttca tctgcaccac   3060
cggcaagctg cccgtgccct ggcccaccct cgtgaccacc ctgacctacg gcgtgcagtg   3120
cttcagccgc taccccgacc acatgaagca gcacgacttc ttcaagtccg ccatgcccga   3180
aggctacgtc caggagcgca ccatcttctt caaggacgac ggcaactaca agacccgcgc   3240
cgaggtgaag ttcgagggcg acaccctggt gaaccgcatc gagctgaagg gcatcgactt   3300
caaggaggac ggcaacatcc tggggcacaa gctggagtac aactacaaca gccacaacgt   3360
ctatatcatg gccgacaagc agaagaacgg catcaaggtg aacttcaaga tccgccacaa   3420
catcgaggac ggcagcgtgc agctcgccga ccactaccag cagaacaccc ccatcggcga   3480
cggccccgtg ctgctgcccg acaaccacta cctgagcacc cagtccgccc tgagcaaaga   3540
ccccaacgag aagcgcgatc acatggtcct gctggagttc gtgaccgccg ccgggatcac   3600
tctcggcatg gacgagctgt acaagtaaag cggccgcgtc gacaatcaac ctctggatta   3660
caaaatttgt gaaagattga ctggtattct taactatgtt gctccttta cgctatgtgg   3720
atacgctgct ttaatgcctt tgtatcatgc tattgcttcc cgtatggctt tcattttctc   3780
ctccttgtat aaatcctggt tgctgtctct ttatgaggag ttgtggcccg ttgtcaggca   3840
acgtggcgtg gtgtgcactg tgtttgctga cgcaaccccc actggttggg gcattgccac   3900
```

```
cacctgtcag ctcctttccg ggactttcgc tttcccctc cctattgcca cggcggaact    3960
catcgccgcc tgccttgccc gctgctggac aggggctcgg ctgttgggca ctgacaattc    4020
cgtggtgttg tcggggaagc tgacgtcctt tccatggctg ctcgcctgtg ttgccacctg    4080
gattctgcgc gggacgtcct tctgctacgt cccttcggcc ctcaatccag cggaccttcc    4140
ttcccgcggc ctgctgccgg ctctgcggcc tcttccgcgt cttcgccttc gccctcagac    4200
gagtcggatc tcccttgggg ccgcctcccc gcctggaatt cgagctcggt acctttaaga    4260
ccaatgactt acaaggcagc tgtagatctt agccactttt taaaagaaaa gggggactg    4320
gaagggctaa ttcactccca acgaagacaa gatctgcttt tgcttgtac tgggtctctc    4380
tggttagacc agatctgagc ctgggagctc tctggctaac tagggaaccc actgcttaag    4440
cctcaataaa gcttgccttg agtgcttcaa gtagtgtgtg cccgtctgtt gtgtgactct    4500
ggtaactaga gatccctcag accctttag tcagtgtgga aaatctctag cagtagtagt    4560
tcatgtcatc ttattattca gtatttataa cttgcaaaga aatgaatatc agagagtgag    4620
aggaacttgt ttattgcagc ttataatggt tacaaataaa gcaatagcat cacaaatttc    4680
acaaataaag cattttttc actgcattct agttgtggtt tgtccaaact catcaatgta    4740
tcttatcatg tctggctcta gctatcccgc ccctaactcc gcccatcccg ccctaactc    4800
cgcccagttc cgcccattct ccgccccatg gctgactaat ttttttatt tatgcagagg    4860
ccgaggccgc ctcggcctct gagctattcc agaagtagtg aggaggcttt tttggaggcc    4920
tagggacgta cccaattcgc cctatagtga gtcgtattac gcgcgctcac tggccgtcgt    4980
tttacaacgt cgtgactggg aaaaccctgg cgttacccaa cttaatcgcc ttgcagcaca    5040
tccccctttc gccagctggc gtaatagcga agaggcccgc accgatcgcc cttcccaaca    5100
gttgcgcagc ctgaatggcg aatgggacgc gccctgtagc ggcgcattaa gcgcggcggg    5160
tgtggtggtt acgcgcagcg tgaccgctac acttgccagc gccctagcgc ccgctccttt    5220
cgctttcttc ccttcctttc tcgccacgtt cgccggcttt cccgtcaag ctctaaatcg    5280
gggctccct ttagggttcc gatttagtgc tttacggcac ctcgacccca aaaaacttga    5340
ttagggtgat ggttcacgta gtgggccatc gccctgatag acggttttc gccctttgac    5400
gttggagtcc acgttcttta atagtggact cttgttccaa actggaacaa cactcaaccc    5460
tatctcggtc tattcttttg atttataagg gattttgccg atttcggcct attggttaaa    5520
aaatgagctg atttaacaaa aatttaacgc gaattttaac aaaatattaa cgcttacaat    5580
ttaggtggca cttttcgggg aaatgtgcgc ggaaccccta tttgtttatt tttctaaata    5640
cattcaaata tgtatccgct catgagacaa taaccctgat aaatgcttca ataatagcac    5700
ctagatcaag agacaggatg aggatcgttt cgcatgattg aacaagatgg attgcacgca    5760
ggttctccgg ccgcttgggt ggagaggcta ttcggctatg actgggcaca acagacaatc    5820
ggctgctctg atgccgccgt gttccggctg tcagcgcagg ggcgcccggt tctttttgtc    5880
aagaccgacc tgtccggtgc cctgaatgaa ctgcaagacg aggcagcgcg gctatcgtgg    5940
ctggccacga cgggcgttcc ttgcgcagct gtgctcgacg ttgtcactga agcgggaagg    6000
gactggctgc tattgggcga agtgccgggg caggatctcc tgtcatctca ccttgctcct    6060
gccgagaaag tatccatcat ggctgatgca atgcggcggc tgcatacgct tgatccggct    6120
acctgcccat tcgaccacca agcgaaacat cgcatcgagc gagcacgtac tcggatggaa    6180
gccggtcttg tcgatcagga tgatctggac gaagagcatc aggggctcgc gccagccgaa    6240
```

```
ctgttcgcca ggctcaaggc gagcatgccc gacggcgagg atctcgtcgt gacccatggc    6300
gatgcctgct tgccgaatat catggtggaa aatggccgct tttctggatt catcgactgt    6360
ggccggctgg gtgtggcgga ccgctatcag gacatagcgt tggctacccg tgatattgct    6420
gaagagcttg gcggcgaatg ggctgaccgc ttcctcgtgc tttacggtat cgccgctccc    6480
gattcgcagc gcatcgcctt ctatcgcctt cttgacgagt tcttctgaat tattaacgct    6540
tacaatttcc tgatgcggta ttttctcctt acgcatctgt gcggtatttc acaccgcatc    6600
aggtggcact tttcggggaa atgtgcgcgg aaccccctat tgtttatttt tctaaataca    6660
ttcaaatatg tatccgctca tgaccaaaat cccttaacgt gagttttcgt tccactgagc    6720
gtcagacccc gtagaaaaga tcaaaggatc ttcttgagat cctttttttc tgcgcgtaat    6780
ctgctgcttg caaacaaaaa aaccaccgct accagcggtg gtttgtttgc cggatcaaga    6840
gctaccaact ctttttccga aggtaactgg cttcagcaga gcgcagatac caaatactgt    6900
tcttctagtg tagccgtagt taggccacca cttcaagaac tctgtagcac cgcctacata    6960
cctcgctctg ctaatcctgt taccagtggc tgctgccagt ggcgataagt cgtgtcttac    7020
cgggttggac tcaagacgat agttaccgga taaggcgcag cggtcgggct gaacggggggg    7080 gtcgtgcaca gcccagct tggagcgaac gacctacacc gaactgagat acctacagcg    7140
tgagctatga gaaagcgcca cgcttcccga agggagaaag gcggacaggt atccggtaag    7200
cggcagggtc ggaacaggag agcgcacgag ggagcttcca gggggaaacg cctggtatct    7260
ttatagtcct gtcgggtttc gccacctctg acttgagcgt cgatttttgt gatgctcgtc    7320
aggggggcgg agcctatgga aaaacgccag caacgcggcc ttttacggtt cctggccctt    7380
ttgctggcct tttgctcaca tgttctttcc tgcgttatcc cctgattctg tggataaccg    7440
tattaccgcc tttgagtgag ctgataccgc tcgccgcagc cgaacgaccg agcgcagcga    7500
gtcagtgagc gaggaagcgg aagagcgccc aatacgcaaa ccgcctctcc ccgcgcgttg    7560
gccgattcat taatgcagct ggcacgacag gtttcccgac tggaaagcgg gcagtgagcg    7620
caacgcaatt aatgtgagtt agctcactca ttaggcaccc caggctttac actttatgct    7680
tccggctcgt atgttgtgtg gaattgtgag cggataacaa tttcacacag gaaacagcta    7740
tgaccatgat tacgccaagc gcgcaattaa ccctcactaa agggaacaaa agctggagct    7800
gcaagcttgg                                                           7810
```

<210> SEQ ID NO 6
<211> LENGTH: 7245
<212> TYPE: DNA
<213> ORGANISM: Artificial sequence
<220> FEATURE:
<223> OTHER INFORMATION: Construct pLTR1.0/PGK-eGFP-WPRE

<400> SEQUENCE: 6

```
agcttaatgt agtcttatgc aatactcttg tagtcttgca acatggtaac gatgagttag      60
caacatgcct tacaaggaga gaaaaagcac cgtgcatgcc gattggtgga agtaaggtgg     120
tacgatcgtg ccttattagg aaggcaacag acgggtctga catggattgg acgaaccact     180
gaattgccgc attgcagaga tattgtattt aagtgcctag ctcgatacaa taaacgtggc     240
gcccgaacag ggactcgacg gtatcggtta acttttaaaa gaaaaggggg gattgggggg     300
tacagtgcag gggaaagaat agtagacata atagcaacag acatacaaac taaagaatta     360
caaaaacaaa ttacaaaaat tcaaaatttt atcgatcacg agactagcct cgagaagctt     420
gatatcgaat tcccacgggg ttggggttgc gccttttcca aggcagccct gggtttgcgc     480
```

```
agggacgcgg ctgctctggg cgtggttccg ggaaacgcag cggcgccgac cctgggtctc    540
gcacattctt cacgtccgtt cgcagcgtca cccggatctt cgccgctacc cttgtgggcc    600
ccccggcgac gcttcctgct ccgcccctaa gtcgggaagg ttccttgcgg ttcgcggcgt    660 gccgacgtg  acaaacggaa gccgcacgtc tcactagtac cctcgcagac ggacagcgcc    720
agggagcaat ggcagcgcgc cgaccgcgat gggctgtggc caatagcggc tgctcagcgg    780
ggcgcgccga gagcagcggc cgggaagggg cggtgcggga ggcggggtgt ggggcggtag    840
tgtgggccct gttcctgccc gcgcggtgtt ccgcattctg caagcctccg gagcgcacgt    900
cggcagtcgc ctccctcgtt gaccgaatca ccgacctctc tccccagggg gatccaccgg    960
tcgccaccat ggtgagcaag ggcgaggagc tgttcaccgg ggtggtgccc atcctggtcg   1020
agctggacgg cgacgtaaac ggccacaagt tcagcgtgtc cggcgagggc gagggcgatg   1080
ccacctacgg caagctgacc ctgaagttca tctgcaccac cggcaagctg cccgtgccct   1140
ggcccaccct cgtgaccacc ctgacctacg gcgtgcagtg cttcagccgc taccccgacc   1200
acatgaagca gcacgacttc ttcaagtccg ccatgcccga aggctacgtc caggagcgca   1260
ccatcttctt caaggacgac ggcaactaca agacccgcgc cgaggtgaag ttcgagggcg   1320
acaccctggt gaaccgcatc gagctgaagg gcatcgactt caaggaggac ggcaacatcc   1380
tggggcacaa gctggagtac aactacaaca gccacaacgt ctatatcatg gccgacaagc   1440
agaagaacgg catcaaggtg aacttcaaga tccgccacaa catcgaggac ggcagcgtgc   1500
agctcgccga ccactaccag cagaacaccc ccatcggcga cggccccgtg ctgctgcccg   1560
acaaccacta cctgagcacc cagtccgccc tgagcaaaga ccccaacgag aagcgcgatc   1620
acatggtcct gctggagttc gtgaccgccg ccgggatcac tctcggcatg gacgagctgt   1680
acaagtaaag cggccgcgtc gacaatcaac ctctggatta caaaatttgt gaaagattga   1740
ctggtattct taactatgtt gctcctttta cgctatgtgg atacgctgct ttaatgcctt   1800
tgtatcatgc tattgcttcc cgtatggctt tcattttctc ctccttgtat aaatcctggt   1860
tgctgtctct ttatgaggag ttgtggcccg ttgtcaggca acgtggcgtg gtgtgcactg   1920
tgtttgctga cgcaaccccc actggttggg gcattgccac cacctgtcag ctcctttccg   1980
ggactttcgc tttccccctc cctattgcca cggcggaact catcgccgcc tgccttgccc   2040
gctgctggac aggggctcgg ctgttgggca ctgacaattc cgtggtgttg tcggggaagc   2100
tgacgtcctt tccatggctg ctcgcctgtg ttgccacctg gattctgcgc gggacgtcct   2160
tctgctacgt cccttcggcc ctcaatccag cggaccttcc ttcccgcggc ctgctgccgg   2220
ctctgcggcc tcttccgcgt cttcgccttc gccctcagac gagtcggatc tccctttggg   2280
ccgcctcccc gcctggaatt cgagctcggt acctttaaga ccaatgactt acaaggcagc   2340
tgtagatctt agccactttt taaaagaaaa ggggggactg aagggctaa ttcactccca   2400 acgaagacaa gatctgcttt ttgcttgtac tgggtctctc tggttagacc agatctgagc   2460
ctgggagctc tctggctaac tagggaaccc actgcttaag cctcaataaa gcttgccttg   2520
agtgcttcaa gtagtgtgtg cccgtctgtt gtgtgactct ggtaactaga gatccctcag   2580 accctttttag tcagtgtgga aaatctctag cagtggcgcc cgaacaggga cttgaaagcg   2640
aaagggaaac cagaggagct ctctcgacgc aggactcggc ttgctgaagc gcgcacggca   2700
agaggcgagg ggcggcgact ggtgagtacg ccaaaaattt tgactagcgg aggctagaag   2760
gagagagatg ggtgcgagag cgtcagtatt aagcggggga gaattagatc gcgatgggaa   2820
```

```
aaaattcggt taaggccagg gggaaagaaa aatataaat taaaacatat agtatgggca    2880
agcagggagc tagaacgatt cgcagttaat cctggcctgt tagaaacatc agaaggctgt    2940
agacaaatac tgggacagct acaaccatcc cttcagacag gatcagaaga acttagatca    3000
ttatataata cagtagcaac cctctattgt gtgcatcaaa ggatagagat aaaagacacc    3060
aaggaagctt tagacaagat agaggaagag caaaacaaaa gtaagaccac cgcacagcaa    3120
gcggccgctg atcttcagac ctggaggagg agatatgagg acaattgga gaagtgaatt    3180
atataaatat aaagtagtaa aaattgaacc attaggagta gcacccacca aggcaaagag    3240
aagagtggtg cagagagaaa aaagagcagt gggaatagga gctttgttcc ttgggttctt    3300
gggagcagca ggaagcacta tgggcgcagc gtcaatgacg ctgacggtac aggccagaca    3360
attattgtct ggtatagtgc agcagcagaa caatttgctg agggctattg aggcgcaaca    3420
gcatctgttg caactcacag tctggggcat caagcagctc caggcaagaa tcctggctgt    3480
ggaaagatac ctaaaggatc aacagctcct ggggatttgg ggttgctctg gaaaactcat    3540
ttgcaccact gctgtgcctt ggaatgctag ttggagtaat aaatctctgg aacagatttg    3600
gaatcacacg acctggatgg agtgggacag agaaattaac aattacacaa gcttaataca    3660
ctccttaatt gaagaatcgc aaaaccagca agaaaagaat gaacaagaat tattggaatt    3720
agataaatgg gcaagtttgt ggaattggtt taacataaca aattggctgt ggtatataaa    3780
attattcata atgatagtag gaggcttggt aggtttaaga atagttttg ctgtactttc    3840
tatagtgaat agagttaggc agggatattc accattatcg tttcagaccc acctcccaac    3900
cccgagggga cccgacaggc ccgaaggaat agaagaagaa ggtggagaga gagacagaga    3960
cagatccatt cgattagtga acggatctag tagttcatgt catcttatta ttcagtattt    4020
ataacttgca agaaatgaa tatcagagag tgagaggaac ttgtttattg cagcttataa    4080
tggttacaaa taaagcaata gcatcacaaa tttcacaaat aaagcatttt tttcactgca    4140
ttctagttgt ggtttgtcca aactcatcaa tgtatcttat catgtctggc tctagctatc    4200
ccgcccctaa ctccgcccat cccgccccta actccgccca gttccgccca ttctccgccc    4260
catggctgac taattttttt tatttatgca gaggccgagg ccgcctcggc ctctgagcta    4320
ttccagaagt agtgaggagg cttttttgga ggcctaggct tttgcgtcga cgtaccca    4380
attcgcccta tagtgagtcg tattacgcgc gctcactggc cgtcgtttta caacgtcgtg    4440
actgggaaaa ccctggcgtt acccaactta atcgccttgc agcacatccc cctttcgcca    4500
gctggcgtaa tagcgaagag gcccgcaccg atcgcccttc ccaacagttg cgcagcctga    4560
atggcgaatg gcgcgacgcg ccctgtagcg gcgcattaag cgcggcgggt gtggtggtta    4620
cgcgcagcgt gaccgctaca cttgccagcg ccctagcgcc cgctcctttc gctttcttcc    4680
cttcctttct cgccacgttc gccggctttc cccgtcaagc tctaaatcgg ggctccctt    4740
tagggttccg atttagtgct ttacggcacc tcgaccccaa aaaacttgat tagggtgatg    4800
gttcacgtag tgggccatcg ccctgataga cggtttttcg ccctttgacg ttggagtcca    4860
cgttctttaa tagtggactc ttgttccaaa ctggaacaac actcaaccct atctcggtct    4920
attcttttga tttataaggg attttgccga tttcggccta ttggttaaaa atgagctga    4980
tttaacaaaa atttaacgcg aattttaaca aaatattaac gtttacaatt cccaggtgg    5040
cacttttcgg ggaaatgtgc gcggaacccc tatttgttta tttttctaaa tacattcaaa    5100
tatgtatccc tcatgagac aataaccctg ataaatgctt caataatatt gaaaaggaa    5160
gagtatgagt attcaacatt tccgtgtcgc ccttattccc ttttttgcgg cattttgcct    5220
```

```
tcctgttttt gctcacccag aaacgctggt gaaagtaaaa gatgctgaag atcagttggg    5280
tgcacgagtg ggttacatcg aactggatct caacagcggt aagatccttg agagttttcg    5340
ccccgaagaa cgttttccaa tgatgagcac ttttaaagtt ctgctatgtg gcgcggtatt    5400
atcccgtatt gacgccgggc aagagcaact cggtcgccgc atacactatt ctcagaatga    5460
cttggttgag tactcaccag tcacagaaaa gcatcttacg gatggcatga cagtaagaga    5520
attatgcagt gctgccataa ccatgagtga taacactgcg ccaacttac ttctgacaac    5580 gatcggagga ccgaaggagc taaccgcttt tttgcacaac atgggggatc atgtaactcg    5640
ccttgatcgt tgggaaccgg agctgaatga agccatacca aacgacgagc gtgacaccac    5700
gatgcctgta gcaatggcaa caacgttgcg caaactatta actggcgaac tacttactct    5760
agcttcccgg caacaattaa tagactggat ggaggcggat aaagttgcag gaccacttct    5820
gcgctcggcc cttccggctg gctggtttat tgctgataaa tctggagccg gtgagcgtgg    5880
gtctcgcggt atcattgcag cactggggcc agatggtaag ccctcccgta tcgtagttat    5940
ctacacgacg gggagtcagg caactatgga tgaacgaaat agacagatcg ctgagatagg    6000
tgcctcactg attaagcatt ggtaactgtc agaccaagtt tactcatata ctttagat     6060 tgatttaaaa cttcattttt aatttaaaag gatctaggtg aagatccttt ttgataatct    6120
catgaccaaa atcccttaac gtgagttttc gttccactga gcgtcagacc ccgtagaaaa    6180
gatcaaagga tcttcttgag atcctttttt tctgcgcgta atctgctgct tgcaaacaaa    6240
aaaaccaccg ctaccagcgg tggtttgttt gccggatcaa gagctaccaa ctcttttcc    6300 gaaggtaact ggcttcagca gagcgcagat accaaatact gtccttctag tgtagccgta    6360
gttaggccac cacttcaaga actctgtagc accgcctaca tacctcgctc tgctaatcct    6420
gttaccagtg gctgctgcca gtggcgataa gtcgtgtctt accgggttgg actcaagacg    6480
atagttaccg gataaggcgc agcggtcggg ctgaacgggg ggttcgtgca cacagcccag    6540
cttggagcga acgacctaca ccgaactgag atacctacag cgtgagctat gagaaagcgc    6600
cacgcttccc gaagggagaa aggcggacag gtatccggta agcggcaggg tcggaacagg    6660
agagcgcacg agggagcttc cagggggaaa cgcctggtat ctttatagtc ctgtcgggtt    6720
tcgccacctc tgacttgagc gtcgattttt gtgatgctcg tcaggggggc ggagcctatg    6780
gaaaaacgcc agcaacgcgg cctttttacg gttcctggcc ttttgctggc cttttgctca    6840
catgttcttt cctgcgttat cccctgattc tgtggataac cgtattaccg cctttgagtg    6900
agctgatacc gctcgccgca gccgaacgac cgagcgcagc gagtcagtga gcgaggaagc    6960
ggaagagcgc ccaatacgca aaccgcctct ccccgcgcgt tggccgattc attaatgcag    7020
ctggcacgac aggtttcccg actggaaagc gggcagtgag cgcaacgcaa ttaatgtgag    7080
ttagctcact cattaggcac cccaggcttt acactttatg cttccggctc gtatgttgtg    7140
tggaattgtg agcggataac aatttcacac aggaaacagc tatgaccatg attacgccaa    7200
gcgcgcaatt aaccctcact aaagggaaca aaagctggag ctgca                   7245
```

<210> SEQ ID NO 7
<211> LENGTH: 7257
<212> TYPE: DNA
<213> ORGANISM: Artificial sequence
<220> FEATURE:
<223> OTHER INFORMATION: Construct pLTR1.5/PGK-eGFP-WPRE

<400> SEQUENCE: 7

-continued

| | | | | |
|---|---|---|---|---|
| agcttaatgt | agtcttatgc | aatactcttg | tagtcttgca | acatggtaac gatgagttag | 60 |
| caacatgcct | tacaaggaga | gaaaaagcac | cgtgcatgcc | gattggtgga agtaaggtgg | 120 |
| tacgatcgtg | ccttattagg | aaggcaacag | acgggtctga | catggattgg acgaaccact | 180 |
| gaattgccgc | attgcagaga | tattgtattt | aagtgcctag | ctcgatacaa taaacgtggc | 240 |
| gcccgaacag | ggactcgacg | gtatcggtta | acttttaaaa | gaaaaggggg gattgggggg | 300 |
| tacagtgcag | gggaaagaat | agtagacata | atagcaacag | acatacaaac taaagaatta | 360 |
| caaaaacaaa | ttacaaaaat | tcaaaatttt | atcgatcacg | agactagcct cgagaagctt | 420 |
| gatatcgaat | tcccacgggg | ttggggttgc | gccttttcca | aggcagccct gggtttgcgc | 480 |
| agggacgcgg | ctgctctggg | cgtggttccg | ggaaacgcag | cggcgccgac cctgggtctc | 540 |
| gcacattctt | cacgtccgtt | cgcagcgtca | cccggatctt | cgccgctacc cttgtgggcc | 600 |
| ccccggcgac | gcttcctgct | ccgcccctaa | gtcgggaagg | ttccttgcgg ttcgcggcgt | 660 |
| gccggacgtg | acaaacggaa | gccgcacgtc | tcactagtac | cctcgcagac ggacagcgcc | 720 |
| agggagcaat | ggcagcgcgc | cgaccgcgat | gggctgtggc | caatagcggc tgctcagcgg | 780 |
| ggcgcgccga | gagcagcggc | cgggaagggg | cggtgcggga | ggcggggtgt ggggcggtag | 840 |
| tgtgggccct | gttcctgccc | gcgcggtgtt | ccgcattctg | caagcctccg gagcgcacgt | 900 |
| cggcagtcgg | ctccctcgtt | gaccgaatca | ccgacctctc | tccccagggg gatccaccgg | 960 |
| tcgccaccat | ggtgagcaag | ggcgaggagc | tgttcaccgg | ggtggtgccc atcctggtcg | 1020 |
| agctggacgg | cgacgtaaac | ggccacaagt | tcagcgtgtc | cggcgagggc gagggcgatg | 1080 |
| ccacctacgg | caagctgacc | ctgaagttca | tctgcaccac | cggcaagctg cccgtgccct | 1140 |
| ggcccaccct | cgtgaccacc | ctgacctacg | gcgtgcagtg | cttcagccgc taccccgacc | 1200 |
| acatgaagca | gcacgacttc | ttcaagtccg | ccatgcccga | aggctacgtc caggagcgca | 1260 |
| ccatcttctt | caaggacgac | ggcaactaca | agacccgcgc | cgaggtgaag ttcgagggcg | 1320 |
| acaccctggt | gaaccgcatc | gagctgaagg | gcatcgactt | caaggaggac ggcaacatcc | 1380 |
| tggggcacaa | gctggagtac | aactacaaca | gccacaacgt | ctatatcatg gccgacaagc | 1440 |
| agaagaacgg | catcaaggtg | aacttcaaga | tccgccacaa | catcgaggac ggcagcgtgc | 1500 |
| agctcgccga | ccactaccag | cagaacaccc | ccatcggcga | cggccccgtg ctgctgcccg | 1560 |
| acaaccacta | cctgagcacc | cagtccgccc | tgagcaaaga | ccccaacgag aagcgcgatc | 1620 |
| acatggtcct | gctggagttc | gtgaccgccg | ccgggatcac | tctcggcatg gacgagctgt | 1680 |
| acaagtaaag | cggccgcgtc | gacaatcaac | ctctggatta | caaaatttgt gaaagattga | 1740 |
| ctggtattct | taactatgtt | gctcctttta | cgctatgtgg | atacgctgct ttaatgcctt | 1800 |
| tgtatcatgc | tattgcttcc | cgtatggctt | tcattttctc | ctccttgtat aaatcctggt | 1860 |
| tgctgtctct | ttatgaggag | ttgtggcccg | ttgtcaggca | acgtggcgtg gtgtgcactg | 1920 |
| tgtttgctga | cgcaacccccc | actggttggg | gcattgccac | cacctgtcag ctcctttccg | 1980 |
| ggactttcgc | tttccccctc | cctattgcca | cggcggaact | catcgccgcc tgccttgccc | 2040 |
| gctgctggac | aggggctcgg | ctgttgggca | ctgacaattc | cgtggtgttg tcggggaagc | 2100 |
| tgacgtcctt | tccatggctg | ctcgcctgtg | ttgccacctg | gattctgcgc gggacgtcct | 2160 |
| tctgctacgt | cccttcggcc | ctcaatccag | cggaccttcc | ttcccgcggc ctgctgccgg | 2220 |
| ctctgcggcc | tcttccgcgt | cttcgccttc | gccctcagac | gagtcggatc tccctttggg | 2280 |
| ccgcctcccc | gcctggaatt | cgagctcggt | acctttaaga | ccaatgactt acaaggcagc | 2340 |
| tgtagatctt | agccactttt | taaaagaaaa | gggggggactg | gaagggctaa ttcactccca | 2400 |

```
acgaagacaa gatctgcttt ttgcttgtac tgggtctctc tggttagacc agatctgagc   2460
ctgggagctc tctggctaac tagggaaccc actgcttaag cctcaataaa gcttgccttg   2520
agtgcttcaa gtagtgtgtg cccgtctgtt gtgtgactct ggtaactaga gatccctcag   2580
acccttttag tcagtgtgga aaatctctag cagtggcgcc cgaacaggga cttgaaagcg   2640
aaagggaaac cagaggagct ctctcgacgc aggactcggc ttgctgaagc gcgcacggca   2700
agaggcgagg ggcggcgact ggtgagtacg ccaaaaattt tgactagcgg aggctagaag   2760
gagagagatg ggtgcgagag cgtcagtatt aagcggggga gaattagatc gcgatgggaa   2820
aaaattcggt taaggccagg gggaagaaa aaatataaat taaaacatat agtatgggca    2880
agcagggagc tagaacgatt cgcagttaat cctggcctgt tagaaacatc agaaggctgt   2940
agacaaatac tgggacagct acaaccatcc cttcagacag gatcagaaga acttagatca   3000
ttatataata cagtagcaac cctctattgt gtgcatcaaa ggatagagat aaaagacacc   3060
aaggaagctt tagacaagat agaggaagag caaaacaaaa gtaagaccac cgcacagcaa   3120
gcggccgctg atcttcagac ctggaggagg agatatgagg gacaattgga gaagtgaatt   3180
atataaatat aaagtagtaa aaattgaacc attaggagta gcacccacca aggcaaagag   3240
aagagtggtg cagagagaaa aaagagcagt gggaatagga gctttgttcc ttgggttctt   3300
gggagcagca ggaagcacta tgggcgcagc gtcaatgacg ctgacggtac aggccagaca   3360
attattgtct ggtatagtgc agcagcagaa caatttgctg agggctattg aggcgcaaca   3420
gcatctgttg caactcacag tctggggcat caagcagctc caggcaagaa tcctggctgt   3480
ggaaagatac ctaaaggatc aacagctcct ggggatttgg ggttgctctg gaaaactcat   3540
ttgcaccact gctgtgcctt ggaatgctag ttggagtaat aaatctctgg aacagatttg   3600
gaatcacacg acctggatgg agtgggacag agaaattaac aattacacaa gcttaataca   3660
ctccttaatt gaagaatcgc aaaaccagca agaaaagaat gaacaagaat tattggaatt   3720
agataaatgg gcaagtttgt ggaattggtt taacataaca aattggctgt ggtatataaa   3780
attattcata atgatagtag gaggcttggt aggtttaaga atagttttt ctgtactttc    3840 tatagtgaat agagttaggc agggatattc accattatcg tttcagaccc acctcccaac   3900
cccgagggga cccgacaggc ccgaaggaat agaagaagaa ggtggagaga gagacagaga   3960
cagatccatt cgattagtga acggatccag acatgataag atacattgat gagtttggac   4020
aaaccacaac tagaatgcag tgaaaaaaat gctttatttg tgaaatttgt gatgctattg   4080
ctttatttgt aaccattata agctgcaata acaagttaa caacaacaat tgcattcatt     4140
ttatgtttca ggttcagggg gagatgtggg aggttttta aagcaagtaa aacctctaca    4200
aatgtggtaa tcccgcccct aactccgccc atcccgcccc taactccgcc cagttccgcc   4260
cattctccgc cccatggctg actaattttt tttatttatg cagaggccga ggccgcctcg   4320
gcctctgagc tattccagaa gtagtgagga ggcttttttg gaggcctagg cttttgcgtc   4380
gagacgtacc caattcgccc tatagtgagt cgtattacgc gcgctcactg gccgtcgttt   4440
tacaacgtcg tgactgggaa aaccctggcg ttacccaact taatcgcctt gcagcacatc   4500 ccccttcgc cagctggcgt aatagcgaag aggcccgcac cgatcgccct tcccaacagt    4560
tgcgcagcct gaatggcgaa tggcgcgacg cgcctgtag cggcgcatta agcgcggcgg    4620
gtgtggtggt tacgcgcagc gtgaccgcta cacttgccag cgccctagcg cccgctcctt   4680
tcgctttctt cccttccttt ctcgccacgt tcgccggctt tccccgtcaa gctctaaatc   4740
```

```
                                -continued
gggggctccc tttagggttc cgatttagtg ctttacggca cctcgacccc aaaaaacttg    4800
attagggtga tggttcacgt agtgggccat cgccctgata gacggttttt cgcccttgta    4860
cgttggagtc cacgttcttt aatagtggac tcttgttcca aactggaaca cactcaacc     4920 ctatctcggt ctattctttt gatttataag gattttgcc gatttcggcc tattggttaa     4980
aaaatgagct gatttaacaa aaatttaacg cgaattttaa caaaatatta acgtttacaa    5040
tttcccaggt ggcacttttc ggggaaatgt gcgcggaacc cctatttgtt tattttttcta   5100 aatacattca aatatgtatc cgctcatgag acaataaccc tgataaatgc ttcaataata    5160
ttgaaaaagg aagagtatga gtattcaaca tttccgtgtc gcccttattc ccttttttgc    5220
ggcattttgc cttcctgttt ttgctcaccc agaaacgctg gtgaaagtaa agatgctga    5280 agatcagttg ggtgcacgag tgggttacat cgaactggat ctcaacagcg gtaagatcct    5340
tgagagtttt cgccccgaag aacgttttcc aatgatgagc acttttaaag ttctgctatg    5400
tggcgcggta ttatcccgta ttgacgccgg gcaagagcaa ctcggtcgcc gcatacacta    5460
ttctcagaat gacttggttg agtactcacc agtcacagaa aagcatctta cggatggcat    5520
gacagtaaga gaattatgca gtgctgccat aaccatgagt gataacactg cggccaactt    5580
acttctgaca acgatcggag gaccgaagga gctaaccgct tttttgcaca acatggggga    5640
tcatgtaact cgccttgatc gttgggaacc ggagctgaat gaagccatac caaacgacga    5700
gcgtgacacc acgatgcctg tagcaatggc aacaacgttg cgcaaactat taactggcga    5760
actacttact ctagcttccc ggcaacaatt aatagactgg atggaggcgg ataaagttgc    5820
aggaccactt ctgcgctcgg cccttccggc tggctggttt attgctgata atctggagc     5880 cggtgagcgt gggtctcgcg gtatcattgc agcactgggg ccagatggta agccctcccg    5940
tatcgtagtt atctacacga cggggagtca ggcaactatg gatgaacgaa atagacagat    6000
cgctgagata ggtgcctcac tgattaagca ttggtaactg tcagaccaag tttactcata    6060
tatactttag attgatttaa aacttcattt ttaatttaaa aggatctagg tgaagatcct    6120
ttttgataat ctcatgacca aaatccctta acgtgagttt tcgttccact gagcgtcaga    6180
ccccgtagaa aagatcaaag gatcttcttg agatcctttt tttctgcgcg taatctgctg    6240
cttgcaaaca aaaaaaccac cgctaccagc ggtggtttgt ttgccggatc aagagctacc    6300
aactcttttt ccgaaggtaa ctggcttcag cagagcgcag ataccaaata ctgtccttct    6360
agtgtagccg tagttaggcc accacttcaa gaactctgta gcaccgccta catacctcgc    6420
tctgctaatc ctgttaccag tggctgctgc cagtggcgat aagtcgtgtc ttaccgggtt    6480
ggactcaaga cgatagttac cggataaggc gcagcggtcg ggctgaacgg ggggttcgtg    6540
cacacagccc agcttggagc gaacgaccta caccgaactg agatacctac agcgtgagct    6600
atgagaaagc gccacgcttc ccgaagggag aaaggcggac aggtatccgg taagcggcag    6660
ggtcggaaca ggagagcgca cgagggagct tccaggggga aacgcctggt atctttatag    6720
tcctgtcggg tttcgccacc tctgacttga gcgtcgattt ttgtgatgct cgtcaggggg    6780
gcggagccta tggaaaaacg ccagcaacgc ggcctttta cggttcctgg ccttttgctg     6840
gccttttgct cacatgttct ttcctgcgtt atcccctgat tctgtggata accgtattac    6900
cgcctttgag tgagctgata ccgctcgccg cagccgaacg accgagcgca gcgagtcagt    6960
gagcgaggaa gcggaagagc gcccaatacg caaaccgcct ctccccgcgc gttggccgat    7020
tcattaatgc agctggcacg acaggtttcc cgactggaaa gcgggcagtg agcgcaacgc    7080
aattaatgtg agttagctca ctcattaggc accccaggct ttacacttta tgcttccggc    7140
```

-continued tcgtatgttg tgtggaattg tgagcggata acaatttcac acaggaaaca gctatgacca    7200
tgattacgcc aagcgcgcaa ttaaccctca ctaaagggaa caaaagctgg agctgca       7257

<210> SEQ ID NO 8
<211> LENGTH: 7688
<212> TYPE: DNA
<213> ORGANISM: Artificial sequence
<220> FEATURE:
<223> OTHER INFORMATION: Construct pLTR1.7.671/PGK-eGFP-WPRE

<400> SEQUENCE: 8
ccattgcata cgttgtatcc atatcataat atgtacattt atattggctc atgtccaaca      60
ttaccgccat gttgacattg attattgact agttattaat agtaatcaat tacgggtca     120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccacccat tgacgtcaat    540 gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc tggcgcccga acagggactg ctagcgttaa cttttaaaag aaaaggggg     720 attgggggt acagtgcagg ggaaagaata gtagacataa tagcaacaga catacaaact     780
aaagaattac aaaaacaaat tacaaaaatt caaaatttta tcgatcacga gactagcctc     840
gagaagcttg atatcgaatt cccacggggt tggggttgcg cctttccaa ggcagccctg     900 ggtttgcgca gggacgcggc tgctctgggc gtggttccgg gaaacgcagc ggcgccgacc    960
ctgggtctcg cacattcttc acgtccgttc gcagcgtcac ccggatcttc gccgctaccc   1020
ttgtgggccc ccggcgacg cttcctgctc cgccctaag tcgggaaggt tccttgcggt   1080
tcgcggcgtg ccggacgtga caaacggaag ccgcacgtct cactagtacc ctcgcagacg   1140
gacagcgcca gggagcaatg gcagcgcgcc gaccgcgatg ggctgtggcc aatagcggct   1200
gctcagcggg gcgcgccgag agcagcggcc gggaaggggc ggtgcgggag gcggggtgtg   1260
gggcggtagt gtgggccctg ttcctgcccg cgcggtgttc cgcattctgc aagcctccgg   1320
agcgcacgtc ggcagtcggc tccctcgttg accgaatcac cgacctctct ccccaggggg   1380
atccaccggt cgccaccatg gtgagcaagg gcgaggagct gttcaccggg gtggtgccca   1440
tcctggtcga gctggacggc gacgtaaacg gccacaagtt cagcgtgtcc ggcgagggcg   1500
agggcgatgc cacctacggc aagctgaccc tgaagttcat ctgcaccacc ggcaagctgc   1560
ccgtgccctg gcccaccctc gtgaccaccc tgacctacgg cgtgcagtgc ttcagccgct   1620
accccgacca catgaagcag cacgacttct tcaagtccgc catgcccgaa ggctacgtcc   1680
aggagcgcac catcttcttc aaggacgacg gcaactacaa gacccgcgcc gaggtgaagt   1740
tcgagggcga caccctggtg aaccgcatcg agctgaaggg catcgacttc aaggaggacg   1800
gcaacatcct ggggcacaag ctggagtaca actacaacag ccacaacgtc tatatcatgg   1860
ccgacaagca gaagaacggc atcaaggtga acttcaagat ccgccacaac atcgaggacg   1920

```
gcagcgtgca gctcgccgac cactaccagc agaacacccc catcggcgac ggccccgtgc    1980
tgctgcccga caaccactac ctgagcaccc agtccgccct gagcaaagac cccaacgaga    2040
agcgcgatca catggtcctg ctggagttcg tgaccgccgc cgggatcact ctcggcatgg    2100
acgagctgta caagtaaagc ggccgcgtcg acaatcaacc tctggattac aaaatttgtg    2160
aaagattgac tggtattctt aactatgttg ctccttttac gctatgtgga tacgctgctt    2220
taatgccttt gtatcatgct attgcttccc gtatggcttt cattttctcc tccttgtata    2280
aatcctggtt gctgtctctt tatgaggagt tgtggcccgt tgtcaggcaa cgtggcgtgg    2340
tgtgcactgt gtttgctgac gcaaccccca ctggttgggg cattgccacc acctgtcagc    2400
tcctttccgg gactttcgct ttccccctcc ctattgccac ggcggaactc atcgccgcct    2460
gccttgcccg ctgctggaca ggggctcggc tgttgggcac tgacaattcc gtggtgttgt    2520
cggggaagct gacgtccttt ccatggctgc tcgcctgtgt tgccacctgg attctgcgcg    2580
ggacgtcctt ctgctacgtc ccttcggccc tcaatccagc ggaccttcct tcccgcggcc    2640
tgctgccggc tctgcggcct cttccgcgtc ttcgccttcg ccctcagacg agtcggatct    2700
ccctttgggc cgcctccccg cctggaattc gagctcggta cctttaagac caatgactta    2760
caaggcagct gtagatctta gccactttt aaaagaaaag gggggactgg aagggctaat    2820
tcactcccaa cgaagacaag atctgctttt tgcttgtact gggtctctct ggttagacca    2880
gatctgagcc tgggagctct ctggctaact agggaaccca ctgcttaagc ctcaataaag    2940
cttgccttga gtgcttcaag tagtgtgtgc ccgtctgttg tgtgactctg gtaactagag    3000
atccctcaga ccctttttagt cagtgtggaa aatctctagc agtggcgccc gaacagggac    3060
ttgaaagcga agggaaacc agaggagctc tctcgacgca ggactcggct tgctgaagcg    3120
cgcacggcaa gaggcgaggg gcggcgactg gtgagtacgc caaaaatttt gactagcgga    3180
ggctagaagg agagagatgg gtgcgagagc gtcagtatta gcggggggag aattagatcg    3240
cgatgggaaa aaattcggtt aaggccaggg ggaaagaaaa aatataaatt aaaacatata    3300
gtatgggcaa gcagggagct agaacgattc gcagttaatc ctggcctgtt agaaacatca    3360
gaaggctgta gacaaatact gggacagcta caaccatccc ttcagacagg atcagaagaa    3420
cttagatcat tatataatac agtagcaacc ctctattgtg tgcatcaaag gatagagata    3480
aaagacacca aggaagcttt agacaagata gaggaagagc aaaacaaaag taagaccacc    3540
gcacagcaag cggccgctga tcttcagacc tggaggagga gatatgaggg acaattggag    3600
aagtgaatta tataaatata agtagtaaa aattgaacca ttaggagtag cacccaccaa    3660
ggcaaagaga agagtggtgc agagagaaaa aagagcagtg ggaataggag ctttgttcct    3720
tgggttcttg ggagcagcag gaagcactat gggcgcagcg tcaatgacgc tgacggtaca    3780
ggccagacaa ttattgtctg gtatagtgca gcagcagaac aatttgctga gggctattga    3840
ggcgcaacag catctgttgc aactcacagt ctggggcatc aagcagctcc aggcaagaat    3900
cctggctgtg gaaagatacc taaaggatca acagctcctg ggatttggg gttgctctgg    3960 aaaactcatt tgcaccactg ctgtgccttg aatgctagt tggagtaata atctctggaa    4020
acagatttgg aatcacacga cctggatgga gtgggacaga gaaattaaca attacacaag    4080
cttaatacac tccttaattg aagaatcgca aaaccagcaa gaaaagaatg aacaagaatt    4140
attggaatta gataaatggg caagtttgtg gaattggttt aacataacaa attggctgtg    4200
gtatataaaa ttattcataa tgatagtagg aggcttggta ggtttaagaa tagttttttgc    4260 tgtactttct atagtgaata gagttaggca gggatattca ccattatcgt ttcagaccca    4320
```

```
cctcccaacc ccgagggac ccgacaggcc cgaaggaata gaagaagaag gtggagagag    4380
agacagagac agatccattc gattagtgaa cggatccaga catgataaga tacattgatg    4440
agtttggaca aaccacaact agaatgcagt gaaaaaaatg ctttatttgt gaaatttgtg    4500
atgctattgc tttatttgta accattataa gctgcaataa acaagttaac aacaacaatt    4560
gcattcattt tatgtttcag gttcaggggg agatgtggga ggttttttaa agcaagtaaa    4620
acctctacaa atgtggtaat cccgccccta actccgccca tcccgcccct aactccgccc    4680
agttccgccc attctccgcc ccatggctga ctaattttt ttatttatgc agaggccgag    4740
gccgcctcgg cctctgagct attccagaag tagtgaggag gctttttgg aggcctaggg    4800 acgtacccaa ttcgccctat agtgagtcgt attacgcgcg ctcactggcc gtcgttttac    4860
aacgtcgtga ctgggaaaac cctggcgtta cccaacttaa tcgccttgca gcacatcccc    4920
ctttcgccag ctggcgtaat agcgaagagg cccgcaccga tcgcccttcc caacagttgc    4980
gcagcctgaa tggcgaatgg cgcgacgcgc cctgtagcgg cgcattaagc gcggcgggtg    5040
tggtggttac gcgcagcgtg accgctacac ttgccagcgc cctagcgccc gctcctttcg    5100
ctttcttccc ttcctttctc gccacgttcg ccggctttcc ccgtcaagct ctaaatcggg    5160
ggctcccttt agggttccga tttagtgctt tacggcacct cgaccccaaa aaacttgatt    5220
agggtgatgg ttcacgtagt gggccatcgc cctgatagac ggttttttcgc cctttgacgt    5280 tggagtccac gttctttaat agtggactct tgttccaaac tggaacaaca ctcaaccta    5340 tctcggtcta ttcttttgat ttataaggga ttttgccgat ttcggcctat tggttaaaaa    5400
atgagctgat ttaacaaaaa tttaacgcga attttaacaa aatattaacg tttacaattt    5460
cccaggtggc acttttcggg gaaatgtgcg cggaacccct atttgtttat ttttctaaat    5520
acattcaaat atgtatccgc tcatgagaca ataaccctga taaatgcttc aataatattg    5580
aaaaaggaag agtatgagta ttcaacattt ccgtgtcgcc cttattccct tttttgcggc    5640
attttgcctt cctgtttttg ctcacccaga aacgctggtg aaagtaaaag atgctgaaga    5700
tcagttgggt gcacgagtgg gttacatcga actggatctc aacagcggta agatccttga    5760
gagttttcgc cccgaagaac gttttccaat gatgagcact tttaaagttc tgctatgtgg    5820
cgcggtatta tcccgtattg acgccgggca agagcaactc ggtcgccgca tacactattc    5880
tcagaatgac ttggttgagt actcaccagt cacagaaaag catcttacgg atggcatgac    5940
agtaagagaa ttatgcagtg ctgccataac catgagtgat aacactgcgg ccaacttact    6000
tctgacaacg atcggaggac cgaaggagct aaccgctttt ttgcacaaca tgggggatca    6060
tgtaactcgc cttgatcgtt gggaaccgga gctgaatgaa gccataccaa acgacgagcg    6120
tgacaccacg atgcctgtag caatggcaac aacgttgcgc aaactattaa ctggcgaact    6180
acttactcta gcttcccggc aacaattaat agactggatg gaggcggata agttgcagg    6240 accacttctg cgctcggccc ttccggctgg ctggtttatt gctgataaat ctggagccgg    6300
tgagcgtggg tctcgcggta tcattgcagc actggggcca gatggtaagc cctcccgtat    6360
cgtagttatc tacacgacgg ggagtcaggc aactatggat gaacgaaata gacagatcgc    6420
tgagataggt gcctcactga ttaagcattg gtaactgtca gaccaagttt actcatatat    6480
actttagatt gatttaaaac ttcattttta atttaaaagg atctaggtga agatcctttt    6540
tgataatctc atgaccaaaa tcccttaacg tgagttttcg ttccactgag cgtcagaccc    6600
cgtagaaaag atcaaaggat cttcttgaga tccttttttt ctgcgcgtaa tctgctgctt    6660
```

```
gcaaacaaaa aaaccaccgc taccagcggt ggtttgtttg ccggatcaag agctaccaac    6720 tcttttttccg aaggtaactg gcttcagcag agcgcagata ccaaatactg tccttctagt    6780
gtagccgtag ttaggccacc acttcaagaa ctctgtagca ccgcctacat acctcgctct    6840
gctaatcctg ttaccagtgg ctgctgccag tggcgataag tcgtgtctta ccgggttgga    6900
ctcaagacga tagttaccgg ataaggcgca gcggtcgggc tgaacggggg gttcgtgcac    6960
acagcccagc ttggagcgaa cgacctacac cgaactgaga tacctacagc gtgagctatg    7020
agaaagcgcc acgcttcccg aagggagaaa ggcggacagg tatccggtaa gcggcagggt    7080
cggaacagga gagcgcacga gggagcttcc agggggaaac gcctggtatc tttatagtcc    7140
tgtcgggttt cgccacctct gacttgagcg tcgatttttg tgatgctcgt caggggggcg    7200
gagcctatgg aaaaacgcca gcaacgcggc cttttacgg ttcctggcct tttgctggcc    7260
ttttgctcac atgttctttc ctgcgttatc ccctgattct gtggataacc gtattaccgc    7320
ctttgagtga gctgataccg ctcgccgcag ccgaacgacc gagcgcagcg agtcagtgag    7380
cgaggaagcg gaagagcgcc caatacgcaa accgcctctc cccgcgcgtt ggccgattca    7440
ttaatgcagc tggcacgaca ggtttcccga ctggaaagcg ggcagtgagc gcaacgcaat    7500
taatgtgagt tagctcactc attaggcacc ccaggcttta cactttatgc ttccggctcg    7560
tatgttgtgt ggaattgtga gcggataaca atttcacaca ggaaacagct atgaccatga    7620
ttacgccaag cgcgcaatta accctcacta aagggaacaa aagctggagc tgcaagcttg    7680
catgctgg                                                              7688

<210> SEQ ID NO 9
<211> LENGTH: 7689
<212> TYPE: DNA
<213> ORGANISM: Artificial sequence
<220> FEATURE:
<223> OTHER INFORMATION: Construct pLTR1.7.672/PGK-eGFP-WPRE

<400> SEQUENCE: 9
ccattgcata cgttgtatcc atatcataat atgtacattt atattggctc atgtccaaca      60
ttaccgccat gttgacattg attattgact agttattaat agtaatcaat tacgggtca     120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc gtggcgcccg aacagggact gctagcgtta acttttaaaa gaaaaggggg    720
gattgggggg tacagtgcag gggaaagaat agtagacata atagcaacag acatacaaac    780
taaagaatta caaaaacaaa ttacaaaaat tcaaaatttt atcgatcacg agactagcct    840
cgagaagctt gatatcgaat tcccacgggg ttggggttgc gccttttcca aggcagccct    900
gggtttgcgc agggacgcgg ctgctctggg cgtggttccg ggaaacgcag cggcgccgac    960
cctgggtctc gcacattctt cacgtccgtt cgcagcgtca cccggatctt cgccgctacc   1020
```

```
cttgtgggcc ccccggcgac gcttcctgct ccgcccctaa gtcgggaagg ttccttgcgg    1080
ttcgcggcgt gccggacgtg acaaacggaa gccgcacgtc tcactagtac cctcgcagac    1140
ggacagcgcc agggagcaat ggcagcgcgc cgaccgcgat gggctgtggc aatagcggc     1200 tgctcagcgg ggcgcgccga gagcagcggc cgggaagggg cggtgcggga ggcggggtgt    1260
ggggcggtag tgtgggccct gttcctgccc gcgcggtgtt ccgcattctg caagcctccg    1320
gagcgcacgt cggcagtcgg ctccctcgtt gaccgaatca ccgacctctc tccccagggg    1380
gatccaccgg tcgccaccat ggtgagcaag ggcgaggagc tgttcaccgg ggtggtgccc    1440
atcctggtcg agctggacgg cgacgtaaac ggccacaagt tcagcgtgtc cggcgagggc    1500
gagggcgatg ccacctacgg caagctgacc ctgaagttca tctgcaccac cggcaagctg    1560
cccgtgccct ggcccaccct cgtgaccacc ctgacctacg gcgtgcagtg cttcagccgc    1620
taccccgacc acatgaagca gcacgacttc ttcaagtccg ccatgcccga aggctacgtc    1680
caggagcgca ccatcttctt caaggacgac ggcaactaca agacccgcgc cgaggtgaag    1740
ttcgagggcg acaccctggt gaaccgcatc gagctgaagg gcatcgactt caaggaggac    1800
ggcaacatcc tggggcacaa gctggagtac aactacaaca gccacaacgt ctatatcatg    1860
gccgacaagc agaagaacgg catcaaggtg aacttcaaga tccgccacaa catcgaggac    1920
ggcagcgtgc agctcgccga ccactaccag cagaacaccc ccatcggcga cggccccgtg    1980
ctgctgcccg acaaccacta cctgagcacc cagtccgccc tgagcaaaga ccccaacgag    2040
aagcgcgatc acatggtcct gctggagttc gtgaccgccg ccgggatcac tctcggcatg    2100
gacgagctgt acaagtaaag cggccgcgtc gacaatcaac ctctggatta caaaatttgt    2160
gaaagattga ctggtattct taactatgtt gctccttta cgctatgtgg atacgctgct    2220
ttaatgcctt tgtatcatgc tattgcttcc cgtatggctt tcattttctc ctccttgtat    2280
aaatcctggt tgctgtctct ttatgaggag ttgtggcccg ttgtcaggca acgtggcgtg    2340
gtgtgcactg tgtttgctga cgcaaccccc actggttggg gcattgccac cacctgtcag    2400
ctcctttccg ggactttcgc tttccccctc cctattgcca cggcggaact catcgccgcc    2460
tgccttgccc gctgctggac aggggctcgg ctgttgggca ctgacaattc cgtggtgttg    2520
tcggggaagc tgacgtcctt tccatggctg ctcgcctgtg ttgccacctg gattctgcgc    2580
gggacgtcct tctgctacgt cccttcggcc ctcaatccag cggaccttcc ttcccgcggc    2640
ctgctgccgg ctctgcggcc tcttccgcgt cttcgccttc gccctcagac gagtcggatc    2700
tccctttggg ccgcctcccc gcctggaatt cgagctcggt acctttaaga ccaatgactt    2760
acaaggcagc tgtagatctt agccactttt taaaagaaaa ggggggactg aagggctaa     2820 ttcactccca acgaagacaa gatctgcttt ttgcttgtac tgggtctctc tggttagacc    2880
agatctgagc ctgggagctc tctggctaac tagggaaccc actgcttaag cctcaataaa    2940
gcttgccttg agtgcttcaa gtagtgtgtg cccgtctgtt gtgtgactct ggtaactaga    3000
gatccctcag acccttttag tcagtgtgga aaatctctag cagtggcgcc cgaacaggga    3060
cttgaaagcg aaagggaaac cagaggagct ctctcgacgc aggactcggc ttgctgaagc    3120
gcgcacggca agaggcgagg ggcggcgact ggtgagtacg ccaaaaattt tgactagcgg    3180
aggctagaag gagagagatg ggtgcgagag cgtcagtatt aagcggggga gaattagatc    3240
gcgatgggaa aaaattcggt taaggccagg gggaaagaaa aaatataaat taaaacatat    3300
agtatgggca agcaggagc tagaacgatt cgcagttaat cctggcctgt tagaaacatc    3360
```

```
agaaggctgt agacaaatac tgggacagct acaaccatcc cttcagacag gatcagaaga    3420
acttagatca ttatataata cagtagcaac cctctattgt gtgcatcaaa ggatagagat    3480
aaaagacacc aaggaagctt tagacaagat agaggaagag caaaacaaaa gtaagaccac    3540
cgcacagcaa gcggccgctg atcttcagac ctggaggagg agatatgagg gacaattgga    3600
gaagtgaatt atataaatat aaagtagtaa aaattgaacc attaggagta gcacccacca    3660
aggcaaagag aagagtggtg cagagagaaa aaagagcagt gggaatagga gctttgttcc    3720
ttgggttctt gggagcagca ggaagcacta tgggcgcagc gtcaatgacg ctgacggtac    3780
aggccagaca attattgtct ggtatagtgc agcagcagaa caatttgctg agggctattg    3840
aggcgcaaca gcatctgttg caactcacag tctggggcat caagcagctc caggcaagaa    3900
tcctggctgt ggaaagatac ctaaaggatc aacagctcct ggggatttgg ggttgctctg    3960
gaaaactcat ttgcaccact gctgtgcctt ggaatgctag ttggagtaat aaatctctgg    4020
aacagatttg gaatcacacg acctggatgg agtgggacag agaaattaac aattacacaa    4080
gcttaataca ctccttaatt gaagaatcgc aaaaccagca agaaaagaat gaacaagaat    4140
tattggaatt agataaatgg gcaagtttgt ggaattggtt taacataaca aattggctgt    4200
ggtatataaa attattcata atgatagtag gaggcttggt aggtttaaga atagtttttg    4260
ctgtactttc tatagtgaat agagttaggc agggatattc accattatcg tttcagaccc    4320
acctcccaac cccgagggga cccgacaggc ccgaaggaat agaagaagaa ggtggagaga    4380
gagacagaga cagatccatt cgattagtga acggatccag acatgataag atacattgat    4440
gagtttggac aaaccacaac tagaatgcag tgaaaaaaat gctttatttg tgaaatttgt    4500
gatgctattg ctttatttgt aaccattata agctgcaata acaagttaa caacaacaat    4560 tgcattcatt ttatgtttca ggttcagggg gagatgtggg aggttttta aagcaagtaa    4620 aacctctaca aatgtggtaa tcccgcccct aactccgccc atcccgcccc taactccgcc    4680
cagttccgcc cattctccgc cccatggctg actaattttt tttatttatg cagaggccga    4740
ggccgcctcg gcctctgagc tattccagaa gtagtgagga ggcttttttg gaggcctagg    4800
gacgtaccca attcgcccta tagtgagtcg tattacgcgc gctcactggc cgtcgtttta    4860
caacgtcgtg actgggaaaa ccctggcgtt acccaactta atcgccttgc agcacatccc    4920
cctttcgcca gctggcgtaa tagcgaagag gcccgcaccg atcgcccttc ccaacagttg    4980
cgcagcctga atggcgaatg gcgcgacgcg ccctgtagcg gcgcattaag cgcggcgggt    5040
gtggtggtta cgcgcagcgt gaccgctaca cttgccagcg ccctagcgcc cgctcctttc    5100
gctttcttcc cttcctttct cgccacgttc gccggctttc cccgtcaagc tctaaatcgg    5160
gggctccctt tagggttccg atttagtgct ttacggcacc tcgaccccaa aaaacttgat    5220
tagggtgatg gttcacgtag tgggccatcg ccctgataga cggtttttcg ccctttgacg    5280
ttggagtcca cgttctttaa tagtggactc ttgttccaaa ctggaacaac actcaaccct    5340
atctcggtct attcttttga tttataaggg attttgccga tttcggccta ttggttaaaa    5400
aatgagctga tttaacaaaa atttaacgcg aattttaaca aaatattaac gtttacaatt    5460
tcccaggtgg cacttttcgg ggaaatgtgc gcggaacccc tatttgttta ttttctaaa    5520 tacattcaaa tatgtatccg ctcatgagac aataaccctg ataaatgctt caataatatt    5580
gaaaaaggaa gagtatgagt attcaacatt tccgtgtcgc ccttattccc ttttttgcgg    5640
cattttgcct tcctgttttt gctcacccag aaacgctggt gaaagtaaaa gatgctgaag    5700
atcagttggg tgcacgagtg ggttacatcg aactggatct caacagcggt aagatccttg    5760
```

-continued

```
agagttttcg ccccgaagaa cgttttccaa tgatgagcac ttttaaagtt ctgctatgtg    5820
gcgcggtatt atcccgtatt gacgccgggc aagagcaact cggtcgccgc atacactatt    5880
ctcagaatga cttggttgag tactcaccag tcacagaaaa gcatcttacg gatggcatga    5940
cagtaagaga attatgcagt gctgccataa ccatgagtga taacactgcg gccaacttac    6000
ttctgacaac gatcggagga ccgaaggagc taaccgcttt tttgcacaac atggggatc     6060 atgtaactcg ccttgatcgt tgggaaccgg agctgaatga agccatacca acgacgagc     6120 gtgacaccac gatgcctgta gcaatggcaa caacgttgcg caaactatta actggcgaac    6180
tacttactct agcttcccgg caacaattaa tagactggat ggaggcggat aaagttgcag    6240
gaccacttct gcgctcggcc cttccggctg gctggtttat tgctgataaa tctggagccg    6300
gtgagcgtgg gtctcgcggt atcattgcag cactggggcc agatggtaag ccctcccgta    6360
tcgtagttat ctacacgacg gggagtcagg caactatgga tgaacgaaat agacagatcg    6420
ctgagatagg tgcctcactg attaagcatt ggtaactgtc agaccaagtt tactcatata    6480
tactttagat tgatttaaaa cttcattttt aatttaaaag gatctaggtg aagatccttt    6540
ttgataatct catgaccaaa atcccttaac gtgagttttc gttccactga gcgtcagacc    6600
ccgtagaaaa gatcaaagga tcttcttgag atcctttttt tctgcgcgta atctgctgct    6660
tgcaaacaaa aaaaccaccg ctaccagcgg tggtttgttt gccggatcaa gagctaccaa    6720 ctcttttttcc gaaggtaact ggcttcagca gagcgcagat accaaatact gtccttctag    6780
tgtagccgta gttaggccac cacttcaaga actctgtagc accgcctaca tacctcgctc    6840
tgctaatcct gttaccagtg gctgctgcca gtggcgataa gtcgtgtctt accgggttgg    6900
actcaagacg atagttaccg gataaggcgc agcggtcggg ctgaacgggg gttcgtgca     6960 cacagcccag cttggagcga acgacctaca ccgaactgag atacctacag cgtgagctat    7020
gagaaagcgc cacgcttccc gaagggagaa aggcggacag gtatccggta agcggcaggg    7080
tcggaacagg agagcgcacg agggagcttc caggggaaa cgcctggtat ctttatagtc     7140
ctgtcgggtt tcgccacctc tgacttgagc gtcgattttt gtgatgctcg tcagggggc     7200 ggagcctatg gaaaaacgcc agcaacgcgg cctttttacg gttcctggcc ttttgctggc    7260
cttttgctca catgttcttt cctgcgttat cccctgattc tgtggataac cgtattaccg    7320
cctttgagtg agctgatacc gctcgccgca gccgaacgac cgagcgcagc gagtcagtga    7380
gcgaggaagc ggaagagcgc ccaatacgca aaccgcctct ccccgcgcgt tggccgattc    7440
attaatgcag ctggcacgac aggtttcccg actggaaagc gggcagtgag cgcaacgcaa    7500
ttaatgtgag ttagctcact cattaggcac cccaggcttt acactttatg cttccggctc    7560
gtatgttgtg tggaattgtg agcggataac aatttcacac aggaaacagc tatgaccatg    7620
attacgccaa gcgcgcaatt aaccctcact aaagggaaca aaagctggag ctgcaagctt    7680
gcatgctgg                                                           7689
```

<210> SEQ ID NO 10
<211> LENGTH: 7690
<212> TYPE: DNA
<213> ORGANISM: Artificial sequence
<220> FEATURE:
<223> OTHER INFORMATION: Construct pLTR1.7.673/PGK-eGFP-WPRE

<400> SEQUENCE: 10

```
ccattgcata cgttgtatcc atatcataat atgtacattt atattggctc atgtccaaca      60
```

```
ttaccgccat gttgacattg attattgact agtattaat agtaatcaat tacgggtca    120
ttagttcata gcccatatat ggagttccgc gttacataac ttacggtaaa tggcccgcct   180
ggctgaccgc ccaacgaccc ccgcccattg acgtcaataa tgacgtatgt tcccatagta   240
acgccaatag ggactttcca ttgacgtcaa tgggtggagt atttacggta aactgcccac   300
ttggcagtac atcaagtgta tcatatgcca agtacgcccc ctattgacgt caatgacggt   360
aaatggcccg cctggcatta tgcccagtac atgaccttat gggactttcc tacttggcag   420
tacatctacg tattagtcat cgctattacc atggtgatgc ggttttggca gtacatcaat   480
gggcgtggat agcggtttga ctcacgggga tttccaagtc tccacccat tgacgtcaat    540
gggagtttgt tttggcacca aaatcaacgg gactttccaa aatgtcgtaa caactccgcc   600
ccattgacgc aaatgggcgg taggcgtgta cggtgggagg tctatataag cagagctcgt   660
ttagtgaacc ggtggcgccc gaacagggac tgctagcgtt aacttttaaa agaaaagggg   720
ggattggggg gtacagtgca ggggaaagaa tagtagacat aatagcaaca gacatacaaa   780
ctaaagaatt acaaaaacaa attacaaaaa ttcaaaattt tatcgatcac gagactagcc   840
tcgagaagct tgatatcgaa ttcccacggg gttggggttg cgccttttcc aaggcagccc   900
tgggtttgcg cagggacgcg gctgctctgg gcgtggttcc gggaaacgca gcggcgccga   960
ccctgggtct cgcacattct tcacgtccgt tcgcagcgtc acccggatct tcgccgctac  1020
ccttgtgggc cccccggcga cgcttcctgc tccgcccta agtcgggaag ttccttgcg    1080
gttcgcggcg tgccggacgt gacaaacgga agccgcacgt ctcactagta ccctcgcaga  1140
cggacagcgc cagggagcaa tggcagcgcg ccgaccgcga tggctgtgg ccaatagcgg   1200
ctgctcagcg gggcgcgccg agagcagcgg ccgggaaggg gcggtgcggg aggcggggtg  1260
tggggcggta gtgtgggccc tgttcctgcc gcgcgcgtgt tccgcattct gcaagcctcc  1320
ggagcgcacg tcggcagtcg gctccctcgt tgaccgaatc accgacctct ctccccaggg  1380
ggatccaccg gtcgccacca tggtgagcaa gggcgaggag ctgttcaccg ggtggtgcc   1440
catcctggtc gagctggacg gcgacgtaaa cggccacaag ttcagcgtgt ccggcgaggg  1500
cgagggcgat gccacctacg gcaagctgac cctgaagttc atctgcacca ccggcaagct  1560
gcccgtgccc tggcccaccc tcgtgaccac cctgacctac ggcgtgcagt gcttcagccg  1620
ctaccccgac cacatgaagc agcacgactt cttcaagtcc gccatgcccg aaggctacgt  1680
ccaggagcgc accatcttct tcaaggacga cggcaactac aagacccgcg ccgaggtgaa  1740
gttcgagggc gacaccctgg tgaaccgcat cgagctgaag ggcatcgact tcaaggagga  1800
cggcaacatc ctggggcaca agctggagta caactacaac agccacaacg tctatatcat  1860
ggccgacaag cagaagaacg gcatcaaggt gaacttcaag atccgccaca acatcgagga  1920
cggcagcgtg cagctcgccg accactacca gcagaacacc cccatcggcg acggccccgt  1980
gctgctgccc gacaaccact acctgagcac ccagtccgcc ctgagcaaag accccaacga  2040
gaagcgcgat cacatggtcc tgctggagtt cgtgaccgcc gccgggatca ctctcggcat  2100
ggacgagctg tacaagtaaa gcggccgcgt cgacaatcaa cctctggatt acaaaatttg  2160
tgaaagattg actggtattc ttaactatgt tgctcctttt acgctatgtg gatacgctgc  2220
tttaatgcct ttgtatcatg ctattgcttc ccgtatggct ttcattttct cctccttgta  2280
taaatcctgg ttgctgtctc tttatgagga gttgtggccc gttgtcaggc aacgtggcgt  2340
ggtgtgcact gtgtttgctg acgcaacccc cactggttgg ggcattgcca ccacctgtca  2400
gctcctttcc gggactttcg ctttccccct ccctattgcc acggcggaac tcatcgccgc  2460
```

```
ctgccttgcc cgctgctgga caggggctcg gctgttgggc actgacaatt ccgtggtgtt    2520
gtcggggaag ctgacgtcct ttccatggct gctcgcctgt gttgccacct ggattctgcg    2580
cgggacgtcc ttctgctacg tcccttcggc cctcaatcca gcggaccttc ctteccgcgg    2640 cctgctgccg gctctgcggc ctcttccgcg tcttcgcctt cgccctcaga cgagtcggat    2700 ctcccttttgg gccgcctccc cgcctggaat tcgagctcgg tacctttaag accaatgact    2760
tacaaggcag ctgtagatct tagccacttt ttaaaagaaa aggggggact ggaagggcta    2820
attcactccc aacgaagaca agatctgctt tttgcttgta ctgggtctct ctggttagac    2880
cagatctgag cctgggagct ctctggctaa ctagggaacc cactgcttaa gcctcaataa    2940
agcttgcctt gagtgcttca agtagtgtgt gcccgtctgt tgtgtgactc tggtaactag    3000
agatccctca gacccttta gtcagtgtgg aaaatctcta gcagtggcgc ccgaacaggg    3060
acttgaaagc gaaagggaaa ccagaggagc tctctcgacg caggactcgg cttgctgaag    3120
cgcgcacggc aagaggcgag gggcggcgac tggtgagtac gccaaaaatt ttgactagcg    3180
gaggctagaa ggagagagat gggtgcgaga gcgtcagtat taagcggggg agaattagat    3240
cgcgatggga aaaaattcgg ttaaggccag ggggaaagaa aaaatataaa ttaaaacata    3300
tagtatgggc aagcagggag ctagaacgat tcgcagttaa tcctggcctg ttagaaacat    3360
cagaaggctg tagacaaata ctgggacagc tacaaccatc ccttcagaca ggatcagaag    3420
aacttagatc attatataat acagtagcaa ccctctattg tgtgcatcaa aggatagaga    3480
taaaagacac caaggaagct ttagacaaga tagaggaaga gcaaaacaaa agtaagacca    3540
ccgcacagca agcggccgct gatcttcaga cctggaggag gagatatgag ggacaattgg    3600
agaagtgaat tatataaata taagtagta aaaattgaac cattaggagt agcacccacc    3660
aaggcaaaga gaagagtggt gcagagagaa aaaagagcag tgggaatagg agctttgttc    3720
cttgggttct tgggagcagc aggaagcact atgggcgcag cgtcaatgac gctgacggta    3780
caggccagac aattattgtc tggtatagtg cagcagcaga acaatttgct gagggctatt    3840
gaggcgcaac agcatctgtt gcaactcaca gtctggggca tcaagcagct ccaggcaaga    3900
atcctggctg tggaaagata cctaaaggat caacagctcc tggggatttg gggttgctct    3960
ggaaaactca tttgcaccac tgctgtgcct tggaatgcta gttggagtaa taaatctctg    4020
gaacagattt ggaatcacac gacctggatg gagtgggaca gagaaattaa caattacaca    4080
agcttaatac actccttaat tgaagaatcg caaaaccagc aagaaaagaa tgaacaagaa    4140
ttattggaat tagataaatg ggcaagtttg tggaattggt ttaacataac aaattggctg    4200
tggtatataa aattattcat aatgatagta ggaggcttgg taggtttaag aatagttttt    4260
gctgtacttt ctatagtgaa tagagttagg cagggatatt caccattatc gtttcagacc    4320
cacctcccaa ccccgagggg acccgacagg cccgaaggaa tagaagaaga aggtggagag    4380
agagacagag acagatccat tcgattagtg aacggatcca gacatgataa gatacattga    4440
tgagtttgga caaaccacaa ctagaatgca gtgaaaaaaa tgctttattt gtgaaatttg    4500
tgatgctatt gctttatttg taaccattat aagctgcaat aaacaagtta acaacaacaa    4560
ttgcattcat tttatgtttc aggttcaggg ggagatgtgg gaggtttttt aaagcaagta    4620
aaacctctac aaatgtggta atcccgcccc taactccgcc catcccgccc ctaactccgc    4680
ccagttccgc ccattctccg ccccatggct gactaatttt ttttatttat gcagaggccg    4740
aggccgcctc ggcctctgag ctattccaga agtagtgagg aggcttttttt ggaggcctag    4800
```

```
ggacgtaccc aattcgccct atagtgagtc gtattacgcg cgctcactgg ccgtcgtttt    4860
acaacgtcgt gactgggaaa accctggcgt tacccaactt aatcgccttg cagcacatcc    4920
cccttccgcc agctggcgta atagcgaaga ggcccgcacc gatcgccctt cccaacagtt    4980
gcgcagcctg aatggcgaat ggcgcgacgc gcccctgtagc ggcgcattaa gcgcggcggg    5040
tgtggtggtt acgcgcagcg tgaccgctac acttgccagc gccctagcgc ccgctccttt    5100
cgctttcttc ccttcctttc tcgccacgtt cgccggcttt ccccgtcaag ctctaaatcg    5160
ggggctccct ttagggttcc gatttagtgc tttacggcac ctcgacccca aaaaacttga    5220
ttagggtgat ggttcacgta gtgggccatc gccctgatag acggtttttc gccctttgac    5280
gttggagtcc acgttcttta atagtggact cttgttccaa actggaacaa cactcaaccc    5340
tatctcggtc tattcttttg atttataagg gattttgccg atttcggcct attggttaaa    5400
aaatgagctg atttaacaaa aatttaacgc gaattttaac aaaatattaa cgtttacaat    5460
ttcccaggtg gcacttttcg ggaaatgtg cgcggaaccc ctatttgttt attttcctaa    5520
atacattcaa atatgtatcc gctcatgaga caataaccct gataaatgct tcaataatat    5580
tgaaaaagga agagtatgag tattcaacat ttccgtgtcg cccttattcc cttttttgcg    5640
gcattttgcc ttcctgtttt tgctcaccca gaaacgctgg tgaaagtaaa agatgctgaa    5700
gatcagttgg gtgcacgagt gggttacatc gaactggatc tcaacagcgg taagatcctt    5760
gagagttttc gccccgaaga acgttttcca atgatgagca cttttaaagt tctgctatgt    5820
ggcgcggtat tatcccgtat tgacgccggg caagagcaac tcggtcgccg catacactat    5880
tctcagaatg acttggttga gtactcacca gtcacagaaa agcatcttac ggatggcatg    5940
acagtaagag aattatgcag tgctgccata accatgagtg ataacactgc ggccaactta    6000
cttctgacaa cgatcggagg accgaaggag ctaaccgctt ttttgcacaa catgggggat    6060
catgtaactc gccttgatcg ttgggaaccg gagctgaatg aagccatacc aaacgacgag    6120
cgtgacacca cgatgcctgt agcaatggca acaacgttgc gcaaactatt aactggcgaa    6180
ctacttactc tagcttcccg gcaacaatta atagactgga tggaggcgga taaagttgca    6240
ggaccacttc tgcgctcggc ccttccggct ggctggttta ttgctgataa atctggagcc    6300
ggtgagcgtg ggtctcgcgg tatcattgca gcactggggc cagatggtaa gccctcccgt    6360
atcgtagtta tctacacgac ggggagtcag gcaactatgg atgaacgaaa tagacagatc    6420
gctgagatag gtgcctcact gattaagcat tggtaactgt cagaccaagt ttactcatat    6480
atactttaga ttgatttaaa acttcatttt taatttaaaa ggatctaggt gaagatcctt    6540
tttgataatc tcatgaccaa aatcccttaa cgtgagtttt cgttccactg agcgtcagac    6600
cccgtagaaa agatcaaagg atcttcttga gatcctttt ttctgcgcgt aatctgctgc    6660
ttgcaaacaa aaaaaccacc gctaccagcg gtggtttgtt tgccggatca agagctacca    6720
actctttttc cgaaggtaac tggcttcagc agagcgcaga taccaaatac tgtccttcta    6780
gtgtagccgt agttaggcca ccacttcaag aactctgtag caccgcctac atacctcgct    6840
ctgctaatcc tgttaccagt ggctgctgcc agtggcgata agtcgtgtct taccgggttg    6900
gactcaagac gatagttacc ggataaggcg cagcggtcgg gctgaacggg gggttcgtgc    6960
acacagccca gcttggagcg aacgacctac accgaactga gatacctaca gcgtgagcta    7020
tgagaaagcg ccacgcttcc cgaagggaga aaggcggaca ggtatccggt aagcggcagg    7080
gtcggaacag gagagcgcac gagggagctt ccagggggaa acgcctggta tctttatagt    7140
cctgtcgggt ttcgccacct ctgacttgag cgtcgatttt tgtgatgctc gtcaggggg    7200
```

```
cggagcctat ggaaaaacgc cagcaacgcg gccttttac ggttcctggc cttttgctgg    7260
ccttttgctc acatgttctt tcctgcgtta tcccctgatt ctgtggataa ccgtattacc    7320
gcctttgagt gagctgatac cgctcgccgc agccgaacga ccgagcgcag cgagtcagtg    7380
agcgaggaag cggaagagcg cccaatacgc aaaccgcctc tccccgcgcg ttggccgatt    7440
cattaatgca gctggcacga caggtttccc gactggaaag cgggcagtga gcgcaacgca    7500
attaatgtga gttagctcac tcattaggca ccccaggctt tacactttat gcttccggct    7560
cgtatgttgt gtggaattgt gagcggataa caatttcaca caggaaacag ctatgaccat    7620
gattacgcca agcgcgcaat taaccctcac taaagggaac aaaagctgga gctgcaagct    7680
tgcatgctgg                                                           7690

<210> SEQ ID NO 11
<211> LENGTH: 7655
<212> TYPE: DNA
<213> ORGANISM: Artificial sequence
<220> FEATURE:
<223> OTHER INFORMATION: Construct pLTR1.7.671/GAPDH-eGFP-WPRE

<400> SEQUENCE: 11
ccattgcata cgttgtatcc atatcataat atgtacattt atattggctc atgtccaaca      60
ttaccgccat gttgacattg attattgact agttattaat agtaatcaat tacgggtca     120 ttagttcata gcccatatat ggagttccgc gttacataac ttacggtaaa tggcccgcct    180
ggctgaccgc ccaacgaccc ccgcccattg acgtcaataa tgacgtatgt tcccatagta    240
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgacctat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag cagagctcgt    660
ttagtgaacc tggcgcccga acagggactg ctagcgttaa cttttaaaag aaaagggggg    720
attggggggt acagtgcagg ggaaagaata gtagacataa tagcaacaga catacaaact    780
aaagaattac aaaaacaaat tacaaaaatt caaaatttta tcgatcacga gactagcctc    840
gaggatatca gttccccaac tttcccgcct ctcagccttt gaaagaaaga aggggagggg    900
ggcaggccgc gtgcagccgc gagcggtgct gggctccggc tccaattccc catctcagtc    960
gttcccaaag tcctcctgtt tcatccaagc gtgtaagggt ccccgtcctt gactccctag   1020
tgtcctgctg cccacagtcc agtcctggga accagcaccg atcacctccc atcgggccaa   1080
tctcagtccc ttccccccta cgtcgggggcc cacacgctcg gtgcgtgccc agttgaacca   1140
ggcggctgcg gaaaaaaaaa agcggggaga agtagggcc cggctactag cggttttacg   1200
ggcgcacgta gctcaggcct caagaccttg gctgggact ggctgagcct ggcgggaggc   1260
ggggtccgag tcaccgcctg ccgccgcgcc ccgggtttct ataaattgag cccgcagcct   1320
cccgcttcgc tctctgctcc tcctgggatc caccggtcgc caccatggtg agcaagggcg   1380
aggagctgtt caccggggtg gtgcccatcc tggtcgagct ggacggcgac gtaaacggcc   1440
acaagttcag cgtgtccggc gagggcgagg gcgatgccac ctacggcaag ctgaccctga   1500
```

```
agttcatctg caccaccggc aagctgcccg tgccctggcc caccctcgtg accaccctga    1560
cctacggcgt gcagtgcttc agccgctacc ccgaccacat gaagcagcac gacttcttca    1620
agtccgccat gcccgaaggc tacgtccagg agcgcaccat cttcttcaag gacgacggca    1680
actacaagac ccgcgccgag gtgaagttcg agggcgacac cctggtgaac cgcatcgagc    1740
tgaagggcat cgacttcaag gaggacggca acatcctggg gcacaagctg gagtacaact    1800
acaacagcca caacgtctat atcatggccg acaagcagaa gaacggcatc aaggtgaact    1860
tcaagatccg ccacaacatc gaggacggca gcgtgcagct cgccgaccac taccagcaga    1920
acacccccat cggcgacggc cccgtgctgc tgcccgacaa ccactacctg agcacccagt    1980
ccgccctgag caaagacccc aacgagaagc gcgatcacat ggtcctgctg gagttcgtga    2040
ccgccgccgg gatcactctc ggcatggacg agctgtacaa gtaaagcggc cgcgtcgaca    2100
atcaacctct ggattacaaa atttgtgaaa gattgactgg tattcttaac tatgttgctc    2160
cttttacgct atgtggatac gctgctttaa tgcctttgta tcatgctatt gcttcccgta    2220
tggctttcat tttctcctcc ttgtataaat cctggttgct gtctctttat gaggagttgt    2280
ggcccgttgt caggcaacgt ggcgtggtgt gcactgtgtt tgctgacgca acccccactg    2340
gttggggcat tgccaccacc tgtcagctcc tttccgggac tttcgctttc ccctccccta    2400
ttgccacggc ggaactcatc gccgcctgcc ttgcccgctg ctggacaggg gctcggctgt    2460
tgggcactga caattccgtg gtgttgtcgg ggaagctgac gtcctttcca tggctgctcg    2520
cctgtgttgc cacctggatt ctgcgcggga cgtccttctg ctacgtccct tcggccctca    2580
atccagcgga ccttccttcc cgcggcctgc tgccggctct gcggcctctt ccgcgtcttc    2640
gccttcgccc tcagacgagt cggatctccc tttgggccgc ctccccgcct ggaattcgag    2700
ctcggtacct ttaagaccaa tgacttacaa ggcagctgta gatcttagcc acttttaaa    2760 agaaaagggg ggactggaag ggctaattca ctcccaacga agacaagatc tgcttttgc    2820 ttgtactggg tctctctggt tagaccagat ctgagcctgg gagctctctg gctaactagg    2880
gaacccactg cttaagcctc aataaagctt gccttgagtg cttcaagtag tgtgtgcccg    2940
tctgttgtgt gactctggta actagagatc cctcagaccc ttttagtcag tgtggaaaat    3000
ctctagcagt ggcgcccgaa cagggacttg aaagcgaaag ggaaaccaga ggagctctct    3060
cgacgcagga ctcggcttgc tgaagcgcgc acggcaagag gcgaggggcg cgactggtg    3120 agtacgccaa aaattttgac tagcggaggc tagaaggaga gatgggtg cgagagcgtc    3180 agtattaagc gggggagaat tagatcgcga tgggaaaaaa ttcggttaag gccaggggga    3240
aagaaaaaat ataaattaaa acatatagta tgggcaagca gggagctaga acgattcgca    3300
gttaatcctg gcctgttaga acatcagaa ggctgtagac aaatactggg acagctacaa    3360
ccatcccttc agacaggatc agaagaactt agatcattat ataatacagt agcaaccctc    3420
tattgtgtgc atcaaaggat agagataaaa gacaccaagg aagctttaga caagatagag    3480
gaagagcaaa acaaaagtaa gaccaccgca cagcaagcgg ccgctgatct tcagacctgg    3540
aggaggagat atgagggaca attggagaag tgaattatat aaatataaag tagtaaaaat    3600
tgaaccatta ggagtagcac ccaccaaggc aaagagaaga gtggtgcaga gagaaaaaag    3660
agcagtggga ataggagctt tgttccttgg gttcttggga gcagcaggaa gcactatggg    3720
cgcagcgtca atgacgctga cggtacaggc cagacaatta ttgtctggta tagtgcagca    3780
gcagaacaat ttgctgaggg ctattgaggc gcaacagcat ctgttgcaac tcacagtctg    3840
gggcatcaag cagctccagg caagaatcct ggctgtggaa agatacctaa aggatcaaca    3900
```

```
gctcctgggg atttggggtt gctctggaaa actcatttgc accactgctg tgccttggaa   3960
tgctagttgg agtaataaat ctctggaaca gatttggaat cacacgacct ggatggagtg   4020
ggacagagaa attaacaatt acacaagctt aatacactcc ttaattgaag aatcgcaaaa   4080
ccagcaagaa aagaatgaac aagaattatt ggaattagat aaatgggcaa gtttgtggaa   4140
ttggtttaac ataacaaatt ggctgtggta tataaaatta ttcataatga tagtaggagg   4200
cttggtaggt ttaagaatag ttttttgctgt actttctata gtaatagag ttaggcaggg    4260 atattcacca ttatcgtttc agacccacct cccaaccccg aggggacccg acaggcccga   4320
aggaatagaa gaagaaggtg gagagagaga cagagacaga tccattcgat tagtgaacgg   4380
atccagacat gataagatac attgatgagt ttggacaaac cacaactaga atgcagtgaa   4440
aaaaatgctt tatttgtgaa atttgtgatg ctattgcttt atttgtaacc attataagct   4500
gcaataaaca agttaacaac aacaattgca ttcattttat gtttcaggtt cagggggaga   4560
tgtgggaggt tttttaaagc aagtaaaacc tctacaaatg tggtaatccc gcccctaact   4620
ccgcccatcc cgcccctaac tccgcccagt tccgcccatt ctccgcccca tggctgacta   4680 attttttttta tttatgcaga ggccgaggcc gcctcggcct ctgagctatt ccagaagtag   4740
tgaggaggct ttttggagg cctagggacg tacccaattc gccctatagt gagtcgtatt     4800
acgcgcgctc actggccgtc gttttacaac gtcgtgactg ggaaaaccct ggcgttaccc   4860
aacttaatcg ccttgcagca catccccctt tcgccagctg gcgtaatagc gaagaggccc   4920
gcaccgatcg cccttcccaa cagttgcgca gcctgaatgg cgaatggcgc gacgcgccct   4980
gtagcggcgc attaagcgcg gcgggtgtgg tggttacgcg cagcgtgacc gctacacttg   5040
ccagcgccct agcgcccgct cctttcgctt tcttcccttc ctttctcgcc acgttcgccg   5100
gctttccccg tcaagctcta aatcggggc tcccctttagg gttccgattt agtgctttac     5160
ggcacctcga ccccaaaaaa cttgattagg gtgatggttc acgtagtggg ccatcgccct   5220
gatagacggt ttttcgccct ttgacgttgg agtccacgtt ctttaatagt ggactcttgt   5280
tccaaactgg aacaacactc aaccctatct cggtctattc ttttgattta agggattt    5340 tgccgatttc ggcctattgg ttaaaaaatg agctgattta acaaaaattt aacgcgaatt   5400
ttaacaaaat attaacgttt acaatttccc aggtggcact tttcggggaa atgtgcgcgg   5460 aaccccctatt tgtttatttt tctaaataca ttcaaatatg tatccgctca tgagacaata   5520
accctgataa atgcttcaat aatattgaaa aaggaagagt atgagtattc aacatttccg   5580
tgtcgccctt attcccttt tgcggcatt ttgccttcct gttttttgctc acccagaaac    5640 gctggtgaaa gtaaaagatg ctgaagatca gttgggtgca cgagtgggtt acatcgaact   5700
ggatctcaac agcggtaaga tccttgagag ttttcgcccc gaagaacgtt ttccaatgat   5760
gagcactttt aaagttctgc tatgtggcgc ggtattatcc cgtattgacg ccgggcaaga   5820
gcaactcggt cgccgcatac actattctca gaatgacttg gttgagtact caccagtcac   5880
agaaaagcat cttacggatg gcatgacagt aagagaatta tgcagtgctg ccataaccat   5940
gagtgataac actgcggcca acttacttct gacaacgatc ggaggaccga aggagctaac   6000
cgcttttttg cacaacatgg gggatcatgt aactcgcctt gatcgttggg aaccggagct   6060
gaatgaagcc ataccaaacg acgagcgtga caccacgatg cctgtagcaa tggcaacaac   6120
gttgcgcaaa ctattaactg gcgaactact tactctagct tcccggcaac aattaataga   6180
ctggatggag gcggataaag ttgcaggacc acttctgcgc tcggcccttc cggctggctg   6240
```

```
gtttattgct gataaatctg gagccggtga gcgtgggtct cgcggtatca ttgcagcact    6300
ggggccagat ggtaagccct cccgtatcgt agttatctac acgacgggga gtcaggcaac    6360
tatggatgaa cgaaatagac agatcgctga gataggtgcc tcactgatta agcattggta    6420
actgtcagac caagtttact catatatact ttagattgat ttaaaacttc attttttaatt   6480
taaaaggatc taggtgaaga tcctttttga taatctcatg accaaaatcc cttaacgtga    6540
gttttcgttc cactgagcgt cagaccccgt agaaaagatc aaaggatctt cttgagatcc    6600
ttttttttctg cgcgtaatct gctgcttgca acaaaaaaa ccaccgctac cagcggtggt    6660
ttgtttgccg gatcaagagc taccaactct ttttccgaag gtaactggct tcagcagagc    6720
gcagatacca atactgtcc ttctagtgta gccgtagtta ggccaccact tcaagaactc     6780
tgtagcaccg cctacatacc tcgctctgct aatcctgtta ccagtggctg ctgccagtgg    6840
cgataagtcg tgtcttaccg ggttggactc aagacgatag ttaccggata aggcgcagcg    6900
gtcgggctga acggggggtt cgtgcacaca gcccagcttg gagcgaacga cctacaccga    6960
actgagatac ctacagcgtg agctatgaga aagcgccacg cttcccgaag ggagaaaggc    7020
ggacaggtat ccggtaagcg gcagggtcgg aacaggagag cgcacgaggg agcttccagg    7080
gggaaacgcc tggtatcttt atagtcctgt cgggtttcgc cacctctgac ttgagcgtcg    7140
atttttgtga tgctcgtcag gggggcggag cctatggaaa aacgccagca acgcggcctt    7200
tttacggttc ctggccttt gctggccttt tgctcacatg ttctttcctg cgttatcccc     7260
tgattctgtg ataaccgta ttaccgcctt tgagtgagct gataccgctc gccgcagccg     7320
aacgaccgag cgcagcgagt cagtgagcga ggaagcggaa gagcgcccaa tacgcaaacc    7380
gcctctcccc gcgcgttggc cgattcatta atgcagctgg cacgacaggt ttcccgactg    7440
gaaagcgggc agtgagcgca acgcaattaa tgtgagttag ctcactcatt aggcaccca    7500
ggctttacac tttatgcttc cggctcgtat gttgtgtgga attgtgagcg gataacaatt    7560
tcacacagga aacagctatg accatgatta cgccaagcgc gcaattaacc ctcactaaag    7620
ggaacaaaag ctggagctgc aagcttgcat gctgg                               7655

<210> SEQ ID NO 12
<211> LENGTH: 7922
<212> TYPE: DNA
<213> ORGANISM: Artificial sequence
<220> FEATURE:
<223> OTHER INFORMATION: Construct pLTR1.11.0/GAPDH-eGFP-wPRE

<400> SEQUENCE: 12
tggccattgc atacgttgta tccatatcat aatatgtaca tttatattgg ctcatgtcca     60
acattaccgc catgttgaca ttgattattg actagttatt aatagtaatc aattacgggg    120
tcattagttc atagcccata tatggagttc cgcgttacat aacttacggt aaatggcccg    180
cctggctgac cgcccaacga cccccgccca ttgacgtcaa taatgacgta tgttcccata    240
gtaacgccaa tagggacttt ccattgacgt caatgggtgg agtatttacg gtaaactgcc    300
cacttggcag tacatcaagt gtatcatatg ccaagtacgc ccctattga cgtcaatgac     360
ggtaaatggc ccgcctggca ttatgcccag tacatgacct tatgggactt tcctacttgg    420
cagtacatct acgtattagt catcgctatt accatggtga tgcggttttg gcagtacatc    480
aatgggcgtg atagcggttt tgactcacgg ggatttccaa gtctccaccc cattgacgtc    540
aatgggagtt tgttttggca ccaaaatcaa cgggactttc caaaatgtcg taacaactcc    600
gccccattga cgcaaatggg cggtaggcgt gtacggtggg aggtctatat aagcagagct    660
```

```
cgtttagtga accggggtct ctctggttag accagatctg agcctgggag ctctctggct      720
aactagggaa cccactgctt aagcctcaat aaagcttgcc ttgagtgctt caagtagtgt      780
gtgcccgtct gttgtgtgac tctggtaact agagatccct cagacccttt tagtcagtgt      840
ggaaaatctc tagcagtggc gcccgaacag ggacttgaaa gcgaaaggga accagagga      900
gctctctcga cgcaggactc ggcttgctga agcgcgcacg gcaagaggcg aggggcggcg      960
actggtgagt acgccaagct agcgttaact tttaaaagaa aaggggggat tgggggggtac     1020
agtgcagggg aaagaatagt agacataata gcaacagaca tacaaactaa agaattacaa     1080
aaacaaatta caaaaattca aaattttatc gatcacgaga ctagcctcga ggatatcagt     1140
tccccaactt tcccgcctct cagcctttga agaaagaaa ggggagggggg caggccgcgt     1200
gcagccgcga gcggtgctgg gctccggctc caattcccca tctcagtcgt tcccaaagtc     1260
ctcctgtttc atccaagcgt gtaagggtcc ccgtccttga ctccctagtg tcctgctgcc     1320
cacagtccag tcctgggaac cagcaccgat cacctcccat cgggccaatc tcagtccctt     1380
cccccctacg tcggggccca cacgctcggt gcgtgcccag ttgaaccagg cggctgcgga     1440
aaaaaaaaag cggggagaaa gtagggcccg gctactagcg gttttacggg cgcacgtagc     1500
tcaggcctca agaccttggg ctgggactgg ctgagcctgg cgggaggcgg ggtccgagtc     1560
accgcctgcc gccgcgcccc cggtttctat aaattgagcc cgcagcctcc cgcttcgctc     1620
tctgctcctc ctgtgatcaa ccggtcgcca ccatggtgag caagggcgag gagctgttca     1680
ccggggtggt gcccatcctg gtcgagctgg acggcgacgt aaacggccac aagttcagcg     1740
tgtccggcga gggcgagggc gatgccacct acggcaagct gaccctgaag ttcatctgca     1800
ccaccggcaa gctgcccgtg ccctggccca cctcgtgac cacctgacc tacggcgtgc     1860
agtgcttcag ccgctacccc gaccacatga agcagcacga cttcttcaag tccgccatgc     1920
ccgaaggcta cgtccaggag cgcaccatct tcttcaagga cgacggcaac tacaagaccc     1980
gcgccgaggt gaagttcgag ggcgacaccc tggtgaaccg catcgagctg aagggcatcg     2040
acttcaagga ggacggcaac atcctggggc acaagctgga gtacaactac aacagccaca     2100
acgtctatat catggccgac aagcagaaga acggcatcaa ggtgaacttc aagatccgcc     2160
acaacatcga ggacggcagc gtgcagctcg ccgaccacta ccagcagaac ccccccatcg     2220
gcgacggccc cgtgctgctg cccgacaacc actacctgag cacccagtcc gccctgagca     2280
aagaccccaa cgagaagcgc gatcacatgg tcctgctgga gttcgtgacc gccgccggga     2340
tcactctcgg catggacgag ctgtacaagt aaagcggccg cgtcgacaat caacctctgg     2400
attacaaaat ttgtgaaaga ttgactggta ttcttaacta tgttgctcct tttacgctat     2460
gtggatacgc tgctttaatg cctttgtatc atgctattgc ttcccgtatg ctttcattt     2520
tctcctcctt gtataaatcc tggttgctgt ctctttatga ggagttgtgg cccgttgtca     2580
ggcaacgtgg cgtggtgtgc actgtgtttg ctgacgcaac ccccactggt tggggcattg     2640
ccaccacctg tcagctcctt tccgggactt tcgctttccc cctccctatt gccacggcgg     2700
aactcatcgc cgcctgcctt gcccgctgct ggacaggggc tcggctgttg gcactgaca     2760
attccgtggt gttgtcgggg aagctgacgt ccttccatg gctgctcgcc tgtgttgcca     2820
cctggattct gcgcgggacg tccttctgct acgtcccttc ggccctcaat ccagcggacc     2880
ttccttcccg cggcctgctg ccggctctgc ggcctcttcc gcgtcttcgc cttcgccctc     2940
agacgagtcg gatctcccctt tgggccgcct ccccgcctgg aattcgagct cggtaccttt     3000
```

```
aagaccaatg acttacaagg cagctgtaga tcttagccac ttttaaaag aaaaggggg    3060
actggaaggg ctaattcact cccaacgaag acaagatctg cttttgctt gtactgggtc    3120
tctctggtta gaccagatct gagcctggga gctctctggc taactaggga acccactgct    3180
taagcctcaa caaagcttgc cttgagtgct tcaagtagtg tgtgcccgtc tgttgtgtga    3240
ctctggtaac tagagatccc tcagacccct ttagtcagtg tggaaaatct ctagcagttg    3300
aaagcgaaag ggaaaccaga ggagctctct cgacgcagga ctcggcttgc tgaagcgcgc    3360
acggcaagag gcgaggggcg cgactggtg agtacgccaa aaattttgac tagcggaggc    3420
tagaaggaga gagatgggtg cgagagcgtc agtattaagc gggggagaat tagatcgcga    3480
tgggaaaaaa ttcggttaag gccagggga aagaaaaaat ataaattaaa acatatagta    3540
tgggcaagca gggagctaga acgattcgca gttaatcctg gcctgttaga acatcagaa    3600
ggctgtagac aaatactggg acagctacaa ccatcccttc agacaggatc agaagaactt    3660
agatcattat ataatacagt agcaaccctc tattgtgtgc atcaaaggat agagataaaa    3720
gacaccaagg aagctttaga caagatagag gaagagcaaa acaaaagtaa gaccaccgca    3780
cagcaagcgg ccgctgatct tcagacctgg aggaggagat atgagggaca attggagaag    3840
tgaattatat aaatataaag tagtaaaaat tgaaccatta ggagtagcac ccaccaaggc    3900
aaagagaaga gtggtgcaga gagaaaaaag agcagtggga ataggagctt tgttccttgg    3960
gttcttggga gcagcaggaa gcactatggg cgcagcgtca atgacgctga cggtacaggc    4020
cagacaatta ttgtctggta tagtgcagca gcagaacaat ttgctgaggg ctattgaggc    4080
gcaacagcat ctgttgcaac tcacagtctg ggcatcaag cagctccagg caagaatcct    4140
ggctgtggaa agatacctaa aggatcaaca gctcctgggg atttggggtt gctctggaaa    4200
actcatttgc accactgctg tgccttggaa tgctagttgg agtaataaat ctctggaaca    4260
gatttggaat cacacgacct ggatggagtg ggacagagaa attaacaatt acacaagctt    4320
aatacactcc ttaattgaag aatcgcaaaa ccagcaagaa aagaatgaac aagaattatt    4380
ggaattagat aaatgggcaa gtttgtggaa ttggtttaac ataacaaatt ggctgtggta    4440
tataaaatta ttcataatga tagtaggagg cttggtaggt ttaagaatag ttttgctgt    4500
actttctata gtgaatagag ttaggcaggg atattcacca ttatcgtttc agacccacct    4560
cccaaccccg aggggacccg acaggcccga aggaatagaa gaagaaggtg gagagagaga    4620
cagagacaga tccattcgat tagtgaacgg atccagacat gataagatac attgatgagt    4680
ttggacaaac cacaactaga atgcagtgaa aaaaatgctt tatttgtgaa atttgtgatg    4740
ctattgcttt atttgtaacc attataagct gcaataaaca agttaacaac aacaattgca    4800
ttcattttat gtttcaggtt caggggagga tgtgggaggt ttttaaagc aagtaaaacc    4860
tctacaaatg tggtaatccc gcccctaact ccgcccatcc cgcccctaac tccgcccagt    4920
tccgcccatt ctccgcccca tggctgacta atttttttta tttatgcaga ggccgaggcc    4980
gcctcggcct ctgagctatt ccagaagtag tgaggaggct ttttggagg cctagggacg    5040
tacccaattc gccctatagt gagtcgtatt acgcgcgctc actggccgtc gttttacaac    5100
gtcgtgactg ggaaaaccct ggcgttaccc aacttaatcg ccttgcagca catcccctt    5160
tcgccagctg gcgtaatagc gaagaggccc gcaccgatcg cccttcccaa cagttgcgca    5220
gcctgaatgg cgaatggcgc gacgcgccct gtagcggcgc attaagcgcg cgggtgtgg    5280
tggttacgcg cagcgtgacc gctacacttg ccagcgccct agcgcccgct cctttcgctt    5340
tcttcccttc ctttctcgcc acgttcgccg gctttccccg tcaagctcta aatcggggg    5400
```

```
tcccttttagg gttccgattt agtgctttac ggcacctcga ccccaaaaaa cttgattagg   5460
gtgatggttc acgtagtggg ccatcgccct gatagacggt ttttcgccct ttgacgttgg   5520
agtccacgtt ctttaatagt ggactcttgt tccaaactgg aacaacactc aaccctatct   5580
cggtctattc ttttgattta tagggatttt tgccgatttc ggcctattgg ttaaaaaatg   5640
agctgattta acaaaaattt aacgcgaatt ttaacaaaat attaacgttt acaatttccc   5700
aggtggcact tttcggggaa atgtgcgcgg aaccccctatt tgtttatttt tctaaataca   5760
ttcaaatatg tatccgctca tgagacaata accctgataa atgcttcaat aatattgaaa   5820
aaggaagagt atgagtattc aacatttccg tgtcgccctt attcccttttt ttgcggcatt   5880 ttgccttcct gttttttgctc acccagaaac gctggtgaaa gtaaaagatg ctgaagatca   5940
gttgggtgca cgagtgggtt acatcgaact ggatctcaac agcggtaaga tccttgagag   6000
ttttcgcccc gaagaacgtt ttccaatgat gagcactttt aaagttctgc tatgtggcgc   6060
ggtattatcc cgtattgacg ccgggcaaga gcaactcggt cgccgcatac actattctca   6120
gaatgacttg gttgagtact caccagtcac agaaaagcat cttacggatg gcatgacagt   6180
aagagaatta tgcagtgctg ccataaccat gagtgataac actgcggcca acttacttct   6240
gacaacgatc ggaggaccga aggagctaac cgcttttttg cacaacatgg gggatcatgt   6300
aactcgcctt gatcgttggg aaccggagct gaatgaagcc ataccaaacg acgagcgtga   6360
caccacgatg cctgtagcaa tggcaacaac gttgcgcaaa ctattaactg gcgaactact   6420
tactctagct tcccggcaac aattaataga ctggatggag gcggataaag ttgcaggacc   6480
acttctgcgc tcggcccttc cggctggctg gtttattgct gataaatctg gagccggtga   6540
gcgtgggtct cgcggtatca ttgcagcact ggggccagat ggtaagccct cccgtatcgt   6600
agttatctac acgacgggga gtcaggcaac tatggatgaa cgaaatagac agatcgctga   6660
gataggtgcc tcactgatta agcattggta actgtcagac caagtttact catatatact   6720
ttagattgat ttaaaacttc atttttaatt taaaaggatc taggtgaaga tcctttttga   6780
taatctcatg accaaaatcc cttaacgtga gttttcgttc cactgagcgt cagaccccgt   6840
agaaaagatc aaaggatctt cttgagatcc ttttttttctg cgcgtaatct gctgcttgca   6900
aacaaaaaaa ccaccgctac cagcggtggt ttgtttgccg gatcaagagc taccaactct   6960
ttttccgaag gtaactggct tcagcagagc gcagatacca aatactgtcc ttctagtgta   7020
gccgtagtta ggccaccact tcaagaactc tgtagcaccg cctacatacc tcgctctgct   7080
aatcctgtta ccagtggctg ctgccagtgg cgataagtcg tgtcttaccg ggttggactc   7140
aagacgatag ttaccggata aggcgcagcg gtcgggctga acggggggtt cgtgcacaca   7200
gcccagcttg gagcgaacga cctacaccga actgagatac ctacagcgtg agctatgaga   7260
aagcgccacg cttcccgaag ggagaaaggc ggacaggtat ccggtaagcg cagggtcgg   7320 aacaggagag cgcacgaggg agcttccagg gggaaacgcc tggtatcttt atagtcctgt   7380
cgggtttcgc cacctctgac ttgagcgtcg atttttgtga tgctcgtcag ggggcggag   7440 cctatgaaa aacgccagca acgcggcctt tttacggttc ctggccttttt gctggccttt   7500 tgctcacatg ttctttcctg cgttatcccc tgattctgtg gataaccgta ttaccgcctt   7560
tgagtgagct gataccgctc gccgcagccg aacgaccgag cgcagcgagt cagtgagcga   7620
ggaagcggaa gagcgcccaa tacgcaaacc gcctctcccc gcgcgttggc cgattcatta   7680
atgcagctgg cacgacaggt ttcccgactg gaaagcgggc agtgagcgca acgcaattaa   7740
```

```
tgtgagttag ctcactcatt aggcacccca ggctttacac tttatgcttc cggctcgtat   7800
gttgtgtgga attgtgagcg ataacaatt tcacacagga acagctatg accatgatta    7860 cgccaagcgc gcaattaacc ctcactaaag ggaacaaaag ctggagctgc aagcttgcat   7920
gc                                                                  7922

<210> SEQ ID NO 13
<211> LENGTH: 7922
<212> TYPE: DNA
<213> ORGANISM: Artificial sequence
<220> FEATURE:
<223> OTHER INFORMATION: Construct pLTR1.11.1/GAPDH-eGFP-WPRE

<400> SEQUENCE: 13
ctggccattg catacgttgt atccatatca taatatgtac atttatattg gctcatgtcc     60
aacattaccg ccatgttgac attgattatt gactagttat taatagtaat caattacggg    120
gtcattagtt catagcccat atatggagtt ccgcgttaca taacttacgg taaatggccc    180
gcctggctga ccgcccaacg acccccgccc attgacgtca ataatgacgt atgttcccat    240
agtaacgcca atagggactt tccattgacg tcaatgggtg gagtatttac ggtaaactgc    300
ccacttggca gtacatcaag tgtatcatat gccaagtacg ccccctattg acgtcaatga    360
cggtaaatgg cccgcctggc attatgccca gtacatgacc ttatgggact ttcctacttg    420
gcagtacatc tacgtattag tcatcgctat taccatggtg atgcggtttt ggcagtacat    480
caatgggcgt ggatagcggt ttgactcacg gggatttcca agtctccacc ccattgacgt    540
caatgggagt ttgttttggc accaaaatca acgggacttt ccaaaatgtc gtaacaactc    600
cgccccattg acgcaaatgg gcggtaggcg tgtacggtgg gaggtctata taagcagagc    660
tcgtttagtg aaccggggtc tctctggtta gaccagatct gagcctggga gctctctggc    720
taactaggga acccactgct taagcctcaa taaagcttgc cttgagtgct tcaagtagtg    780
tgtgcccgtc tgttgtgtga ctctggtaac tagagatccc tcagaccctt ttagtcagtg    840
tggaaaatct ctagcagtgg cgcccgaaca gggacttgaa agcgaaaggg aaaccagagg    900
agctctctcg acgcaggact cggcttgctg aagcgcgcac ggcaagaggc gaggggcggc    960
gactggtgag tacgccaagc tagcgttaac ttttaaaaga aaggggggga ttggggggta   1020
cagtgcaggg gaaagaatag tagacataat agcaacagac atacaaacta agaattacaa   1080 aaacaaatt acaaaaattc aaaattttat cgatcacgag actagcctcg aggatatcag   1140
ttccccaact ttcccgcctc tcagcctttg aaagaaagaa aggggagggg gcaggccgcg   1200
tgcagccgcg agcggtgctg ggctccggct ccaattcccc atctcagtcg ttcccaaagt   1260
cctcctgttt catccaagcg tgtaagggtc ccgtccttg actccctagt gtcctgctgc   1320
ccacagtcca gtcctgggaa ccagcaccga tcacctccca tcgggccaat ctcagtccct   1380
tcccccctac gtcggggccc acacgctcgg tgcgtgccca gttgaaccag gcggctgcgg   1440
aaaaaaaaaa gcgggagaa agtagggccc ggctactagc ggttttacgg gcgcacgtag   1500
ctcaggcctc aagaccttgg gctgggactg gctgagcctg gcgggaggcg gggtccgagt   1560
caccgcctgc cgccgcgccc ccggtttcta taaattgagc ccgcagcctc ccgcttcgct   1620
ctctgctcct cctgtgatca accggtcgcc accatggtga gcaagggcga ggagctgttc   1680
accggggtgg tgcccatcct ggtcgagctg gacggcgacg taaacggcca caagttcagc   1740
gtgtccggcg agggcgaggg cgatgccacc tacggcaagc tgaccctgaa gttcatctgc   1800
accaccggca agctgcccgt gccctggccc accctcgtga ccaccctgac ctacggcgtg   1860
```

```
cagtgcttca gccgctaccc cgaccacatg aagcagcacg acttcttcaa gtccgccatg    1920
cccgaaggct acgtccagga gcgcaccatc ttcttcaagg acgacggcaa ctacaagacc    1980
cgcgccgagg tgaagttcga gggcgacacc ctggtgaacc gcatcgagct gaagggcatc    2040
gacttcaagg aggacggcaa catcctgggg cacaagctgg agtacaacta caacagccac    2100
aacgtctata tcatggccga caagcagaag aacggcatca aggtgaactt caagatccgc    2160
cacaacatcg aggacggcag cgtgcagctc gccgaccact accagcagaa caccccatc    2220 ggcgacggcc ccgtgctgct gcccgacaac cactacctga gcacccagtc cgccctgagc    2280
aaagacccca acgagaagcg cgatcacatg gtcctgctgg agttcgtgac cgccgccggg    2340
atcactctcg gcatggacga gctgtacaag taaagcggcc gcgtcgacaa tcaacctctg    2400
gattacaaaa tttgtgaaag attgactggt attcttaact atgttgctcc ttttacgcta    2460
tgtggatacg ctgctttaat gcctttgtat catgctattg cttcccgtat ggctttcatt    2520
ttctcctcct tgtataaatc ctggttgctg tctctttatg aggagttgtg gcccgttgtc    2580
aggcaacgtg gcgtggtgtg cactgtgttt gctgacgcaa ccccactggt tggggcatt    2640 gccaccacct gtcagctcct ttccgggact ttcgctttcc cctccctat tgccacggcg    2700 gaactcatcg ccgcctgcct tgcccgctgc tggacagggg ctcggctgtt gggcactgac    2760
aattccgtgg tgttgtcggg gaagctgacg tcctttccat ggctgctcgc ctgtgttgcc    2820
acctggattc tgcgcgggac gtccttctgc tacgtccctt cggccctcaa tccagcggac    2880
cttccttccc gcggcctgct gccggctctg cggcctcttc cgcgtcttcg ccttcgccct    2940
cagacgagtc ggatctccct ttgggccgcc tccccgcctg gaattcgagc tcggtacctt    3000
taagaccaat gacttacaag gcagctgtag atcttagcca cttttttaaaa gaaaagggg    3060 gactggaagg gctaattcac tcccaacgaa gacaagatct gcttttttgct tgtactgggt    3120 ctctctggtt agaccagatc tgagcctggg agctctctgg ctaactaggg aacccactgc    3180
ttaagcctca ataaagcttg ccttgagtgc ttcaagtagt gtgtgcccgt ctgttgtgtg    3240
actctggtaa ctagagatcc ctcagaccct tttagtcagt gtggaaaatc tctagcagtt    3300
gaaagcgaaa gggaaaccag aggagctctc tcgacgcagg actcggcttg ctgaagcgcg    3360
cacggcaaga ggcgaggggc ggcgactggt gagtacgcca aaaattttga ctagcggagg    3420
ctagaaggag agagatgggt gcgagagcgt cagtattaag cggggagaa ttagatcgcg    3480 atgggaaaaa attcggttaa ggccaggggg aaagaaaaaa tataaattaa acatatagt    3540 atgggcaagc agggagctag aacgattcgc agttaatcct ggcctgttag aaacatcaga    3600
aggctgtaga caaatactgg gacagctaca accatccctt cagacaggat cagaagaact    3660
tagatcatta tataatacag tagcaaccct ctattgtgtg catcaaagga tagagataaa    3720
agacaccaag gaagctttag acaagataga ggaagagcaa aacaaaagta agaccaccgc    3780
acagcaagcg gccgctgatc ttcagacctg gaggaggaga tatgagggac aattggagaa    3840
gtgaattata taaatataaa gtagtaaaaa ttgaaccatt aggagtagca cccaccaagg    3900
caaagagaag agtggtgcag agagaaaaaa gagcagtggg aataggagct tgttccttg    3960 ggttcttggg agcagcagga agcactatgg gcgcagcgtc aatgacgctg acggtacagg    4020
ccagacaatt attgtctggt atagtgcagc agcagaacaa tttgctgagg gctattgagg    4080
cgcaacagca tctgttgcaa ctcacagtct ggggcatcaa gcagctccag gcaagaatcc    4140
tggctgtgga aagataccta aaggatcaac agctcctggg gatttggggt tgctctggaa    4200
```

```
aactcatttg caccactgct gtgccttgga atgctagttg gagtaataaa tctctggaac    4260
agatttggaa tcacacgacc tggatggagt gggacagaga aattaacaat tacacaagct    4320
taatacactc cttaattgaa gaatcgcaaa accagcaaga aaagaatgaa caagaattat    4380
tggaattaga taaatgggca agtttgtgga attggtttaa cataacaaat tggctgtggt    4440
atataaaatt attcataatg atagtaggag gcttggtagg tttaagaata gttttttgctg   4500
tactttctat agtgaataga gttaggcagg gatattcacc attatcgttt cagacccacc    4560
tcccaacccc gaggggaccc gacaggcccg aaggaataga agaagaaggt ggagagagag    4620
acagagacag atccattcga ttagtgaacg gatccagaca tgataagata cattgatgag    4680
tttggacaaa ccacaactag aatgcagtga aaaaaatgct ttatttgtga aatttgtgat    4740
gctattgctt tatttgtaac cattataagc tgcaataaac aagttaacaa caacaattgc    4800
attcatttta tgtttcaggt tcaggggag atgtgggagg ttttttaaag caagtaaaac     4860
ctctacaaat gtggtaatcc cgcccctaac tccgcccatc ccgccccta ctccgcccag     4920
ttccgcccat tctccgcccc atggctgact aattttttt atttatgcag aggccgaggc     4980
cgcctcggcc tctgagctat tccagaagta gtgaggaggc ttttttggag gcctagggac    5040
gtacccaatt cgccctatag tgagtcgtat tacgcgcgct cactggccgt cgttttacaa    5100
cgtcgtgact gggaaaaccc tggcgttacc caacttaatc gccttgcagc acatccccct    5160
ttcgccagct ggcgtaatag cgaagaggcc cgcaccgatc gcccttccca acagttgcgc    5220
agcctgaatg gcgaatggcg cgacgcgccc tgtagcggcg cattaagcgc ggcgggtgtg    5280
gtggttacgc gcagcgtgac cgctacactt gccagcgccc tagcgcccgc tcctttcgct    5340
ttcttccctt cctttctcgc cacgttcgcc ggctttcccc gtcaagctct aaatcggggg    5400
ctccctttag ggttccgatt tagtgcttta cggcacctcg accccaaaaa acttgattag    5460
ggtgatggtt cacgtagtgg gccatcgccc tgatagacgg ttttcgccc tttgacgttg     5520
gagtccacgt tctttaatag tggactcttg ttccaaactg gaacaacact caaccctatc    5580
tcggtctatt cttttgattt ataagggatt ttgccgattt cggcctattg gttaaaaaat    5640
gagctgattt aacaaaaatt taacgcgaat tttaacaaaa tattaacgtt tacaatttcc    5700
caggtggcac ttttcgggga aatgtgcgcg gaacccctat ttgtttattt ttctaaatac    5760
attcaaatat gtatccgctc atgagacaat aaccctgata aatgcttcaa taatattgaa    5820
aaaggaagag tatgagtatt caacatttcc gtgtcgccct tattcccttt tttgcggcat    5880
tttgccttcc tgttttgtgct cacccagaaa cgctggtgaa agtaaaagat gctgaagatc    5940
agttgggtgc acgagtgggt tacatcgaac tggatctcaa cagcggtaag atccttgaga    6000
gttttcgccc cgaagaacgt tttccaatga tgagcacttt taaagttctg ctatgtggcg    6060
cggtattatc ccgtattgac gccgggcaag agcaactcgg tcgccgcata cactattctc    6120
agaatgactt ggttgagtac tcaccagtca cagaaaagca tcttacggat ggcatgacag    6180
taagagaatt atgcagtgct gccataacca tgagtgataa cactgcggcc aacttacttc    6240
tgacaacgat cggaggaccg aaggagctaa ccgcttttt gcacaacatg ggggatcatg     6300
taactcgcct tgatcgttgg gaaccggagc tgaatgaagc cataccaaac gacgagcgtg    6360
acaccacgat gcctgtagca atggcaacaa cgttgcgcaa actattaact ggcgaactac    6420
ttactctagc ttcccggcaa caattaatag actggatgga ggcggataaa gttgcaggac    6480
cacttctgcg ctcggccctt ccggctggct ggtttattgc tgataaatct ggagccggtg    6540
agcgtgggtc tcgcggtatc attgcagcac tggggccaga tggtaagccc tcccgtatcg    6600
```

```
tagttatcta cacgacgggg agtcaggcaa ctatggatga acgaaataga cagatcgctg    6660
agataggtgc ctcactgatt aagcattggt aactgtcaga ccaagtttac tcatatatac    6720
tttagattga tttaaaactt catttttaat ttaaaaggat ctaggtgaag atcctttttg    6780
ataatctcat gaccaaaatc ccttaacgtg agttttcgtt ccactgagcg tcagaccccg    6840
tagaaaagat caaaggatct tcttgagatc ctttttttct gcgcgtaatc tgctgcttgc    6900
aaacaaaaaa accaccgcta ccagcggtgg tttgtttgcc ggatcaagag ctaccaactc    6960
tttttccgaa ggtaactggc ttcagcagag cgcagatacc aaatactgtc cttctagtgt    7020
agccgtagtt aggccaccac ttcaagaact ctgtagcacc gcctacatac ctcgctctgc    7080
taatcctgtt accagtggct gctgccagtg gcgataagtc gtgtcttacc gggttggact    7140
caagacgata gttaccggat aaggcgcagc ggtcgggctg aacggggggt cgtgcacac    7200 agcccagctt ggagcgaacg acctacaccg aactgagata cctacagcgt gagctatgag    7260
aaagcgccac gcttcccgaa gggagaaagg cggacaggta tccggtaagc ggcagggtcg    7320
gaacaggaga gcgcacgagg gagcttccag ggggaaacgc ctggtatctt tatagtcctg    7380
tcgggtttcg ccacctctga cttgagcgtc gatttttgtg atgctcgtca ggggggcgga    7440
gcctatggaa aaacgccagc aacgcggcct ttttacggtt cctggccttt tgctggcctt    7500
ttgctcacat gttctttcct gcgttatccc ctgattctgt ggataaccgt attaccgcct    7560
ttgagtgagc tgataccgct cgccgcagcc gaacgaccga gcgcagcgag tcagtgagcg    7620
aggaagcgga gagcgcccca atacgcaaac cgcctctccc cgcgcgttgg ccgattcatt    7680
aatgcagctg gcacgacagg tttcccgact ggaaagcggg cagtgagcgc aacgcaatta    7740
atgtgagtta gctcactcat taggcacccc aggctttaca ctttatgctt ccggctcgta    7800
tgttgtgtgg aattgtgagc ggataacaat ttcacacagg aaacagctat gaccatgatt    7860
acgccaagcg cgcaattaac cctcactaaa gggaacaaaa gctggagctg caagcttgca    7920
tg                                                                  7922
```

<210> SEQ ID NO 14
<211> LENGTH: 7757
<212> TYPE: DNA
<213> ORGANISM: Artificial sequence
<220> FEATURE:
<223> OTHER INFORMATION: Construct pLTR1.13.0/GAPDH-eGFP-WPRE

<400> SEQUENCE: 14

```
taatcaatta cggggtcatt agttcatagc ccatatatgg agttccgcgt tacataactt      60
acggtaaatg gcccgcctgg ctgaccgccc aacgaccccc gcccattgac gtcaataatg     120
acgtatgttc ccatagtaac gccaataggg actttccatt gacgtcaatg ggtggagtat     180
ttacggtaaa ctgcccactt ggcagtacat caagtgtatc atatgccaag tacgccccct     240
attgacgtca atgacggtaa atggcccgcc tggcattatg cccagtacat gaccttatgg     300
gactttccta cttggcagta catctacgta ttagtcatcg ctattaccat ggtgatgcgg     360
ttttggcagt acatcaatgg gcgtggatag cggtttgact cacggggatt tccaagtctc     420 cacccccattg acgtcaatgg gagtttgttt tggcaccaaa atcaacggga ctttccaaaa     480
tgtcgtaaca actccgcccc attgacgcaa atgggcggta ggcgtgtacg gtgggaggtc     540
tatataagca gagctcgttt agtgaacctg gcgcccgaac agggacttga aagcgaaagg     600
gaaaccagag gagctctctc gacgcaggac tcggcttgct gaagcgcgca cggcaagagg     660
```

```
cgaggggcgg cgactggtga gtacgccaag ctagcgttaa cttttaaaag aaaaggggggg      720 attgggggggt acagtgcagg ggaaagaata gtagacataa tagcaacaga catacaaact      780
aaagaattac aaaaacaaat tacaaaaatt caaaatttta tcgatcacga gactagcctc      840
gaggatatca gttccccaac tttcccgcct ctcagccttt gaaagaaaga aaggggaggg      900
ggcaggccgc gtgcagccgc gagcggtgct gggctccggc tccaattccc catctcagtc      960
gttcccaaag tcctcctgtt tcatccaagc gtgtaagggt ccccgtcctt gactccctag     1020
tgtcctgctg cccacagtcc agtcctggga accagcaccg atcacctccc atcgggccaa     1080
tctcagtccc ttccccccta cgtcgggggcc cacacgctcg gtgcgtgccc agttgaacca     1140
ggcggctgcg gaaaaaaaaa agcggggaga aagtagggcc cggctactag cggttttacg     1200
ggcgcacgta gctcaggcct caagaccttg ggctgggact ggctgagcct ggcgggaggc     1260
ggggtccgag tcaccgcctg ccgccgcgcc cccggtttct ataaattgag cccgcagcct     1320
cccgcttcgc tctctgctcc tcctgggatc caccggtcgc caccatggtg agcaagggcg     1380
aggagctgtt caccggggtg gtgcccatcc tggtcgagct ggacggcgac gtaaacggcc     1440
acaagttcag cgtgtccggc gagggcgagg gcgatgccac ctacggcaag ctgaccctga     1500
agttcatctg caccaccggc aagctgcccg tgccctggcc caccctcgtg accaccctga     1560
cctacggcgt gcagtgcttc agccgctacc ccgaccacat gaagcagcac gacttcttca     1620
agtccgccat gcccgaaggc tacgtccagg agcgcaccat cttcttcaag gacgacggca     1680
actacaagac ccgcgccgag gtgaagttcg agggcgacac cctggtgaac cgcatcgagc     1740
tgaagggcat cgacttcaag gaggacggca acatcctggg gcacaagctg gagtacaact     1800
acaacagcca caacgtctat atcatggccg acaagcagaa gaacggcatc aaggtgaact     1860
tcaagatccg ccacaacatc gaggacggca gcgtgcagct cgccgaccac taccagcaga     1920
acacccccat cggcgacggc cccgtgctgc tgcccgacaa ccactacctg agcacccagt     1980 ccgcccctgag caaagacccc aacgagaagc gcgatcacat ggtcctgctg gagttcgtga     2040
ccgccgccgg gatcactctc ggcatggacg agctgtacaa gtaaagcggc cgcgtcgaca     2100
atcaacctct ggattacaaa atttgtgaaa gattgactgg tattcttaac tatgttgctc     2160
cttttacgct atgtggatac gctgctttaa tgccttgta tcatgctatt gcttcccgta     2220
tggctttcat tttctcctcc ttgtataaat cctggttgct gtctctttat gaggagttgt     2280
ggcccgttgt caggcaacgt ggcgtggtgt gcactgtgtt tgctgacgca accccactg     2340 gttggggcat tgccaccacc tgtcagctcc tttccgggac tttcgctttc ccctcccta     2400 ttgccacggc ggaactcatc gccgcctgcc ttgcccgctg ctggacaggg gctcggctgt     2460
tgggcactga caattccgtg gtgttgtcgg ggaagctgac gtccttcca tggctgctcg     2520 cctgtgttgc cacctggatt ctgcgcggga cgtccttctg ctacgtccct tcggccctca     2580
atccagcgga ccttccttcc gcggcctgc tgccggctct gcggcctctt ccgcgtcttc     2640
gccttcgccc tcagacgagt cggatctccc tttgggccgc ctccccgcct ggaattcgag     2700
ctcggtacct ttaagaccaa tgacttacaa ggcagctgta gatcttagcc acttttaaaa     2760
agaaaagggg ggactggaag ggctaattca ctcccaacga agacaagatc tgcttttttgc     2820 ttgtactggg tctctctggt tagaccagat ctgagcctgg gagctctctg gctaactagg     2880
gaacccactg cttaagcctc aataaagctt gccttgagtg cttcaagtag tgtgtgcccg     2940
tctgttgtgt gactctggta actagagatc cctcagaccc ttttagtcag tgtggaaaat     3000
ctctagcagt ggcgcccgaa cagggacttg aaagcgaaag ggaaaccaga ggagctctct     3060
```

| | |
|---|---|
| cgacgcagga ctcggcttgc tgaagcgcgc acggcaagag gcgaggggcg gcgactggtg | 3120 |
| agtacgccaa aaattttgac tagcggaggc tagaaggaga gagatgggtg cgagagcgtc | 3180 |
| agtattaagc gggggagaat tagatcgcga tgggaaaaaa ttcggttaag gccaggggga | 3240 |
| aagaaaaaat ataaattaaa acatatagta tgggcaagca gggagctaga acgattcgca | 3300 |
| gttaatcctg gcctgttaga acatcagaa ggctgtagac aaatactggg acagctacaa | 3360 |
| ccatcccttc agacaggatc agaagaactt agatcattat ataatacagt agcaaccctc | 3420 |
| tattgtgtgc atcaaaggat agagataaaa gacaccaagg aagctttaga caagatagag | 3480 |
| gaagagcaaa acaaaagtaa gaccaccgca cagcaagcgg ccgctgatct tcagacctgg | 3540 |
| aggaggagat atgagggaca attggagaag tgaattatat aaatataaag tagtaaaaat | 3600 |
| tgaaccatta ggagtagcac ccaccaaggc aaagagaaga gtggtgcaga gagaaaaaag | 3660 |
| agcagtggga ataggagctt tgttccttgg gttcttggga gcagcaggaa gcactatggg | 3720 |
| cgcagcgtca atgacgctga cggtacaggc cagacaatta ttgtctggta tagtgcagca | 3780 |
| gcagaacaat ttgctgaggg ctattgaggc gcaacagcat ctgttgcaac tcacagtctg | 3840 |
| gggcatcaag cagctccagg caagaatcct ggctgtggaa agatacctaa aggatcaaca | 3900 |
| gctcctgggg atttggggtt gctctggaaa actcatttgc accactgctg tgccttggaa | 3960 |
| tgctagttgg agtaataaat ctctggaaca gatttggaat cacacgacct ggatggagtg | 4020 |
| ggacagagaa attaacaatt acacaagctt aatacactcc ttaattgaag aatcgcaaaa | 4080 |
| ccagcaagaa aagaatgaac aagaattatt ggaattagat aaatgggcaa gtttgtggaa | 4140 |
| ttggtttaac ataacaaatt ggctgtggta tataaaatta ttcataatga tagtaggagg | 4200 |
| cttggtaggt ttaagaatag ttttgctgt actttctata gtgaatagag ttaggcaggg | 4260 |
| atattcacca ttatcgtttc agacccacct cccaaccccg aggggacccg acaggcccga | 4320 |
| aggaatagaa gaagaaggtg gagagagaga cagagacaga tccattcgat tagtgaacgg | 4380 |
| atccagacat gataagatac attgatgagt ttggacaaac cacaactaga atgcagtgaa | 4440 |
| aaaaatgctt tatttgtgaa atttgtgatg ctattgcttt atttgtaacc attataagct | 4500 |
| gcaataaaca agttaacaac aacaattgca ttcattttat gtttcaggtt cagggggaga | 4560 |
| tgtgggaggt tttttaaagc aagtaaaacc tctacaaatg tggtaatccc gcccctaact | 4620 |
| ccgcccatcc cgcccctaac tccgcccagt tccgcccatt ctccgcccca tggctgacta | 4680 |
| attttttttta tttatgcaga ggccgaggcc gcctcggcct ctgagctatt ccagaagtag | 4740 |
| tgaggaggct ttttggagg cctagggacg tacccaattc gccctatagt gagtcgtatt | 4800 |
| acgcgcgctc actggccgtc gttttacaac gtcgtgactg ggaaaaccct ggcgttaccc | 4860 |
| aacttaatcg ccttgcagca catccccctt tcgccagctg gcgtaatagc gaagaggccc | 4920 |
| gcaccgatcg cccttcccaa cagttgcgca gcctgaatgg cgaatggcgc gacgcgccct | 4980 |
| gtagcggcgc attaagcgcg gcgggtgtgg tggttacgcg cagcgtgacc gctacacttg | 5040 |
| ccagcgccct agcgcccgct cctttcgctt tcttcccttc ctttctcgcc acgttcgccg | 5100 |
| gctttccccg tcaagctcta aatcgggggc tccctttagg gttccgattt agtgctttac | 5160 |
| ggcacctcga ccccaaaaaa cttgattagg gtgatggttc acgtagtggg ccatcgccct | 5220 |
| gatagacggt ttttcgccct ttgacgttgg agtccacgtt ctttaatagt ggactcttgt | 5280 |
| tccaaactgg aacaacactc aaccctatct cggtctattc ttttgattta agggattt | 5340 |
| tgccgatttc ggcctattgg ttaaaaaatg agctgattta acaaaaattt aacgcgaatt | 5400 |

```
ttaacaaaat attaacgttt acaatttccc aggtggcact tttcggggaa atgtgcgcgg    5460
aaccccctatt tgtttatttt tctaaataca ttcaaatatg tatccgctca tgagacaata   5520
accctgataa atgcttcaat aatattgaaa aggaagagt atgagtattc aacatttccg    5580
tgtcgccctt attccttttt ttgcggcatt ttgccttcct gttttttgctc acccagaaac  5640
gctggtgaaa gtaaaagatg ctgaagatca gttgggtgca cgagtgggtt acatcgaact   5700
ggatctcaac agcggtaaga tccttgagag ttttcgcccc gaagaacgtt ttccaatgat   5760
gagcactttt aaagttctgc tatgtggcgc ggtattatcc cgtattgacg ccgggcaaga   5820
gcaactcggt cgccgcatac actattctca gaatgacttg gttgagtact caccagtcac   5880
agaaaagcat cttacggatg gcatgacagt aagagaatta tgcagtgctg ccataaccat   5940
gagtgataac actgcggcca acttacttct gacaacgatc ggaggaccga aggagctaac   6000
cgcttttttg cacaacatgg ggatcatgt aactcgcctt gatcgttggg aaccggagct   6060
gaatgaagcc ataccaaacg acgagcgtga ccacgatg cctgtagcaa tggcaacaac    6120
gttgcgcaaa ctattaactg gcgaactact tactctagct tcccggcaac aattaataga   6180
ctggatggag gcggataaag ttgcaggacc acttctgcgc tcggcccttc cggctggctg   6240
gtttattgct gataaatctg gagccggtga gcgtgggtct cgcggtatca ttgcagcact   6300
ggggccagat ggtaagccct cccgtatcgt agttatctac acgacgggga gtcaggcaac   6360
tatgatgaa cgaaatagac agatcgctga gataggtgcc tcactgatta gcattggta    6420
actgtcagac caagtttact catatatact ttagattgat ttaaaacttc atttttaatt   6480
taaaaggatc taggtgaaga tcctttttga taatctcatg accaaaatcc cttaacgtga   6540
gttttcgttc cactgagcgt cagaccccgt agaaaagatc aaaggatctt cttgagatcc   6600
tttttttctg cgcgtaatct gctgcttgca acaaaaaaa ccaccgctac cagcggtggt    6660
ttgtttgccg gatcaagagc taccaactct ttttccgaag gtaactggct tcagcagagc   6720
gcagatacca aatactgtcc ttctagtgta gccgtagtta ggccaccact tcaagaactc   6780
tgtagcaccg cctacatacc tcgctctgct aatcctgtta ccagtggctg ctgccagtgg   6840
cgataagtcg tgtcttaccg ggttggactc aagacgatag ttaccggata aggcgcagcg   6900
gtcgggctga acggggggtt cgtgcacaca gcccagcttg gagcgaacga cctacaccga   6960
actgagatac ctacagcgtg agctatgaga aagcgccacg cttcccgaag ggagaaaggc   7020
ggacaggtat ccggtaagcg gcagggtcgg aacaggagag cgcacgaggg agcttccagg   7080
gggaaacgcc tggtatcttt atagtcctgt cgggtttcgc cacctctgac ttgagcgtcg   7140
attttttgtga tgctcgtcag gggggcggag cctatggaaa aacgccagca acgcggcctt   7200
tttacggttc ctggcctttt gctggccttt tgctcacatg ttctttcctg cgttatcccc   7260
tgattctgtg gataaccgta ttaccgcctt tgagtgagct gataccgctc gccgcagccg   7320
aacgaccgag cgcagcgagt cagtgagcga ggaagcggaa gagcgcccaa tacgcaaacc   7380
gcctctcccc gcgcgttggc cgattcatta atgcagctgg cacgacaggt ttcccgactg   7440
gaaagcgggc agtgagcgca acgcaattaa tgtgagttag ctcactcatt aggcaccca   7500
ggctttacac tttatgcttc cggctcgtat gttgtgtgga attgtgagcg gataacaatt   7560
tcacacagga aacagctatg accatgatta cgccaagcgc gcaattaacc ctcactaaag   7620
ggaacaaaag ctggagctgc aagcttgcat gctggccatt gcatacgttg tatccatatc   7680
ataatatgta catttatatt ggctcatgtc caacattacc gccatgttga cattgattat   7740
tgactagtta ttaatag                                                   7757
```

<210> SEQ ID NO 15
<211> LENGTH: 7676
<212> TYPE: DNA
<213> ORGANISM: Artificial sequence
<220> FEATURE:
<223> OTHER INFORMATION: Construct pLTR1.13.1/GAPDH-eGFP-WPRE

<400> SEQUENCE: 15

| | | | | | |
|---|---|---|---|---|---|
| tatcataata | tgtacattta | tattggctca | tgtccaacat | taccgccatg | ttgacattga | 60 |
| ttattgacta | gttattaata | gtaatcaatt | acggggtcat | tagttcatag | cccatatatg | 120 |
| gagttccgcg | ttacataact | tacggtaaat | ggcccgcctg | gctgaccgcc | caacgacccc | 180 |
| cgcccattga | cgtcaataat | gacgtatgtt | cccatagtaa | cgccaatagg | gactttccat | 240 |
| tgacgtcaat | gggtggagta | tttacggtaa | actgcccact | tggcagtaca | tcaagtgtat | 300 |
| catatgccaa | gtacgccccc | tattgacgtc | aatgacggta | aatggcccgc | ctggcattat | 360 |
| gcccagtaca | tgaccttatg | gactttcct | acttggcagt | acatctacgt | attagtcatc | 420 |
| gctattacca | tggtgatgcg | gttttggcag | tacatcaatg | ggcgtggata | gcggtttgac | 480 |
| tcacgggat | ttccaagtct | ccaccccatt | gacgtcaatg | ggagtttgtt | ttggcaccaa | 540 |
| aatcaacggg | actttccaaa | atgtcgtaac | aactccgccc | cattgacgca | aatgggcggt | 600 |
| aggcgtgtac | ggtgggaggt | ctatataagc | agagctcgtt | tagtgaacct | ggcgcccgaa | 660 |
| cagggactgg | cgactggtga | gtacgccaag | ctagcgttaa | cttttaaaag | aaaaggggg | 720 |
| attgggggt | acagtgcagg | ggaaagaata | gtagacataa | tagcaacaga | catacaaact | 780 |
| aaagaattac | aaaaacaaat | tacaaaaatt | caaaattta | tcgatcacga | gactagcctc | 840 |
| gaggatatca | gttccccaac | tttcccgcct | ctcagccttt | gaaagaaaga | aggggaggg | 900 |
| ggcaggccgc | gtgcagccgc | gagcggtgct | gggctccggc | tccaattccc | catctcagtc | 960 |
| gttcccaaag | tcctcctgtt | tcatccaagc | gtgtaagggt | ccccgtcctt | gactccctag | 1020 |
| tgtcctgctg | cccacagtcc | agtcctggga | accagcaccg | atcacctccc | atcgggccaa | 1080 |
| tctcagtccc | ttcccccta | cgtcggggcc | cacacgctcg | gtgcgtgccc | agttgaacca | 1140 |
| ggcggctgcg | gaaaaaaaa | agcggggaga | agtagggcc | cggctactag | cggttttacg | 1200 |
| ggcgcacgta | gctcaggcct | caagaccttg | gctgggact | ggctgagcct | ggcgggaggc | 1260 |
| ggggtccgag | tcaccgcctg | ccgccgcgcc | ccggtttct | ataaattgag | cccgcagcct | 1320 |
| cccgcttcgc | tctctgctcc | tctgggatc | caccggtcgc | caccatggtg | agcaagggcg | 1380 |
| aggagctgtt | caccggggtg | gtgcccatcc | tggtcgagct | ggacggcgac | gtaaacggcc | 1440 |
| acaagttcag | cgtgtccggc | gagggcgagg | gcgatgccac | ctacggcaag | ctgaccctga | 1500 |
| agttcatctg | caccaccggc | aagctgcccg | tgcctggcc | cacctcgtg | accaccctga | 1560 |
| cctacggcgt | gcagtgcttc | agccgctacc | ccgaccacat | gaagcagcac | gacttcttca | 1620 |
| agtccgccat | gcccgaaggc | tacgtccagg | agcgcaccat | cttcttcaag | gacgacggca | 1680 |
| actacaagac | ccgcgccgag | gtgaagttcg | agggcgacac | cctggtgaac | cgcatcgagc | 1740 |
| tgaagggcat | cgacttcaag | gaggacggca | acatcctggg | gcacaagctg | gagtacaact | 1800 |
| acaacagcca | caacgtctat | atcatggccg | acaagcagaa | gaacggcatc | aaggtgaact | 1860 |
| tcaagatccg | ccacaacatc | gaggacggca | gcgtgcagct | cgccgaccac | taccagcaga | 1920 |
| acacccccat | cggcgacggc | cccgtgctgc | tgcccgacaa | ccactacctg | agcacccagt | 1980 |
| ccgccctgag | caaagacccc | aacgagaagc | gcgatcacat | ggtcctgctg | gagttcgtga | 2040 |

```
ccgccgccgg gatcactctc ggcatggacg agctgtacaa gtaaagcggc cgcgtcgaca    2100
atcaacctct ggattacaaa atttgtgaaa gattgactgg tattcttaac tatgttgctc    2160
cttttacgct atgtggatac gctgctttaa tgcctttgta tcatgctatt gcttcccgta    2220 tggcttcat ttctcctcc ttgtataaat cctggttgct gtctcttat gaggagttgt       2280 ggcccgttgt caggcaacgt ggcgtggtgt gcactgtgtt tgctgacgca acccccactg    2340 gttgggcat tgccaccacc tgtcagctcc tttcgggac tttcgcttc ccctcccta        2400 ttgccacggc ggaactcatc gccgcctgcc ttgcccgctg ctggacaggg gctcggctgt    2460
tgggcactga caattccgtg gtgttgtcgg ggaagctgac gtccttcca tggctgctcg     2520 cctgtgttgc cacctggatt ctgcgcggga cgtccttctg ctacgtccct tcggccctca    2580
atccagcgga ccttccttcc gcggcctgc tgccggctct gcggcctctt ccgcgtcttc     2640
gccttcgccc tcagacgagt cggatctccc tttgggccgc ctccccgcct ggaattcgag    2700
ctcggtacct ttaagaccaa tgacttacaa ggcagctgta gatcttagcc acttttaaa    2760 agaaaagggg ggactggaag ggctaattca ctcccaacga agacaagatc tgcttttgc     2820 ttgtactggg tctctctggt tagaccagat ctgagcctgg gagctctctg gctaactagg    2880
gaacccactg cttaagcctc aataaagctt gccttgagtg cttcaagtag tgtgtgcccg    2940
tctgttgtgt gactctggta actagagatc cctcagaccc ttttagtcag tgtggaaaat    3000
ctctagcagt ggcgcccgaa cagggacttg aaagcgaaag ggaaaccaga ggagctctct    3060
cgacgcagga ctcggcttgc tgaagcgcgc acggcaagag gcgaggggcg cgactggtg     3120 agtacgccaa aaattttgac tagcggaggc tagaaggaga gagatgggtg cgagagcgtc    3180
agtattaagc gggggagaat tagatcgcga tgggaaaaaa ttcggttaag gccaggggga    3240
aagaaaaaat ataaattaaa acatatagta tgggcaagca gggagctaga acgattcgca    3300
gttaatcctg gcctgttaga aacatcagaa ggctgtagac aaatactggg acagctacaa    3360
ccatcccttc agacaggatc agaagaactt agatcattat ataatacagt agcaaccctc    3420
tattgtgtgc atcaaaggat agagataaaa gacaccaagg aagctttaga caagatagag    3480
gaagagcaaa acaaaagtaa gaccaccgca cagcaagcgg ccgctgatct tcagacctgg    3540
aggaggagat atgagggaca attggagaag tgaattatat aaatataaag tagtaaaaat    3600
tgaaccatta ggagtagcac ccaccaaggc aaagagaaga gtggtgcaga gagaaaaaag    3660
agcagtggga ataggagctt tgttccttgg gttcttggga gcagcaggaa gcactatggg    3720
cgcagcgtca atgacgctga cggtacaggc cagacaatta ttgtctggta tagtgcagca    3780
gcagaacaat ttgctgaggg ctattgaggc gcaacagcat ctgttgcaac tcacagtctg    3840
gggcatcaag cagctccagg caagaatcct ggctgtggaa agatacctaa aggatcaaca    3900
gctcctgggg atttggggtt gctctggaaa actcatttgc accactgctg tgccttggaa    3960
tgctagttgg agtaataaat ctctggaaca gatttggaat cacacgacct ggatggagtg    4020
ggacagagaa attaacaatt acacaagctt aatacactcc ttaattgaag aatcgcaaaa    4080
ccagcaagaa aagaatgaac aagaattatt ggaattagat aaatgggcaa gtttgtggaa    4140
ttggtttaac ataacaaatt ggctgtggta tataaaatta ttcataatga tagtaggagg    4200
cttggtaggt ttaagaatag tttttgctgt actttctata gtgaatagag ttaggcaggg    4260
atattcacca ttatcgtttc agacccacct cccaaccccg aggggacccg acaggcccga    4320
aggaatagaa gaagaaggtg gagagagaga cagagacaga tccattcgat tagtgaacgg    4380
atccagacat gataagatac attgatgagt ttggacaaac cacaactaga atgcagtgaa    4440
```

```
aaaaatgctt tatttgtgaa atttgtgatg ctattgcttt atttgtaacc attataagct    4500
gcaataaaca agttaacaac aacaattgca ttcattttat gtttcaggtt caggggagaa    4560
tgtgggaggt tttttaaagc aagtaaaacc tctacaaatg tggtaatccc gcccctaact    4620
ccgcccatcc cgcccctaac tccgcccagt tccgcccatt ctccgcccca tggctgacta    4680 attttttta tttatgcaga ggccgaggcc gcctcggcct ctgagctatt ccagaagtag     4740
tgaggaggct tttttggagg cctagggacg tacccaattc gccctatagt gagtcgtatt    4800
acgcgcgctc actggccgtc gttttacaac gtcgtgactg ggaaaaccct ggcgttaccc    4860
aacttaatcg ccttgcagca catcccctt tcgccagctg gcgtaatagc gaagaggccc     4920
gcaccgatcg cccttcccaa cagttgcgca gcctgaatgg cgaatggcgc gacgcgccct    4980
gtagcggcgc attaagcgcg gcgggtgtgg tggttacgcg cagcgtgacc gctacacttg    5040
ccagcgccct agcgcccgct cctttcgctt tcttcccttc ctttctcgcc acgttcgccg    5100
gctttccccg tcaagctcta aatcgggggc tccctttagg gttccgattt agtgctttac    5160
ggcacctcga ccccaaaaaa cttgattagg gtgatggttc acgtagtggg ccatcgccct    5220
gatagacggt ttttcgccct ttgacgttgg agtccacgtt ctttaatagt ggactcttgt    5280
tccaaactgg aacaacactc aaccctatct cggtctattc ttttgattta agggattt     5340 tgccgatttc ggcctattgg ttaaaaaatg agctgattta acaaaatt aacgcgaatt      5400 ttaacaaaat attaacgttt acaatttccc aggtggcact tttcgggaa atgtgcgcgg     5460 aaccctatt tgtttattt tctaaataca ttcaaatatg tatccgctca tgagacaata     5520
accctgataa atgcttcaat aatattgaaa aggaagagt atgagtattc aacatttccg    5580
tgtcgccctt attccctttt tgcggcatt ttgccttcct gttttgctc acccagaaac     5640 gctggtgaaa gtaaaagatg ctgaagatca gttgggtgca cgagtgggtt acatcgaact    5700
ggatctcaac agcggtaaga tccttgagag ttttcgcccc gaagaacgtt ttccaatgat    5760
gagcactttt aaagttctgc tatgtggcgc ggtattatcc cgtattgacg ccgggcaaga    5820
gcaactcggt cgccgcatac actattctca gaatgacttg gttgagtact caccagtcac    5880
agaaaagcat cttacggatg gcatgacagt aagagaatta tgcagtgctg ccataaccat    5940
gagtgataac actgcggcca acttacttct gacaacgatc ggaggaccga aggagctaac    6000
cgcttttttg cacaacatgg gggatcatgt aactcgcctt gatcgttggg aaccggagct    6060
gaatgaagcc ataccaaacg acgagcgtga ccacgatg cctgtagcaa tggcaacaac     6120
gttgcgcaaa ctattaactg gcgaactact tactctagct tcccggcaac aattaataga    6180
ctggatggag gcggataaag ttgcaggacc acttctgcgc tcggcccttc cggctggctg    6240
gtttattgct gataaatctg gagccggtga gcgtgggtct cgcggtatca ttgcagcact    6300
ggggccagat ggtaagccct cccgtatcgt agttatctac acgacgggga gtcaggcaac    6360 tatgatgaa cgaaatagac agatcgctga gataggtgcc tcactgatta gcattggta     6420 actgtcagac caagtttact catatatact ttagattgat ttaaaacttc attttttaatt   6480 taaaaggatc taggtgaaga tcctttttga atctcatg accaaaatcc cttaacgtga     6540
gttttcgttc cactgagcgt cagacccct agaaaagatc aaaggatctt cttgagatcc    6600
tttttttctg cgcgtaatct gctgcttgca acaaaaaaa ccaccgctac cagcggtggt    6660
ttgtttgccg gatcaagagc taccaactct ttttccgaag gtaactggct tcagcagagc     6720
gcagatacca aatactgtcc ttctagtgta gccgtagtta ggccaccact tcaagaactc    6780
```

| | |
|---|---|
| tgtagcaccg cctacatacc tcgctctgct aatcctgtta ccagtggctg ctgccagtgg | 6840 |
| cgataagtcg tgtcttaccg ggttggactc aagacgatag ttaccggata aggcgcagcg | 6900 |
| gtcgggctga acggggggtt cgtgcacaca gcccagcttg gagcgaacga cctacaccga | 6960 |
| actgagatac ctacagcgtg agctatgaga aagcgccacg cttcccgaag ggagaaaggc | 7020 |
| ggacaggtat ccggtaagcg gcagggtcgg aacaggagag cgcacgaggg agcttccagg | 7080 |
| gggaaacgcc tggtatcttt atagtcctgt cgggtttcgc cacctctgac ttgagcgtcg | 7140 |
| atttttgtga tgctcgtcag ggggggggag cctatggaaa aacgccagca acgcggcctt | 7200 |
| tttacggttc ctggccttt gctggccttt tgctcacatg ttctttcctg cgttatcccc | 7260 |
| tgattctgtg gataaccgta ttaccgcctt tgagtgagct gataccgctc gccgcagccg | 7320 |
| aacgaccgag cgcagcgagt cagtgagcga ggaagcggaa gagcgcccaa tacgcaaacc | 7380 |
| gcctctcccc gcgcgttggc cgattcatta atgcagctgg cacgacaggt ttcccgactg | 7440 |
| gaaagcgggc agtgagcgca acgcaattaa tgtgagttag ctcactcatt aggcaccccca | 7500 |
| ggctttacac tttatgcttc cggctcgtat gttgtgtgga attgtgagcg gataacaatt | 7560 |
| tcacacagga aacagctatg accatgatta cgccaagcgc gcaattaacc ctcactaaag | 7620 |
| ggaacaaaag ctggagctgc aagcttgcat gctggccatt gcatacgttg tatcca | 7676 |

<210> SEQ ID NO 16
<211> LENGTH: 7819
<212> TYPE: DNA
<213> ORGANISM: Artificial sequence
<220> FEATURE:
<223> OTHER INFORMATION: Construct pLTR1.20/GAPDH-eGFP-WPRE

<400> SEQUENCE: 16

| | |
|---|---|
| ccattgcata cgttgtatcc atatcataat atgtacattt atattggctc atgtccaaca | 60 |
| ttaccgccat gttgacattg attattgact agttattaat agtaatcaat tacggggtca | 120 |
| ttagttcata gcccatatat ggagttccgc gttacataac ttacggtaaa tggcccgcct | 180 |
| ggctgaccgc ccaacgaccc ccgcccattg acgtcaataa tgacgtatgt tcccatagta | 240 |
| acgccaatag ggactttcca ttgacgtcaa tgggtggagt atttacggta aactgcccac | 300 |
| ttggcagtac atcaagtgta tcatatgcca agtacgcccc ctattgacgt caatgacggt | 360 |
| aaatggcccg cctggcatta tgcccagtac atgaccttat gggactttcc tacttggcag | 420 |
| tacatctacg tattagtcat cgctattacc atggtgatgc ggttttggca gtacatcaat | 480 |
| gggcgtggat agcggtttga ctcacgggga tttccaagtc tccaccccat tgacgtcaat | 540 |
| gggagtttgt tttggcacca aaatcaacgg gactttccaa aatgtcgtaa caactccgcc | 600 |
| ccattgacgc aaatgggcgg taggcgtgta cggtgggagg tctatataag cagagctcgt | 660 |
| ttagtgaacc tggcgcccga cagggactg ctagcctggg caggtaagta tcaaggttac | 720 |
| aagacaggtt taaggagacc aatagaaact gggcttgtcg agacagagaa gactcttgcg | 780 |
| tttctgatag gcacctattg gtcttactga catccacttt gcctttctct ccacaggtgt | 840 |
| ccactcccag ttcgctagcg ttaacttta aaagaaaagg ggggattggg gggtacagtg | 900 |
| caggggaaag aatagtagac ataatagcaa cagacataca aactaaagaa ttacaaaaac | 960 |
| aaattacaaa aattcaaaat tttatcgatc acgagactag cctcgaggat atcagttccc | 1020 |
| caactttccc gcctctcagc ctttgaaaga agaaagggg aggggcagg ccgcgtgcag | 1080 |
| ccgcgagcgg tgctgggctc cggctccaat tccccatctc agtcgttccc aaagtcctcc | 1140 |
| tgtttcatcc aagcgtgtaa gggtcccccgt ccttgactcc ctagtgtcct gctgcccaca | 1200 |

-continued

```
gtccagtcct gggaaccagc accgatcacc tcccatcggg ccaatctcag tcccttcccc    1260
cctacgtcgg ggcccacacg ctcggtgcgt gcccagttga accaggcggc tgcggaaaaa    1320
aaaaagcggg gagaaagtag ggcccggcta ctagcggttt tacgggcgca cgtagctcag    1380
gcctcaagac cttgggctgg gactggctga gcctggcggg aggcgggtc cgagtcaccg     1440 cctgccgccg cgccccggt ttctataaat tgagcccgca gcctcccgct tcgctctctg     1500
ctcctcctgg gatccaccgg tcgccaccat ggtgagcaag ggcgaggagc tgttcaccgg    1560
ggtggtgccc atcctggtcg agctggacgg cgacgtaaac ggccacaagt tcagcgtgtc    1620
cggcgagggc gagggcgatg ccacctacgg caagctgacc ctgaagttca tctgcaccac    1680
cggcaagctg cccgtgccct ggcccaccct cgtgaccacc ctgacctacg gcgtgcagtg    1740
cttcagccgc taccccgacc acatgaagca gcacgacttc ttcaagtccg ccatgcccga    1800
aggctacgtc caggagcgca ccatcttctt caaggacgac ggcaactaca agacccgcgc    1860
cgaggtgaag ttcgagggcg acaccctggt gaaccgcatc gagctgaagg gcatcgactt    1920
caaggaggac ggcaacatcc tggggcacaa gctggagtac aactacaaca gccacaacgt    1980
ctatatcatg gccgacaagc agaagaacgg catcaaggtg aacttcaaga tccgccacaa    2040
catcgaggac ggcagcgtgc agctcgccga ccactaccag cagaacaccc ccatcggcga    2100
cggccccgtg ctgctgcccg acaaccacta cctgagcacc cagtccgccc tgagcaaaga    2160
ccccaacgag aagcgcgatc acatggtcct gctggagttc gtgaccgccg ccgggatcac    2220
tctcggcatg gacgagctgt acaagtaaag cggccgcgtc gacaatcaac ctctggatta    2280
caaaatttgt gaaagattga ctggtattct taactatgtt gctccttta cgctatgtgg     2340 atacgctgct ttaatgcctt tgtatcatgc tattgcttcc cgtatggctt tcattttctc    2400
ctccttgtat aaatcctggt tgctgtctct ttatgaggag ttgtggcccg ttgtcaggca    2460
acgtggcgtg gtgtgcactg tgtttgctga cgcaaccccc actggttggg gcattgccac    2520
cacctgtcag ctcctttccg ggactttcgc tttccccctc cctattgcca cggcggaact    2580
catcgccgcc tgccttgccc gctgctggac aggggctcgg ctgttgggca ctgacaattc    2640
cgtggtgttg tcggggaagc tgacgtcctt tccatggctg ctcgcctgtg ttgccacctg    2700
gattctgcgc gggacgtcct tctgctacgt cccttcggcc ctcaatccag cggaccttcc    2760
ttcccgcggc ctgctgccgg ctctgcggcc tcttccgcgt cttcgccttc gccctcagac    2820
gagtcggatc tccctttggg ccgcctcccc gcctggaatt cgagctcggt acctttaaga    2880
ccaatgactt acaaggcagc tgtagatctt agccactttt taaaagaaaa ggggggactg    2940
gaagggctaa ttcactccca acgaagacaa gatctgcttt ttgcttgtac tgggtctctc    3000
tggttagacc agatctgagc ctgggagctc tctggctaac tagggaaccc actgcttaag    3060
cctcaataaa gcttgccttg agtgcttcaa gtagtgtgtg cccgtctgtt gtgtgactct    3120
ggtaactaga gatccctcag acccttttag tcagtgtgga aaatctctag cagtggcgcc    3180
cgaacaggga cttgaaagcg aaagggaaac cagaggagct ctctcgacgc aggactcggc    3240
ttgctgaagc gcgcacggca agaggcgagg ggcggcgact ggtgagtacg ccaaaaattt    3300
tgactagcgg aggctagaag gagagagatg ggtgcgagag cgtcagtatt aagcggggga    3360
gaattagatc gcgatgggaa aaaattcggt taaggccagg gggaaagaaa aaatataaat    3420
taaaacatat agtatgggca agcagggagc tagaacgatt cgcagttaat cctggcctgt    3480
tagaaacatc agaaggctgt agacaaatac tgggacagct acaaccatcc cttcagacag    3540
```

```
gatcagaaga acttagatca ttatataata cagtagcaac cctctattgt gtgcatcaaa    3600
ggatagagat aaaagacacc aaggaagctt tagacaagat agaggaagag caaaacaaaa    3660
gtaagaccac cgcacagcaa gcggccgctg atcttcagac ctggaggagg agatatgagg    3720
gacaattgga gaagtgaatt atataaatat aaagtagtaa aaattgaacc attaggagta    3780
gcacccacca aggcaaagag aagagtggtg cagagagaaa aaagagcagt gggaatagga    3840
gctttgttcc ttgggttctt gggagcagca ggaagcacta tgggcgcagc gtcaatgacg    3900
ctgacggtac aggccagaca attattgtct ggtatagtgc agcagcagaa caatttgctg    3960
agggctattg aggcgcaaca gcatctgttg caactcacag tctggggcat caagcagctc    4020
caggcaagaa tcctggctgt ggaaagatac ctaaaggatc aacagctcct ggggatttgg    4080
ggttgctctg gaaaactcat ttgcaccact gctgtgcctt ggaatgctag ttggagtaat    4140
aaatctctgg aacagatttg gaatcacacg acctggatgg agtgggacag agaaattaac    4200
aattacacaa gcttaataca ctccttaatt gaagaatcgc aaaaccagca agaaaagaat    4260
gaacaagaat tattggaatt agataaatgg gcaagtttgt ggaattggtt taacataaca    4320
aattggctgt ggtatataaa attattcata atgatagtag gaggcttggt aggtttaaga    4380
atagtttttg ctgtactttc tatagtgaat agagttaggc agggatattc accattatcg    4440
tttcagaccc acctcccaac cccgagggga cccgacaggc ccgaaggaat agaagaagaa    4500
ggtggagaga gagacagaga cagatccatt cgattagtga acggatccag acatgataag    4560
atacattgat gagtttggac aaaccacaac tagaatgcag tgaaaaaaat gctttatttg    4620
tgaaatttgt gatgctattg ctttatttgt aaccattata agctgcaata aacaagttaa    4680
caacaacaat tgcattcatt ttatgtttca ggttcagggg gagatgtggg aggttttta    4740 aagcaagtaa aacctctaca atgtggtaa tcccgcccct aactccgccc atcccgcccc    4800
taactccgcc cagttccgcc cattctccgc cccatggctg actaatttt tttattatg    4860 cagaggccga ggccgcctcg gcctctgagc tattccagaa gtagtgagga gcttttttg    4920 gaggcctagg gacgtaccca attcgcccta gtgagtcg tattacgcgc gctcactggc    4980
cgtcgtttta caacgtcgtg actgggaaaa ccctggcgtt acccaactta atcgccttgc    5040
agcacatccc cctttcgcca gctggcgtaa tagcgaagag gcccgcaccg atcgcccttc    5100
ccaacagttg cgcagcctga atggcgaatg gcgcgacgcg ccctgtagcg gcgcattaag    5160
cgcggcgggt gtggtggtta cgcgcagcgt gaccgctaca cttgccagcg ccctagcgcc    5220
cgctcctttc gctttcttcc cttcctttct cgccacgttc gccggctttc cccgtcaagc    5280
tctaaatcgg gggctccctt tagggttccg atttagtgct ttacggcacc tcgaccccaa    5340
aaaacttgat tagggtgatg gttcacgtag tgggccatcg ccctgataga cggtttttcg    5400 cccttgacg ttggagtcca cgttctttaa tagtggactc ttgttccaaa ctggaacaac    5460
actcaaccct atctcggtct attcttttga tttataaggg attttgccga tttcggccta    5520
ttggttaaaa aatgagctga tttaacaaaa atttaacgcg aattttaaca aaatattaac    5580
gtttacaatt tcccaggtgg cacttttcgg ggaaatgtgc gcggaacccc tatttgttta    5640
tttttctaaa tacattcaaa tatgtatccg ctcatgagac aataaccctg ataaatgctt    5700
caataatatt gaaaaggaa gagtatgagt attcaacatt tccgtgtcgc ccttattccc    5760
ttttttgcgg cattttgcct tcctgttttt gctcacccag aaacgctggt gaaagtaaaa    5820
gatgctgaag atcagttggg tgcacgagtg ggttacatcg aactggatct caacagcggt    5880
aagatccttg agagttttcg ccccgaagaa cgttttccaa tgatgagcac ttttaaagtt    5940
```

-continued

```
ctgctatgtg gcgcggtatt atcccgtatt gacgccgggc aagagcaact cggtcgccgc    6000
atacactatt ctcagaatga cttggttgag tactcaccag tcacagaaaa gcatcttacg    6060
gatggcatga cagtaagaga attatgcagt gctgccataa ccatgagtga taacactgcg    6120
gccaacttac ttctgacaac gatcggagga ccgaaggagc taaccgcttt tttgcacaac    6180 atggggatc atgtaactcg ccttgatcgt tgggaaccgg agctgaatga agccatacca    6240
aacgacgagc gtgacaccac gatgcctgta gcaatggcaa caacgttgcg caaactatta    6300
actggcgaac tacttactct agcttcccgg caacaattaa tagactggat ggaggcggat    6360
aaagttgcag gaccacttct gcgctcggcc cttccggctg gctggtttat tgctgataaa    6420
tctggagccg gtgagcgtgg gtctcgcggt atcattgcag cactggggcc agatggtaag    6480
ccctcccgta tcgtagttat ctacacgacg gggagtcagg caactatgga tgaacgaaat    6540
agacagatcg ctgagatagg tgcctcactg attaagcatt ggtaactgtc agaccaagtt    6600
tactcatata ctttagat tgatttaaaa cttcatttt aatttaaaag gatctaggtg    6660
aagatccttt ttgataatct catgaccaaa atcccttaac gtgagtttc gttccactga    6720 gcgtcagacc ccgtagaaaa gatcaaagga tcttcttgag atcctttttt tctgcgcgta    6780
atctgctgct tgcaaacaaa aaaaccaccg ctaccagcgg tggtttgttt gccggatcaa    6840
gagctaccaa ctcttttttcc gaaggtaact ggcttcagca gagcgcagat accaaatact    6900
gtccttctag tgtagccgta gttaggccac cacttcaaga actctgtagc accgcctaca    6960
tacctcgctc tgctaatcct gttaccagtg gctgctgcca gtggcgataa gtcgtgtctt    7020
accgggttgg actcaagacg atagttaccg gataaggcgc agcggtcggg ctgaacgggg    7080
ggttcgtgca cacagcccag cttggagcga acgacctaca ccgaactgag atacctacag    7140
cgtgagctat gagaaagcgc cacgcttccc gaagggagaa aggcggacag gtatccggta    7200
agcggcaggg tcggaacagg agagcgcacg agggagcttc cagggggaaa cgcctggtat    7260
ctttatagtc ctgtcgggtt tcgccacctc tgacttgagc gtcgatttt gtgatgctcg    7320 tcagggggc ggagcctatg gaaaaacgcc agcaacgcgg cctttttacg gttcctggcc    7380
ttttgctggc cttttgctca catgttcttt cctgcgttat cccctgattc tgtggataac    7440
cgtattaccg cctttgagtg agctgatacc gctcgccgca gccgaacgac cgagcgcagc    7500
gagtcagtga gcgaggaagc ggaagagcgc ccaatacgca aaccgcctct ccccgcgcgt    7560
tggccgattc attaatgcag ctggcacgac aggtttcccg actggaaagc gggcagtgag    7620
cgcaacgcaa ttaatgtgag ttagctcact cattaggcac cccaggcttt acactttatg    7680
cttccggctc gtatgttgtg tggaattgtg agcggataac aatttcacac aggaaacagc    7740
tatgaccatg attacgccaa gcgcgcaatt aaccctcact aaagggaaca aaagctggag    7800
ctgcaagctt gcatgctgg                                                  7819
```